United States Patent
Trapnell et al.

(10) Patent No.: US 12,043,844 B2
(45) Date of Patent: Jul. 23, 2024

(54) CELL THERAPY WITH LENTIVIRAL TRANSDUCED CSF2RA TRANSGENE IN THE TREATMENT OF HEREDITARY PULMONARY ALVEOLAR PROTEINOSIS

(71) Applicants: CHILDREN'S HOSPITAL MEDICAL CENTER, Cincinnati, OH (US); MEDIZINISCHE HOCHSCHULE HANNOVER, Hannover (DE)

(72) Inventors: Bruce C. Trapnell, Cincinnati, OH (US); Takuji Suzuki, Tochigi (JP); Thomas Moritz, Bonn (DE); Nico Lachmann, Burgdorf (DE); Axel Schambach, Hannover (DE)

(73) Assignees: Children's Hospital Medical Center; Medizinische Hochschule Hannover, Hannover (DE)

( * ) Notice: Subject to any disclaimer, the term of this patent is extended or adjusted under 35 U.S.C. 154(b) by 1220 days.

(21) Appl. No.: 16/613,592

(22) PCT Filed: May 16, 2018

(86) PCT No.: PCT/US2018/032933
§ 371 (c)(1),
(2) Date: Nov. 14, 2019

(87) PCT Pub. No.: WO2018/213421
PCT Pub. Date: Nov. 22, 2018

(65) Prior Publication Data
US 2020/0199623 A1 Jun. 25, 2020

Related U.S. Application Data

(60) Provisional application No. 62/507,399, filed on May 17, 2017.

(51) Int. Cl.
*A01K 67/0276* (2024.01)
*A61K 35/15* (2015.01)
(Continued)

(52) U.S. Cl.
CPC .......... *C12N 15/86* (2013.01); *A01K 67/0276* (2013.01); *A61K 35/15* (2013.01);
(Continued)

(58) Field of Classification Search
None
See application file for complete search history.

(56) References Cited

U.S. PATENT DOCUMENTS

| | | | |
|---|---|---|---|
| 9,220,755 B2 * | 12/2015 | Chakraborty | ........ A61K 38/191 |
| 11,001,806 B2 | 5/2021 | Post | |
| 2017/0335282 A1 | 11/2017 | Post | |

FOREIGN PATENT DOCUMENTS

| | | |
|---|---|---|
| EP | 3256569 A1 | 12/2017 |
| EP | 3619295 A1 | 3/2020 |

(Continued)

OTHER PUBLICATIONS

Cordero, LO. Cloning vector pRRL-sffv-eGFP-cmv-hsGDNF, complete sequence (GenBank KJ697753, direct submission Apr. 12, 2014 ), pp. 1-3 (Year: 2014).*

(Continued)

*Primary Examiner* — Arthur S Leonard
(74) *Attorney, Agent, or Firm* — KDW Firm PLLC

(57) ABSTRACT

The disclosure provides compositions and methods for cell therapy of hPAP in humans using gene corrected and in vitro differentiated patient autologous macrophage cells. The disclosure also provides compositions in the form of a cell product and related compositions and methods for making (Continued)

the cell product and for direct pulmonary transplantation of same.

28 Claims, 36 Drawing Sheets

Specification includes a Sequence Listing.

(51) Int. Cl.
*A61K 48/00* (2006.01)
*C12N 15/86* (2006.01)
(52) U.S. Cl.
CPC .... *A61K 48/0058* (2013.01); *A01K 2217/075* (2013.01); *A01K 2227/105* (2013.01); *A01K 2267/0306* (2013.01); *C12N 2740/16043* (2013.01); *C12N 2800/22* (2013.01); *C12N 2830/008* (2013.01)

(56) References Cited

FOREIGN PATENT DOCUMENTS

WO 2016127259 A1 8/2016
WO 2018213421 A1 11/2018

OTHER PUBLICATIONS

Galibert et al. Woodchuck hepatitis virus, complete genome (GenBank J02442, published Aug. 3, 1993), pp. 1-2 (Year: 1993).*
Han et al. *Homo sapiens* EF1 a mRNA, complete cds (GenBank EF362804, published Jul. 27, 2007), pp. 1-2 (Year: 2007).*
Ackermann, Mania et al. "Ex vivo Generation of Genetically Modified Macrophages from Human Induced Pluripotent Stem Cells." Transfusion medicine and hemotherapy : offizielles Organ der Deutschen Gesellschaft fur Transfusionsmedizin und Immunhamatologie vol. 44,3 (2017): 135-142.
Del Carmen Ortuno-Costela et al., "The Challenge of Bringing iPSCs to the Patient" Int. J. Mol. Sci. 2019, 20, 6305.
Happle et al., "Pulmonary transplantation of macrophage progenitors as effective and long-lasting therapy for hereditary pulmonary alveolar proteinosis" Science Translational Medicine Aug. 20, 2014: vol. 6, Issue 250, pp. 250ra113.
Keeler et al., "Gene Therapy 2017: Progress and Future Directions" Citation: Clin Transl Sci (2017) 10, 242-248.
Lachmann et al., "Large-Scale Hematopoietic Differentiation of Human Induced Pluripotent Stem Cells Provides Granulocytes or Macrophages for Cell Replacement Therapies" Stem Cell Reports vol. 4, Issue 2, p. 282-296, Feb. 10, 2015.
Turinetto et al., "Induced Pluripotent Stem Cells: Advances in the Quest for Genetic Stability during Reprogramming Process" Int. J. Mol. Sci. 2017, 18, 1952.
Kleff, V. et al. (2011). "Gene therapy of betac-deficient pulmonary alveolar proteinosis (betac-PAP): Studies in murine in vivo model." Molecular Therapy 16(4):757-764.
Lachmann, N. et al. (2015). "Tightly regulated 'all-in-one' lentiviral vectors for protection of human hematopoietic cells from anticancer chemotherapy." Gene Therapy 22:883-892.

Martinez-Moczygemba, M. et al. (2008). "Pulmonary alveolar proteinosis caused by deletion of the GM-CSFRalpha gene in the X chromosome pseudoautosomal region 1." The Journal of Experimental Medicine 205 (12):2711-2716.
Montini, E. et al. (2009). "The genotoxic potential of retroviral vectors is strongly modulated by vector design and integration site selection in a mouse model of HSC gene therapy." The Journal of Clinical Investigation 119 (4):964-975.
Oliveira, H. et al. (2016). "Combined bone marrow-derived mesenchymal stromal cell therapy and one-way endobrochial valve placement in patients with pulmonary emphysema: A Phase I trial." Stem Cells Translational Medicine 6:962-969.
Shibata, Y. et al. (2001). "GM-CSF regulates alveolar macrophage differentiation and innate immunity in the lung through PU.1." Immunity 15:557-567.
Suzuki, T. et al. (2011). "Hereditary pulmonary alveolar proteinosis caused by recessive CSF2RB mutations." European Repiratory Journal 37:201-217.
Suzuki, T. et al. (2010). "Herditary pulmonary alveolar proteinosis." American Journal of Respiratory Critical Care Medicine 182:1292-134.
Suzuki, T. et al. (2008). "Familial pulmonary alveolar proteinosis cause by mutations in CSF2RA." The Journal of Experimental Medicine 205(12):2703-2710.
Zuo, W. et al. (2015). "p63+Krt5+ distal airway stem cells are essential for lung regeneration." Nature 517:616-630.
International Preliminary Report on Patentability received for PCT Application No. PCT/US2018/032933 mailed on Nov. 28, 2019 (7 pages).
Partial European Search Report received for EP Application No. 18801714.9 mailed on Feb. 26, 2021 (13 pages).
Hetzel et al. (Apr. 2020) "Effective Hematopoietic Stem Cell-based Gene Therapy in a Murine Model of Hereditary Pulmonary Alveolar Proteinosis". Haematologica, 105(4):1147-1157.
Hetzel et al. (Dec. 1, 2017) "Function and Safety of Lentivirus-Mediated Gene Transfer for CSF2RA-Deficiency". Human Gene Therapy Methods, 28(6):318-329.
Lachmann et al. (May 1, 2013) "Generation of Functional Monocyte/ Macrophages by Genetic Correction of Patient-Specific iPSC in Congenital Pulmonary Alveolar Proteinosis". Molecular Therapy, 21(1):S34.
Raines et al. (Sep. 15, 1991) "Identification and Molecular Cloning of a Soluble Human Granulocyte-macrophage Colony-stimulating Factor Receptor". Proc Natl Acad Sci USA, 88(18):8203-8207.
International Search Report and Written Opinion of the International Searching Authority mailed on Oct. 2, 2018 for International Application No. PCT/US2018/032933, filed May 16, 2018 (9 pages).
Gearing, D. et al. (1989). "Expression cloning of a receptor for human granulocyte-macrophage colony-stimulating factor." *EMBO Journal* 8(12): 3667-3676.
Lachmann, N. et al. (2014). "Gene correction of human induced pluripotent stem cells repairs the cellular phenotype in pulmonary alveolar proteinosis." *American Journal of Respiratory and Critical Care Medicine* 189(2): 167-182.
Suzuki, T. et al. (Oct. 23, 2014). "Pulmonary macrophage transplantation therapy." *Nature* 514(7523): 450-454.

* cited by examiner

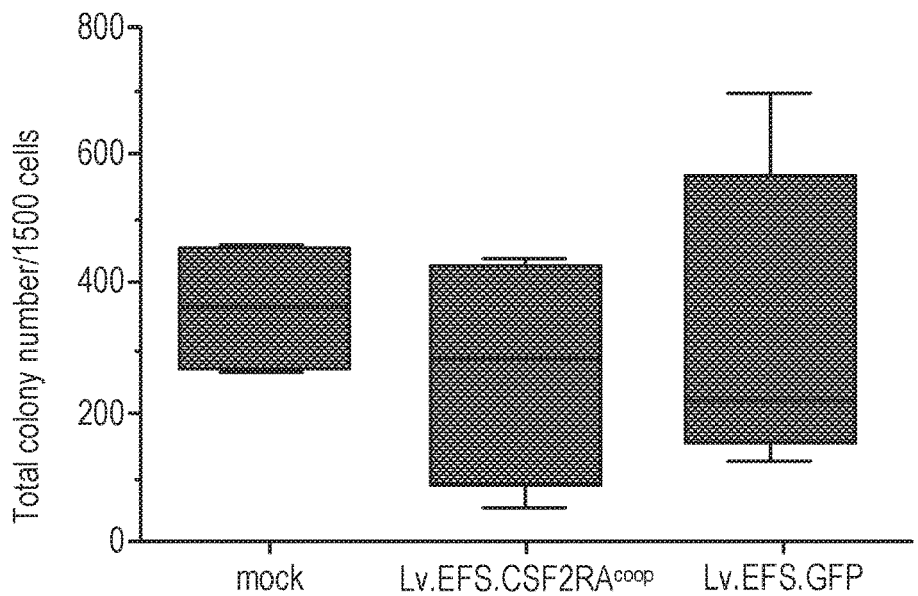
FIG. 10C
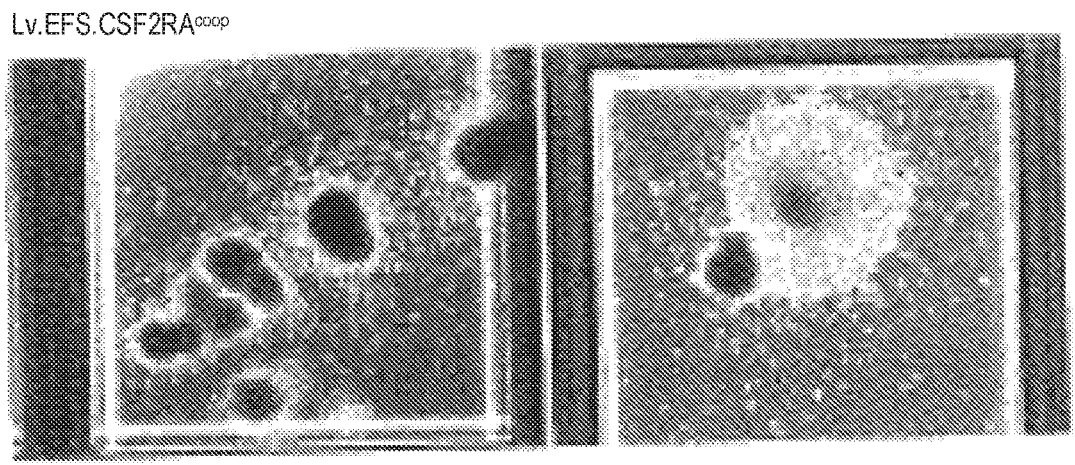
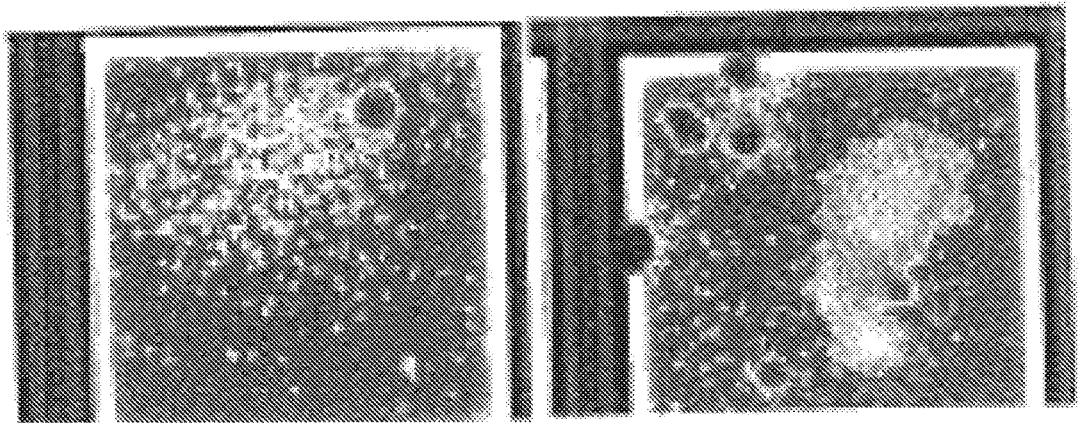
FIG. 10D

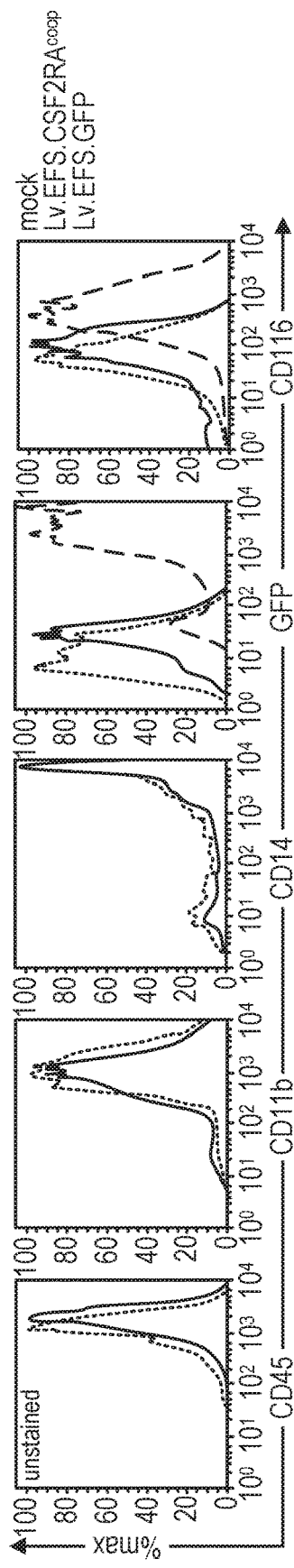
FIG. 10G
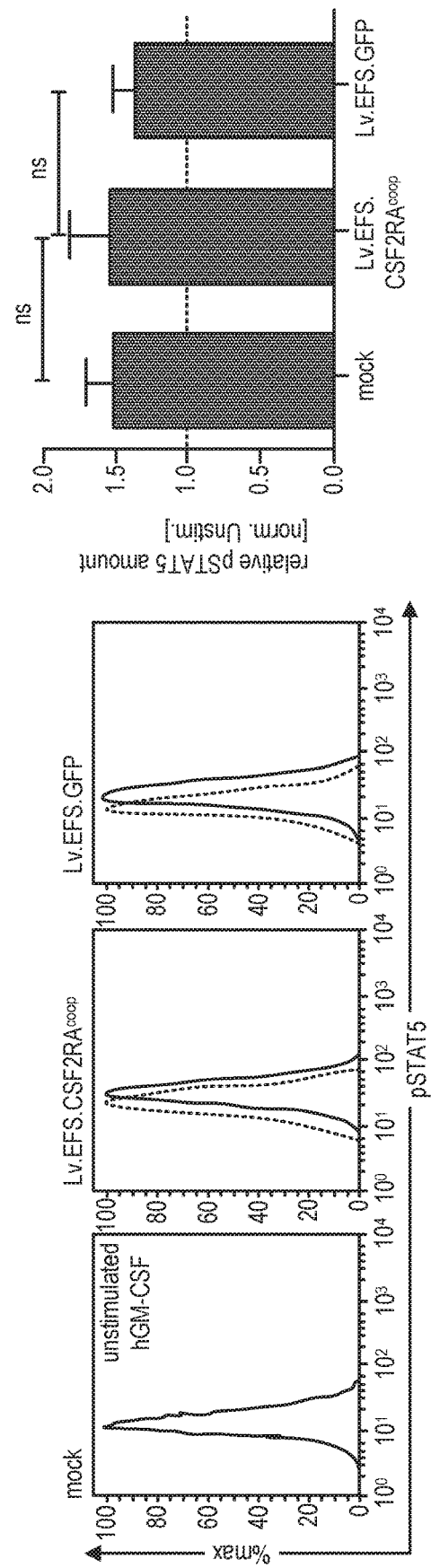
FIG. 10I
FIG. 10H

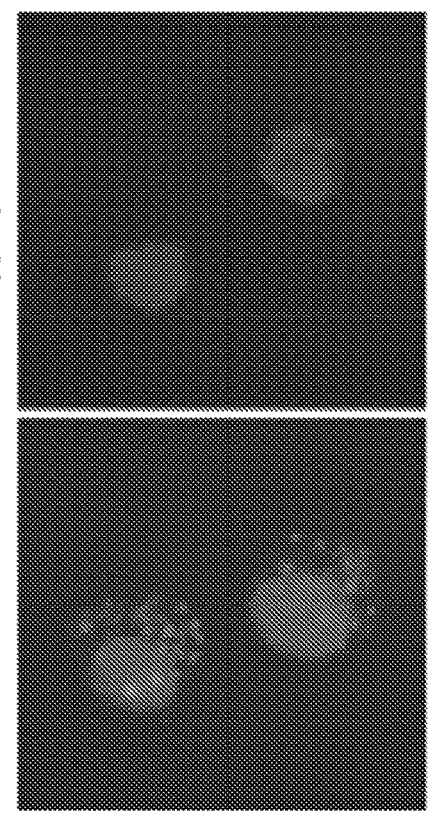
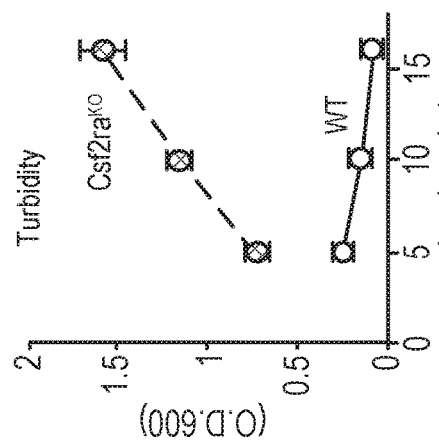
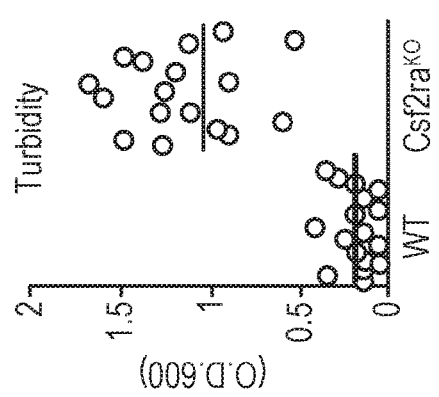
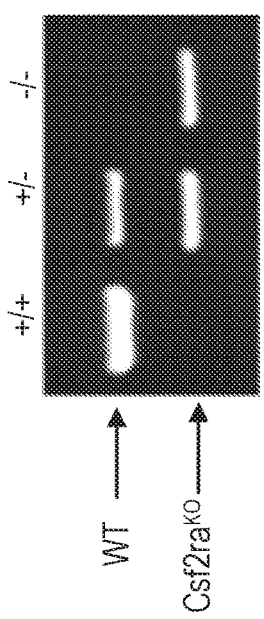
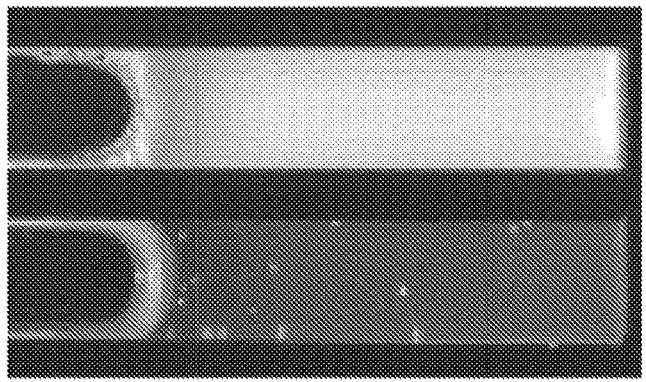

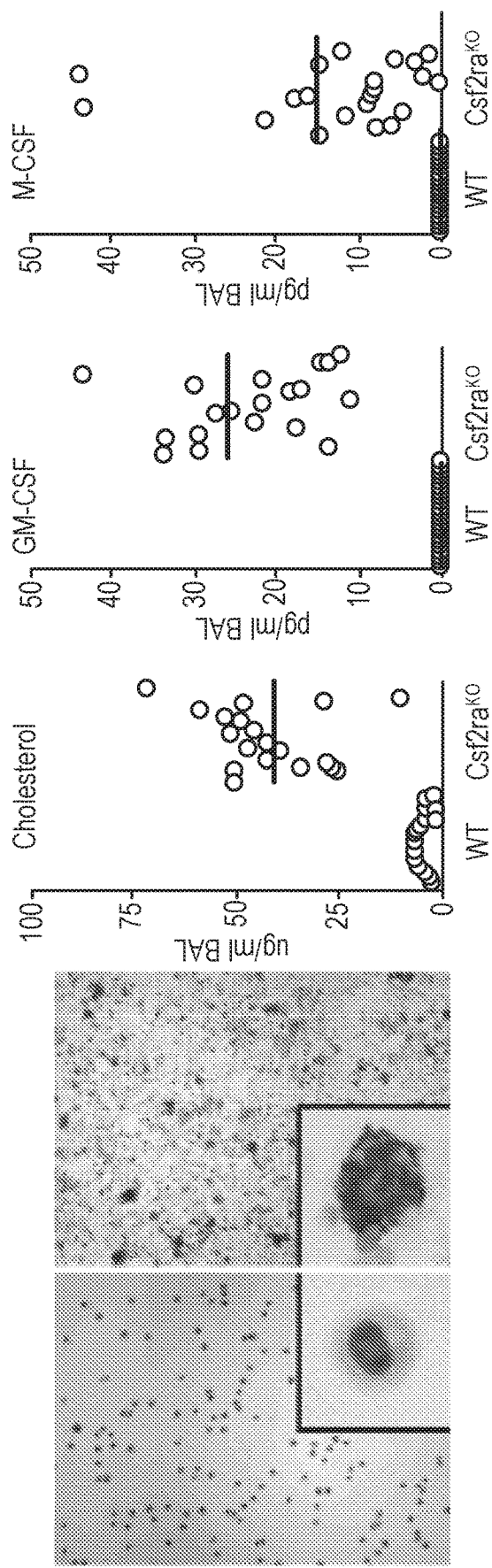
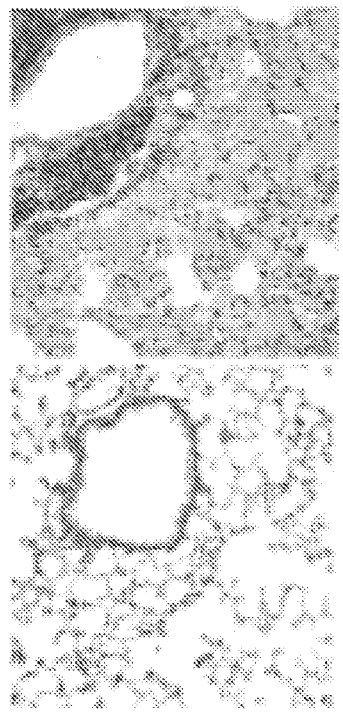

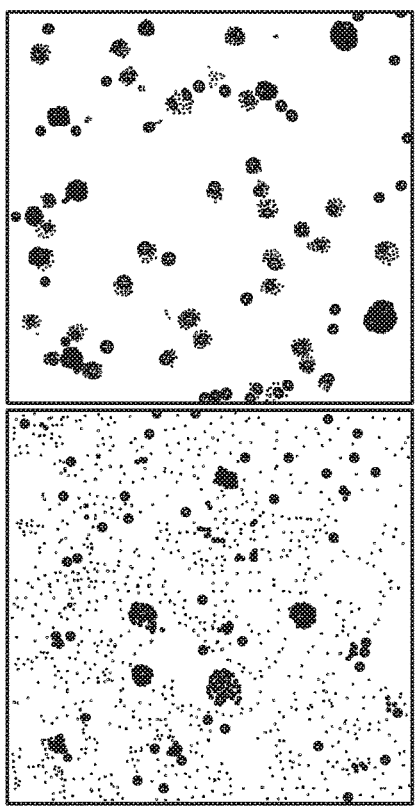
FIG. 12A
FIG. 12C
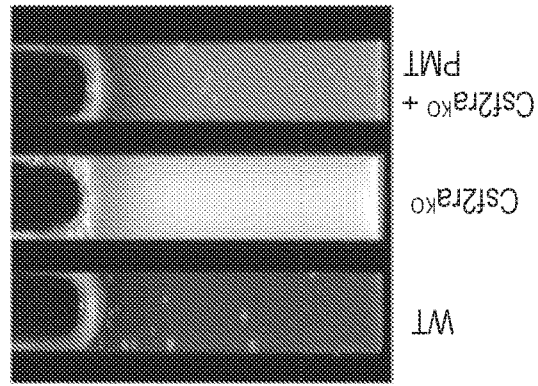
FIG. 12D
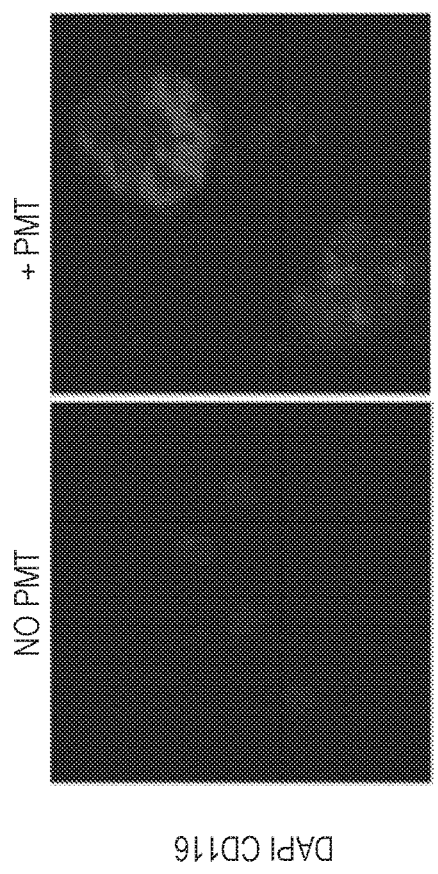
FIG. 12B

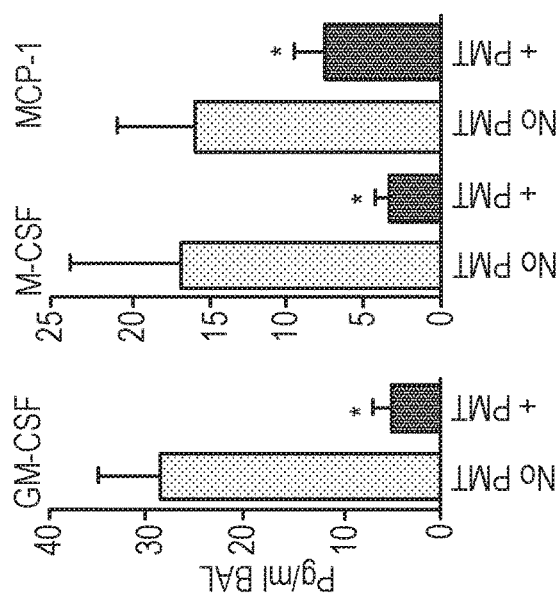
FIG. 12G
FIG. 12F
FIG. 12E
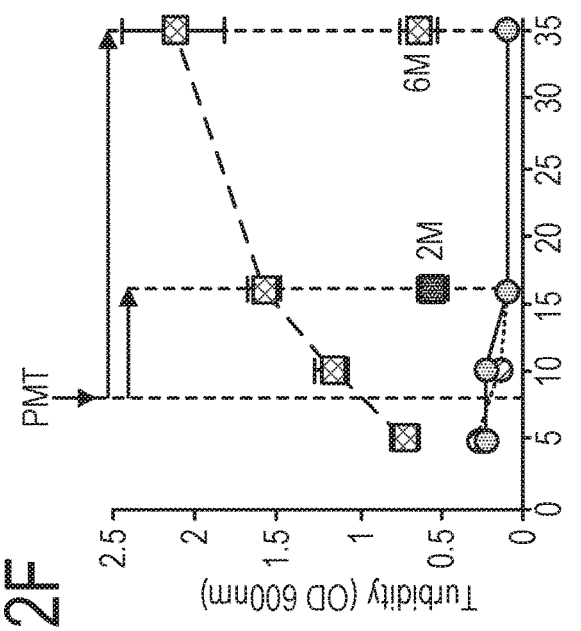
FIG. 12H
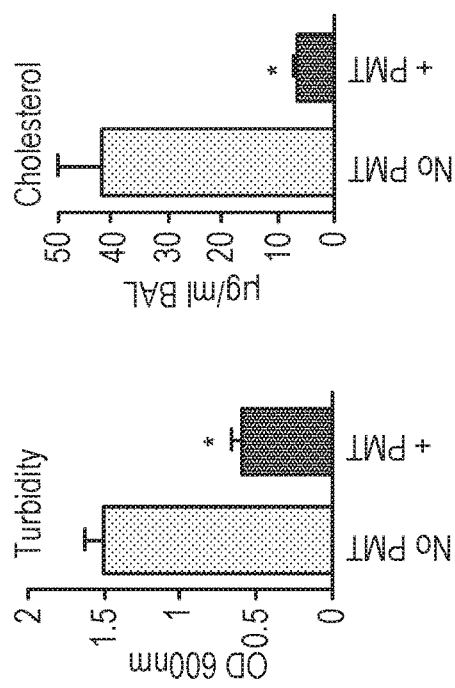

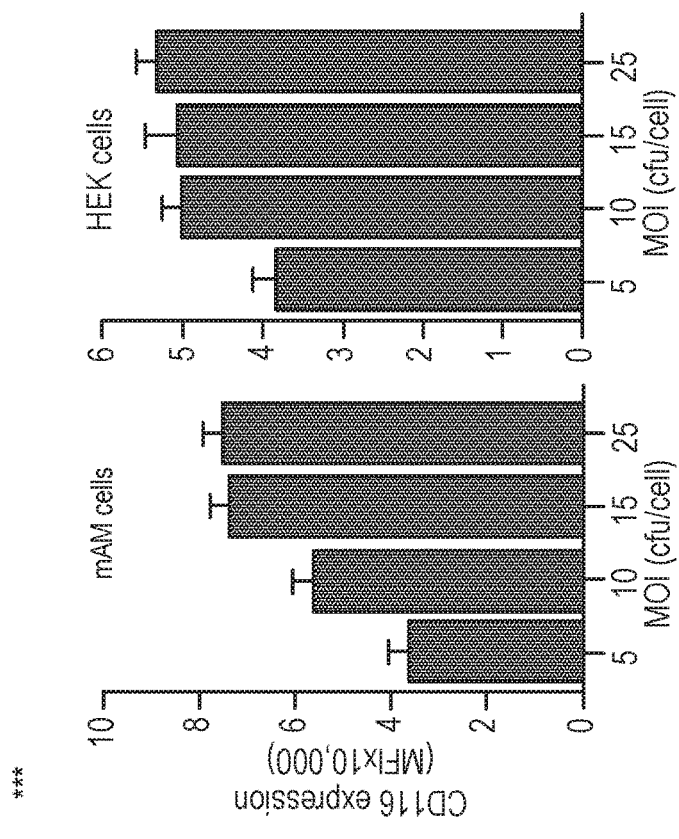
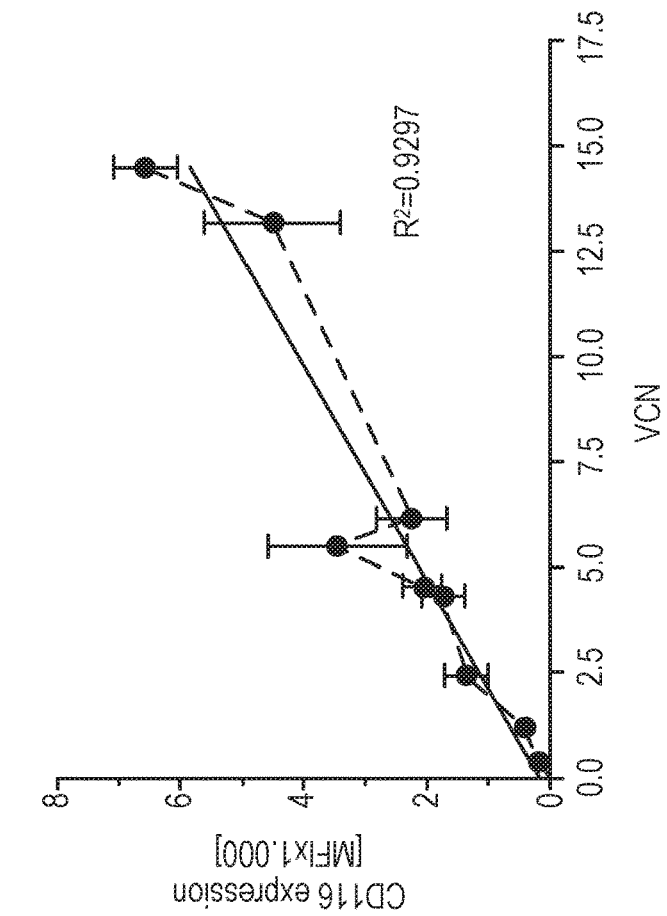
FIG. 15A
FIG. 15B

Fig. 19A

```
CCGATTGGTGGAAGTAAGGTGGTACGATCGTGCCTTATTAGGAAGGCAACAGACGGGTCTGACATGGATTGGAC
GAACCACTGAATTGCCGCATTGCAGAGATATTGTATTTAAGTGCCTAGCTCGATACAATAAACGGGTCTCTCTGGT
TAGACCAGATCTGAGCCTGGGAGCTCTCTGGCTAACTAGGGAACCCACTGCTTAAGCCTCAATAAAGCTTGCCTTG
AGTGCTTCAAGTAGTGTGTGCCCGTCTGTTGTGTGACTCTGGTAACTAGAGATCCCTCAGACCCTTTTAGTCAGTGT
GGAAAATCTCTAGCAGTGGCGCCCGAACAGGGACCTGAAAGCGAAAGGGAAACCAGAGCTCTCTCGACGCAGGA
CTCGGCTTGCTGAAGCGCGCACGGCAAGAGGCGAGGGGCGGCGACTGGTGAGTACGCCAAAAATTTTGACTAGC
GGAGGCTAGAAGGAGAGAGATGGGTGCGAGAGCGTCAGTATTAAGCGGGGGAGAATTAGATCGCGATGGGAA
AAAATTCGGTTAAGGCCAGGGGGAAAGAAAAAATATAAATTAAAACATATAGTATGGGCAAGCAGGGAGCTAGA
ACGATTCGCAGTTAATCCTGGCCTGTTAGAAACATCAGAAGGCTGTAGACAAATACTGGGACAGCTACAACCATCC
CTTCAGACAGGATCAGAAGAACTTAGATCATTATATAATACAGTAGCAACCCTCTATTGTGTGCATCAAAGGATAG
AGATAAAAGACACCAAGGAAGCTTTAGACAAGATAGAGGAAGAGCAAAACAAAAGTAAGACCACCGCACAGCAA
GCGGCCGCTGATCTTCAGACCTGGAGGAGGAGATATGAGGGACAATTGGAGAAGTGAATTATATAAATATAAAG
TAGTAAAAATTGAACCATTAGGAGTAGCACCCACCAAGGCAAAGAGAAGAGTGGTGCAGAGAGAAAAAGAGCA
GTGGGAATAGGAGCTTTGTTCCTTGGGTTCTTGGGAGCAGCAGGAAGCACTATGGGCGCAGCCTCAATGACGCTG
ACGGTACAGGCCAGACAATTATTGTCTGGTATAGTGCAGCAGCAGAACAATTTGCTGAGGGCTATTGAGGCGCAA
CAGCATCTGTTGCAACTCACAGTCTGGGGCATCAAGCAGCTCCAGGCAAGAATCCTGGCTGTGGAAAGATACCTA
AAGGATCAACAGCTCCTGGGGATTTGGGGTTGCTCTGGAAAACTCATTTGCACCACTGCTGTGCCTTGGAATGCTA
GTTGGAGTAATAAATCTCTGGAACAGATTTGGAATCACACGACCTGGATGGAGTGGGACAGAGAAATTAACAATT
ACACAAGCTTAATACACTCCTTAATTGAAGAATCGCAAAACCAGCAAGAAAAGAATGAACAAGAATTATTGGAATT
AGATAAATGGGCAAGTTTGTGGAATTGGTTTAACATAACAAATTGGCTGTGGTATATAAAATTATTCATAATGATA
GTAGGAGGCTTGGTAGGTTTAAGAATAGTTTTTGCTGTACTTTCTATAGTGAATAGAGTTAGGCAGGGATATTCAC
CATTATCGTTTCAGACCCACCTCCCAACCCCGAGGGGACCCGACAGGCCCGAAGGAATAGAAGAAGAAGGTGGA
GAGAGAGACAGAGACAGATCCATTCGATTAGTGAACGGATCTCGACGGTATCGGTTAACTTTTAAAAGAAAAGGG
GGGATTGGGGGGTACAGTGCAGGGGAAAGAATAGTAGACATAATAGCAACAGACATACAAACTAAAGAATTACA
AAAACAAATTACAAAAATTCAAAATTTTATCGATTGGCTCCGGTGCCCGTCAGTGGGCAGAGCGCACATCGCCCAC
AGTCCCCGAGAAGTTGGGGGGAGGGGTCGGCAATTGAACCGGTGCCTAGAGAAGGTGGCGCGGGGTAAACTGG
GAAAGTGATGTCGTGTACTGGCTCCGCCTTTTTCCCGAGGGTGGGGGAGAACCGTATATAAGTGCAGTAGTCGCC
GTGAACGTTCTTTTTCGCAACGGGTTTGCCGCCAGAACACAGGTGTCGTGACGCGGGATCCACCGGTGCCACCAT
GCTGCTGCTCGTGACAAGCCTGCTGCTGTGCGAGCTGCCCCACCCTGCCTTTCTGCTGATCCCCGAGAAGTCCGAC
CTGCGGACAGTGGCCCCTGCCAGCTCTCTGAACGTGCGCTTCGACAGCCGGACCATGAACCTGAGCTGGGACTGC
CAGGAAAACACAACCTTCAGCAAGTGCTTCCTGACCGACAAGAAAACCGGGTGGTGGAACCCCGGCTGAGCAA
CAACGAGTGCTCCTGCACCTTTAGAGAGATCTGCCTGCACGAGGGCGTGACCTTCGAGGTGCACGTGAACACCAG
CCAGCGGGGCTTCCAGCAGAAGCTGCTGTACCCCAACAGCGGCAGAGAGGGAACAGCCGCCCAGAACTTCAGCT
GCTTCATCTACAACGCCGACCTGATGAACTGCACCTGGGCCAGAGGACCTACCGCCCCAGAGATGTGCAGTACTT
CCTGTACATCCGGAACAGCAAGCGGCGGAGAGAAATCCGGTGCCCATACTATATCCAGGACAGCGGCACACACGT
GGGCTGCCACCTGGATAATCTGAGCGGCCTGACCAGCCGGAACTACTTCCTCGTGAACGGCACCAGCAGAGAGAT
CGGCATCCAGTTCTTCGACTCCCTGCTGGACACCAAGAAGATCGAGCGGTTCAACCCCCCCAGCAACGTGACCGTG
CGGTGCAATACCACCCACTGCCTCGTGCGGTGGAAGCAGCCCAGAACCTACCAGAAGCTGAGCTACCTGGACTTC
CAGTACCAGCTGGACGTGCACCGGAAGAACACCCAGCCCGGCACCGAGAACCTGCTGATCAACGTGTCCGGCGAC
CTGGAAAACAGATACAACTTCCCCAGCAGCGAGCCCAGAGCCAAGCACAGCGTGAAGATCAGAGCCGCCGACGT
GCGGATCCTGAACTGGTCCTCTTGGAGCGAGGCCATCGAGTTCGGCAGCGACGATGGCAATCTGGGCAGCGTGT
ACATCTACGTGCTGCTGATTGTGGGCACCCTCGTGTGCGGAATCGTGCTGGGCTTCCTGTTCAAGCGGTTCCTGCG
GATCCAGAGACTGTTCCCCCCAGTGCCCCAAATCAAGGACAAGCTGAACGACAACCACGAGGTGGAAGATGAGAT
CATCTGGGAGGAATTCACCCCCGAGGAAGGCAAGGGCTACCGGGAAGAGGTGCTGACCGTGAAAGAGATCACCT
```

Fig. 19B

```
GAGTCGACGGATCCCCCGGGCTGCAGGAATTCGAGCATCTTACCGCCATTTATACCCATATTTGTTCTGTTTTTCTT
GATTTGGGTATACATTTAAATGTTAATAAAACAAAATGGTGGGGCAATCATTTACATTTTTAGGGATATGTAATTAC
TAGTTCAGGTGTATTGCCACAAGACAAACATGTTAAGAAACTTTCCCGTTATTTACGCTCTGTTCCTGTTAATCAAC
CTCTGGATTACAAAATTTGTGAAAGATTGACTGATATTCTTAACTATGTTGCTCCTTTTACGCTGTGTGGATATGCT
GCTTTAATGCCTCTGTATCATGCTATTGCTTCCCGTACGGCTTTCGTTTTCTCCTCCTTGTATAAATCCTGGTTGCTGT
CTCTTTATGAGGAGTTGTGGCCCGTTGTCCGTCAACGTGGCGTGGTGTGCTCTGTGTTTGCTGACGCAACCCCCAC
TGGCTGGGGCATTGCCACCACCTGTCAACTCCTTTCTGGGACTTTCGCTTTCCCCCTCCCGATCGCCACGGCAGAAC
TCATCGCCGCCTGCCTTGCCCGCTGCTGGACAGGGGCTAGGTTGCTGGGCACTGATAATTCCGTGGTGTTGTCGG
GGAAGCTGACGTCCTTTCGAATTCGATATCAAGCTGTACCTTTAAGACCAATGACTTACAAGGCAGCTGTAGATCT
TAGCCACTTTTTAAAAGAAAAGGGGGGACTGGAAGGGCTAATTCACTCCCAACGAAGACAAGATCTGCTTTTTGCT
TGTACTGGGTCTCTCTGGTTAGACCAGATCTGAGCCTGGGAGCTCTCTGGCTAACTAGGGAACCCACTGCTTAAGC
CTCAATAAAGCTTGCCTTGAGTGCTTCAAGTAGTGTGTGCCCGTCTGTTGTGTGACTCTGGTAACTAGAGATCCCTC
AGACCCTTTTAGTCAGTGTGGAAAATCTCTAGCAGTAGTAGTTCATGTCATCTTATTATTCAGTATTTATAACTTGCA
AAGAAATGAATATCAGAGAGTGAGAGGAACTTGTTTATTGCAGCTTATAATGGTTACAAATAAAGCAATAGCATC
ACAAATTTCACAAATAAAGCATTTTTTTCACTGCATTCTAGTTGTGGTTTGTCCAAACTCATCAATGTATCTTATCAT
GTCTGGCTCTAGCTATCCCGCCCCTAACTCCGCCCAGTTCCGCCCATTCTCCGCCCCATGGCTGACTAATTTTTTTA
TTTATGCAGAGGCCGAGGCCGCCTCGGCCTCTGAGCTATTCCAGAAGTAGTGAGGAGGCTTTTTGGAGGCCTAG
GCTTTTGCGTCGAGACGTACCCAATTCGCCCTATAGTGAGTCGTATTACGCGCGCTCACTGGCCGTCGTTTTACAAC
GTCGTGACTGGGAAAACCCTGGCGTTACCCAACTTAATCGCCTTGCAGCACATCCCCCTTTCGCCAGCTGGCGTAA
TAGCGAAGAGGCCCGCACCGATCGCCCTTCCCAACAGTTGCGCAGCCTGAATGGCGAATGGCGCGACGCGCCCTG
TAGCGGCGCATTAAGCGCGGCGGGTGTGGTGGTTACGCGCAGCGTGACCGCTACACTTGCCAGCGCCCTAGCGCC
CGCTCCTTTCGCTTTCTTCCCTTCCTTTCTCGCCACGTTCGCCGGCTTTCCCCGTCAAGCTCTAAATCGGGGGCTCCC
TTTAGGGTTCCGATTTAGTGCTTTACGGCACCTCGACCCCAAAAAACTTGATTAGGGTGATGGTTCACGTAGTGGG
CCATCGCCCTGATAGACGGTTTTTCGCCCTTTGACGTTGGAGTCCACGTTCTTTAATAGTGGACTCTTGTTCCAAAC
TGGAACAACACTCAACCCTATCTCGGTCTATTCTTTTGATTTATAAGGGATTTTGCCGATTTCGGCCTATTGGTTAAA
AAATGAGCTGATTTAACAAAAATTTAACGCGAATTTTAACAAAATATTAACGTTTACAATTTCCCAGGTGGCACTTT
TCGGGGAAATGTGCGCGGAACCCCTATTTGTTTATTTTTCTAAATACATTCAAATATGTATCCGCTCATGAGACAAT
AACCCTGATAAATGCTTCAATAATATTGAAAAAGGAAGAGTATGAGTATTCAACATTTCCGTGTCGCCCTTATTCCC
TTTTTTGCGGCATTTTGCCTTCCTGTTTTTGCTCACCCAGAAACGCTGGTGAAAGTAAAAGATGCTGAAGATCAGTT
GGGTGCACGAGTGGGTTACATCGAACTGGATCTCAACAGCGGTAAGATCCTTGAGAGTTTTCGCCCCGAAGAACG
TTTTCCAATGATGAGCACTTTTAAAGTTCTGCTATGTGGCGCGGTATTATCCCGTATTGACGCCGGGCAAGAGCAA
CTCGGTCGCCGCATACACTATTCTCAGAATGACTTGGTTGAGTACTCACCAGTCACAGAAAAGCATCTTACGGATG
GCATGACAGTAAGAGAATTATGCAGTGCTGCCATAACCATGAGTGATAACACTGCGGCCAACTTACTTCTGACAAC
GATCGGAGGACCGAAGGAGCTAACCGCTTTTTTGCACAACATGGGGGATCATGTAACTCGCCTTGATCGTTGGGA
ACCGGAGCTGAATGAAGCCATACCAAACGACGAGCGTGACACCACGATGCCTGTAGCAATGGCAACAACGTTGC
GCAAACTATTAACTGGCGAACTACTTACTCTAGCTTCCCGGCAACAATTAATAGACTGGATGGAGGCGGATAAAGT
TGCAGGACCACTTCTGCGCTCGGCCCTTCCGGCTGGCTGGTTTATTGCTGATAAATCTGGAGCCGGTGAGCGTGG
GTCTCGCGGTATCATTGCAGCACTGGGGCCAGATGGTAAGCCCTCCCGTATCGTAGTTATCTACACGACGGGGAG
TCAGGCAACTATGGATGAACGAAATAGACAGATCGCTGAGATAGGTGCCTCACTGATTAAGCATTGGTAACTGTC
AGACCAAGTTTACTCATATATACTTTAGATTGATTTAAAACTTCATTTTTAATTTAAAAGGATCTAGGTGAAGATCCT
TTTTGATAATCTCATGACCAAAATCCCTTAACGTGAGTTTTCGTTCCACTGAGCGTCAGACCCCGTAGAAAAGATCA
AAGGATCTTCTTGAGATCCTTTTTTTCTGCGCGTAATCTGCTGCTTGCAAACAAAAAAACCACCGCTACCAGCGGTG
GTTTGTTTGCCGGATCAAGAGCTACCAACTCTTTTTCCGAAGGTAACTGGCTTCAGCAGAGCGCAGATACCAAATA
CTGTCCTTCTAGTGTAGCCGTAGTTAGGCCACCACTTCAAGAACTCTGTAGCACCGCCTACATACCTCGCTCTGCTA
```

Fig. 19C

```
ATCCTGTTACCAGTGGCTGCTGCCAGTGGCGATAAGTCGTGTCTTACCGGGTTGGACTCAAGACGATAGTTACCGG
ATAAGGCGCAGCGGTCGGGCTGAACGGGGGGTTCGTGCACACAGCCCAGCTTGGAGCGAACGACCTACACCGAA
CTGAGATACCTACAGCGTGAGCTATGAGAAAGCGCCACGCTTCCCGAAGGGAGAAAGGCGGACAGGTATCCGGT
AAGCGGCAGGGTCGGAACAGGAGAGCGCACGAGGGAGCTTCCAGGGGGAAACGCCTGGTATCTTTATAGTCCTG
TCGGGTTTCGCCACCTCTGACTTGAGCGTCGATTTTTGTGATGCTCGTCAGGGGGGCGGAGCCTATGGAAAAACG
CCAGCAACGCGGCCTTTTTACGGTTCCTGGCCTTTTGCTGGCCTTTTGCTCACATGTTCTTTCCTGCGTTATCCCCTG
ATTCTGTGGATAACCGTATTACCGCCTTTGAGTGAGCTGATACCGCTCGCCGCAGCCGAACGACCGAGCGCAGCG
AGTCAGTGAGCGAGGAAGCGGAAGAGCGCCCAATACGCAAACCGCCTCTCCCCGCGCGTTGGCCGATTCATTAAT
GCAGCTGGCACGACAGGTTTCCCGACTGGAAAGCGGGCAGTGAGCGCAACGCAATTAATGTGAGTTAGCTCACTC
ATTAGGCACCCCAGGCTTTACACTTTATGCTTCCGGCTCGTATGTTGTGTGGAATTGTGAGCGGATAACAATTTCAC
ACAGGAAACAGCTATGACCATGATTACGCCAAGCGCGCAATTAACCCTCACTAAAGGGAACAAAAGCTGGAGCTG
CAAGCTTAATGTAGTCTTATGCAATACTCTTGTAGTCTTGCAACATGGTAACGATGAGTTAGCAACATGCCTTACAA
GGAGAGAAAAGCACCGTGCATG
```

CELL THERAPY WITH LENTIVIRAL TRANSDUCED CSF2RA TRANSGENE IN THE TREATMENT OF HEREDITARY PULMONARY ALVEOLAR PROTEINOSIS

CROSS-REFERENCE TO RELATED APPLICATIONS

This application is a national stage entry, filed under 35 U.S.C. § 371, of International Application No. PCT/US2018/032933, filed on May 16, 2018, and claims the benefit of and priority to U.S. Provisional Patent Application No. 62/507,399, filed May 17, 2017, the entire contents of which is hereby incorporated herein by reference in its entirety and for all purposes.

STATEMENT REGARDING FEDERALLY SPONSORED RESEARCH

This invention was made with government support under HL106134 and HL118342 awarded by the National Institutes of Health. The U.S. Government has certain rights in the invention.

INCORPORATION BY REFERENCE OF SEQUENCE LISTING

The present application contains a Sequence listing in ASCII format. The ASCII copy, created on Nov. 12, 2019, is named 047108-533N01US_Sequence_Listing_ST25.txt and is 11,178 bytes in size, the content of which is hereby incorporated by reference in its entirety.

FIELD OF THE INVENTION

The disclosure relates to compositions and methods for personalized cell therapy of hereditary pulmonary alveolar proteinosis in humans.

BACKGROUND OF THE INVENTION

Hereditary pulmonary alveolar proteinosis (hPAP) is a rare and chronic life-threatening lung disease characterized by hypoxemic respiratory failure caused by alveolar surfactant accumulation. The presentation, pathogenesis and diagnosis of hPAP was first defined by studies of hPAP in two sisters with CSF2RA mutations followed by the identification of a cohort of patients with hPAP caused by mutations in the CSF2RA or CSF2RB genes. Suzuki T et al., *J Exp Med* 2008 205:2703-10; Martinez-Moczygemba M et al., *J Exp Med* 2008 205:2711-6; Suzuki T et al., *Am J Resp Crit Care Med* 2010 182:1292-304; Suzuki T et al., *Eur Resp J* 2011 37:201-217.

Hereditary PAP is caused by homozygous or compound-heterozygous mutations in the genes coding for the heterodimeric granulocyte/macrophage-colony stimulating factor receptor (CSF2R), a high-affinity receptor complex composed of an alpha-subunit (CSF2RA, CD116) conferring GM-CSF specificity and the common beta-subunit (CSF2RB, CD131), which is shared with the receptors for IL-3 and IL-5. Upon binding of granulocyte/macrophage-colony stimulating factor (GM-CSF) to the receptor, CSF2RB activates intracellular signaling by JAK2 kinases. Without GM-CSF stimulation, alveolar macrophages (AMs) have a reduced capacity to clear surfactant, which accumulates in alveoli and results in displacement of inhaled air, a thickened diffusional barrier, and reduced oxygen delivery into the blood. Mutations in either subunit result in similar disease manifestations and natural history. Presentation of hPAP typically occurs in childhood after 1.5 years of age and before adolescence. Symptoms at clinical presentation include dyspnea of insidious onset and lung infection. In the identified cohort of hPAP patients the disease-specific mortality is 8.3%. Formal mortality and epidemiological studies have not been completed due to the recent characterization of hPAP in humans and its prevalence and natural history is currently under study.

The only currently available therapy for hPAP is whole lung lavage (WLL)—a procedure done under general anesthesia in which one lung is mechanically ventilated while the other is filled with saline, the chest is percussed to emulsify surfactant lipids into the saline, which is drained to physically remove surfactant and the whole process repeated multiple times on the same lung and then applied to the opposite lung. WLL is inefficient, associated with morbidity from general anesthesia and tracheal abrasion caused by prolonged intubation of both main-stem bronchi, mechanical ventilation, as well as from the repeated filling and draining of the lung with saline. Some hPAP patients require treatments every 1 or 2 months. WLL is not available at most adult centers and is rarely available at pediatric centers. There is a strong need for alternative therapies for hPAP that are safer and more efficient in treating the manifestations of the disease.

Allogeneic bone marrow transplantation (BMT) is the treatment of choice for several other life-threatening congenital diseases such as those affecting the lympho-hematopoietic system. However, BMT is highly problematic in hPAP patients due to severe pre-existing lung damage. The pulmonary damage accompanying hPAP interferes with adequate chemo- and/or radiotherapeutic conditioning prior to transplantation and puts patients at risk of overwhelming infections.

As an alternative to allogeneic BMT, autologous hematopoietic stem cell gene therapy has been proposed. In the Csf2rb$^{-/-}$ mouse model and in in vitro studies, genetic correction of hematopoietic stem/progenitor cells (HSPCs) using a LTR-driven gamma-retroviral vector was able to restore the function of hematopoietic cells. Kleff et al. *Mol. Ther.* 2008 16(4):757-764. However, hematopoietic stem cell gene therapy in humans would most likely also require some degree of chemo- and/or radio-therapeutic conditioning.

Several studies have evaluated cell therapy in chronic lung diseases including silicosis, idiopathic pulmonary fibrosis, and emphysema. BMC Pub Med 2015 5:1-8; NCT01872624 (2015); NCT02745184 (2016). In these studies, the potentially therapeutic autologous bone marrow-derived or lung-derived cells were instilled directly into the lungs. None of these studies utilized genetically modified cells.

No studies to date have evaluated direct lung transplantation of genetically modified patient autologous macrophage cells in humans. Pulmonary macrophage transplantation using either wild type or Csf2rb gene corrected macrophage cells was shown to be well tolerated and effective in reducing the manifestations of disease in the Csf2rb mouse model of hPAP. Suzuki T et al, *Nature* 2014 514:450-4.

The potential for adverse events due to insertional mutagenesis with γ-retroviral vectors (γ-RV) has been reported in patients with X-linked severe combined immunodeficiency, Wiskott Aldrich Syndrome and chronic granulomatous disease. In all cases, γ-RV insertions near transcription start sites (TSS) of proto-oncogenes led to their activation by enhancer elements in the vector long-terminal repeat (LTR) regions and transformed cell clones subsequently progressed to malignancy.

The clinical experience with LV vectors, although in its infancy, has not met with the same complications. However, emergence of clonal dominance from gene-modified human stem cells due to dysregulation of the HMGA2 gene in a β-thalassemia patient treated with a β-globin LV was observed. The primary limitation controlling the emergence of insertional mutants is believed to be associated with the proliferation potential and self-renewal capacity of the effector cell. Cell therapy in humans with virally transduced transgenes remains an area of active research aimed at increasing the efficacy of transgene expression while reducing the risk of adverse events related to use of the viral vector.

The present disclosure addresses the need for new therapeutic methods for treating hPAP in humans that are safe and effective compared to the standard of care, WLL.

SUMMARY OF THE INVENTION

The present invention provides compositions and methods relating to cell therapy for hPAP in human patients using gene corrected and in vitro differentiated patient autologous macrophage cells. The disclosure provides compositions in the form of a cell product comprising the gene corrected and in vitro differentiated patient autologous macrophage cells and related compositions for transplantation as well as additional compositions and methods for making and using the cell product, including intermediate cell and viral products.

In embodiments, the disclosure provides a self-inactivating lentiviral vector comprising a human CSF2RA cDNA. In embodiments, the human CSF2RA cDNA is generated based on the sequence designated NM_006140. In embodiments, the human CSF2RA cDNA is codon-optimized. In embodiments, the codon-optimized human CSF2RA cDNA comprises or consists of SEQ ID NO:1, or a sequence having 95-99% sequence identity to SEQ ID NO:1, provided that any change at the nucleotide level does not constitute a change in the amino acid sequence encoded by the cDNA of SEQ ID NO:1. In embodiments, the expression of the human CSF2RA cDNA is under the control of a human elongation factor 1-alpha short promoter (EFS). In embodiments, the vector further comprises a woodchuck hepatitis post-transcriptional regulatory element (wPRE). In embodiments, the wPRE sequence is detectable by polymerase chain reaction amplification using a set of forward and reverse primers identified by SEQ ID NOs:2 and 3. In embodiments, the vector further comprises a lentiviral polypurine tract. In embodiments, the vector envelope psuedo-type is VSV-G.

In embodiments, the disclosure also provides a composition comprising a self-inactivating lentiviral vector encoding a human CSF2RA cDNA as described herein, and a carrier, and optionally further comprising from one to three additional viral plasmids selected from a VSV-G envelope plasmid, a gag/pol plasmid, and a rev plasmid, for use in transducing human bone marrow derived CD34+ hematopoietic stem/progenitor cells.

In embodiments, the disclosure also provides a composition comprising virions containing a self-inactivating lentiviral vector encoding a human CSF2RA cDNA as described herein, and a carrier, optionally wherein the composition contains from about 5×10e7 virions per ml or is characterized by an infectious titer of from about 1 to 5×10e8 IU/ml.

In embodiments, the disclosure also provides a composition comprising human bone marrow derived CD34+ hematopoietic stem/progenitor cells transduced with a self-inactivating lentiviral vector encoding a human CSF2RA cDNA as described herein, and a carrier, optionally further comprising a cryopreservation excipient.

In embodiments, the disclosure also provides a composition comprising non-naturally occurring in vitro differentiated human macrophage cells derived from CD34+ cells transduced with a self-inactivating lentiviral vector encoding a human CSF2RA cDNA as described herein, the macrophage cells comprising a lentiviral transgene encoding a human CSF2RA cDNA, and a carrier, optionally further comprising a cryopreservation excipient. In embodiments, the composition comprises less than 2% CD34+ cells and greater than 70% CD11+ cells. In embodiments, the composition is sterile. In embodiments, the composition contains from about 2-20×10e6 cells/ml. In embodiments, the macrophage cells are autologous to a human subject having pulmonary alveolar proteinosis (hPAP).

In accordance with any of the embodiments of compositions comprising a carrier, the carrier may be selected from an aqueous solution buffered to physiological pH, saline or other physiologically buffered salt solution, or a cell culture medium, preferably a serum free medium supplemented with human serum albumin.

In embodiments, the disclosure also provides a cell freeze bag or cryovial comprising the non-naturally occurring in vitro differentiated human macrophage cells derived from CD34+ cells transduced with a self-inactivating lentiviral vector encoding a human CSF2RA cDNA as described herein.

In embodiments, the disclosure also provides a cell freeze bag or cryovial comprising human bone marrow derived CD34+ hematopoietic stem/progenitor cells transduced with a self-inactivating lentiviral vector encoding a human CSF2RA cDNA, as described herein.

The compositions described here are useful for treating pulmonary alveolar proteinosis (hPAP) in a human subject in need thereof. Accordingly, the disclosure further provides methods for treating hPAP in a human subject in need thereof, utilizing the cell based compositions described here. In embodiments, the methods comprise administering a therapeutic amount of non-naturally occurring in vitro differentiated human macrophage cells derived from CD34+ cells transduced with a self-inactivating lentiviral vector encoding a human CSF2RA cDNA as described herein, to a lung segment of the subject, preferably to a plurality of lung segments, and most preferably to each lung segment, wherein the CD34+ cells are obtained from the subject. In embodiments, human macrophage cells, or a composition comprising same, is administered by direct instillation to individual lung segments of the subject. In embodiments, the administration is through a flexible fiberoptic bronchoscope. In embodiments, the therapeutic amount is a dose of from about 5 to 6×10e5 cells per lung segment per kilogram weight of the subject. In embodiments, the therapeutic amount is a cumulative cell dose of from about 400 to 800×10e6 cells, or from about 500 to 600×10e6 cells, or from about 600 to 700×10e6 cells, or from about 700 to 800×10e6 cells, for a 70 kg human subject. In embodiments, the cumulative cell dose is achieved over three separate administrations of the cell product, separated in time by 30 or 60 days, or by about 2 months, such that following the third administration every segment of both lungs of the subject have been received the cell product.

The disclosure also provides methods for producing gene corrected human macrophage cells for use in treating hPAP in a human subject in need thereof, and compositions comprising the cells made according to the methods described here. In embodiments, the method comprises

- isolating CD34+ hematopoietic progenitor cells from a mononuclear cell enriched fraction of human bone marrow,
- culturing the cells for about 8-12 hours in medium comprising stem cell factor (SCF), thrombopoietin, Flt3-ligand, interleukin-6, interleukin-3, granulocyte macrophage colony stimulating factor (GM-CSF), and macrophage colony stimulating factor (M-CSF),
- transducing the CD34+ cells with the lentiviral vector of any one of claims 1-6,
- culturing the transduced cells for about 5-6 days in medium optimized to promote cell growth to provide an expanded population of transduced CD34+ cells,
- culturing the expanded CD34+ cells in a three stage culture system for about an additional 14-15 days to obtain gene corrected human macrophage cells, wherein during this period of time the concentrations of recombinant stem cell cytokines are gradually decreased while the concentrations of myeloid differentiation cytokines, recombinant MCSF and GM-CSF, are simultaneously increased to favor production of macrophages, and optionally cryopreserving the gene corrected human macrophage cells.

The disclosure further provides methods for therapeutic monitoring of a cell therapy in the treatment of hPAP in a human subject in need thereof. In embodiments, the methods comprise determining a baseline disease severity for the subject to be treated, said baseline being determined before the initiation of the cell therapy, and determining a disease severity at one or more time points following initiation of the cell therapy, wherein disease severity is determined by a method comprising measuring the turbidity of one or a plurality of fluid samples obtained from the patient's lungs, and wherein a reduction in disease severity relative to baseline indicates that the cell therapy is having a positive effect, while no change or an increase in disease severity relative to baseline indicates that the cell therapy is ineffective. In embodiments, the methods may further comprise adjusting the dose of the cells where the cell therapy is ineffective. In embodiments, the dose is adjusted by increasing the number of cells administered and/or by adding a further administration step to the cell therapy protocol.

The disclosure further provides genetically modified murine alveolar macrophage cells. In embodiments, the disclosure provides a genetically modified murine alveolar macrophage cell line lacking the murine CSF2RA and RB genes transduced to express a human GM-CSF receptor alpha and beta chain. In embodiments, the disclosure provides a genetically modified murine alveolar macrophage cell line lacking the murine CSF2RA and RB genes transduced to express an aberrant human GM-CSF receptor alpha chain carrying a G to A point mutation in exon 7. In embodiments, the disclosure further provides for a further genetic modification of the murine alveolar macrophage cell line transduced to express the aberrant human GM-CSF receptor alpha chain, wherein the further geneic modification consists of transduction to express a functional human GM-CSF receptor alpha chain.

BRIEF DESCRIPTION OF THE FIGURES

FIG. 10A-I: Transduction of primary human CD34+ cells and in vitro differentiation of transduced cells into macrophage. (a) Analysis of hCD116 expression in primary CD34$^+$ cells, transduced with Lv.EFS.CSF2RA$^{coop}$ (grey), Lv.EFS.GFP (light grey), or mock treated cells (black). (b) Proliferation of transduced CD34+ cells as determined by dilution of eFluor670. Mean fluorescent intensity values of e670 are normalized to time zero. (c) Total colony numbers per 1500 input cells cultivated in methylcellulose containing human SCF, GM-CSF, IL-3 and Epo for 7-10 days. (d) Representative pictures of clonogenic cells observed after 7-10 days in methylcellulose based assays. (e) Increase in overall cell number during differentiation of Lv.EFS.CSF2RA$^{coop}$ (triangle), Lv.EFS.GFP (inverted triangle), or mock treated cells (square) towards macrophages for 14 days in the presence of IL3, IL6, FLT3, M-CSF, and GM-CSF. (f) Representative bright field images of macrophages on day 14 of differentiation. (g) Phenotypic analysis of macrophages on day 14 of differentiation by flow cytometry. Histograms are shown as overlays of mock treated, Lv.EFS.CSF2RA$^{coop}$, and Lv.EFS.GFP. (h) Functional analysis of transduced macrophages in the presence of hGM-CSF. Histograms show phosphorylation of STAT5 in the absence (grey) or presence (black) of hGM-CSF. (i) Relative amount of pSTAT5 after stimulation of transduced macrophages with hGM-CSF. Values are calculated and normalized to non-stimulated conditions.

FIG. 11A-J: Validation of Csf2ra$^{KO}$ mice as a clinically relevant model of human hPAP. (a) Genomic DNA PCR of each genotype mouse (WT)+/+, heterozygous+/−, homozygous−/−). (b) Photomicrographs of bronchoalveolar lavage (BAL) fluid from 10-week old mice of WT and Csf2ra$^{KO}$ mice. (c, d) BAL turbidity is increased in 10-week old Csf2ra$^{KO}$ mice and showed age-dependent progression compared to age-matched WT mice. (e) Immunofluorescent staining for CD116 of alveolar macrophages from WT and Csf2ra$^{KO}$ mice. (f) Oil-red-0 staining of cytospin slides of BAL cells from WT and Csf2ra$^{KO}$ mice. (g) Lung histology of WT and Csf2ra$^{KO}$ mice. (h j) BAL levels of total cholesterol (h), GM-CSF (i), and M-CSF (j) were also increased significantly in 10-week old Csf2ra$^{KO}$ mice but not age-matched WT mice.

FIG. 12A-H: Engraftment and therapeutic efficacy of PMT of congenic wildtype macrophages in Csf2raKO mice. (a) Immunofluorescent staining of CD116 of alveolar macrophages obtained from Csf2ra$^{KO}$ mice 2 months after PMT. (b) Flow cytometry analysis show the presence of CD116$^+$ cells in PMT treated mice. (c) Oil-Red-O staining of cytospin slides of bronchoalveolar lavage (BAL) cells. (d) Photomicrographs of BAL fluid from mice of wildtype, untreated Csf2ra$^{KO}$, and Csf2ra$^{KO}$ with PMT therapy. (e-g) hPAP biomarkers of BAL fluid. Turbidity (e), total cholesterol (f), GM-CSF, M-CSF, and MCP-1 (g) were significantly reduced in Csf2ra$^{KO}$ mice 2 months after PMT compared to untreated mice. (h) Time course of BAL turbidity in untreated Csf2ra$^{KO}$ mouse (top line on graph) showed age-dependent progression, which was improved by 2 months and 6 months post single PMT therapy. *p<0.05.

FIG. 15A-D: hGM-Rα-LV restores GM-CSF receptor function in in vitro models of hPAP using genetically modified human HEK293 cells as well as murine mAM-hPAP cells. (a) viral copy number (VCN) dependent CD116 expression from hGM-Rα LV transduced mAM-hPAP cell line (b) Mean fluorescence intensity (MFI) of CD116 expression in transduced mAM-hPAP and HEK-hPAP cell lines (c) Phosphorylated STAT5 expression after GM-CSF stimulation in HEK-hPAP cells (d) GM-CSF clearance assay.

FIG. 19A-C: Sequence of the codon optimized human CSF2RA cDNA designated SEQ ID NO:1.

DETAILED DESCRIPTION OF THE INVENTION

The present disclosure provides compositions and methods relating to personalized cell therapy for treating hPAP in human patients. In embodiments, the disclosure provides a cell product for transplantation in humans comprising non-naturally occurring in vitro differentiated patient autologous macrophage cells expressing a lentiviral transduced CSF2RA transgene. The disclosure also provides methods for producing the cell product, including methods for obtaining bone marrow aspirates and isolating patient autologous CD34$^+$ cells therefrom, transducing the CD34$^+$ cells with a lentiviral CSF2RA transgene, and expanding and differentiating the transduced cells into macrophage cells. Also provided are methods for pulmonary macrophage transplantation ("PMT") for administering the cell product directly to a patient's lungs. PMT is based on direct pulmonary instillation of the cell product into the lungs without the need for any prior pulmonary niche making (e.g., myeloablation) or immunosuppression.

The present invention is based, in part, on work by the present inventors following their initial characterization of hPAP. This work pointed to mutations in the alpha chain of CSF2R (CD116) as accounting for the vast majority of mutations in human hereditary PAP patients. For example, 22 out of a cohort of 36 individuals with hereditary PAP carried mutations in CD116, while only two carried mutations in the beta chain (CD131), which was the focus of prior pre-clinical work. In accordance with this discovery, the present disclosure provides compositions and methods for cell therapy of hPAP in humans utilizing pulmonary macrophage transplantation (PMT) of patient autologous gene-corrected macrophage cells. In this context, "gene-corrected" refers to the cells carrying a functional CSF2RA transgene.

The disclosure provides various compositions comprising, for example, the lentiviral expression vectors described here, CD34+ cells transduced with a lentiviral vector described here, virions containing a lentiviral vector described here, and patient autologous macrophage cells expressing the lentiviral transduced CSF2RA transgene ("the cell product"). In accordance with these embodiments, the composition may further comprise a suitable carrier such as an aqueous solution buffered to a neutral pH, saline or other buffered salt solution, or a cell culture medium, preferably a serum free medium supplemented with human serum albumin. Exemplary cell culture media are known in the art and described below. In embodiments, the carrier may be a cryopreservation medium, which may contain a suitable excipient such as dimethylsulfoxide (DMSO).

The terms 'human subject' and 'patient' are used interchangeably herein.

Overview of Cell Therapy for hPAP in Humans

Figure 1:
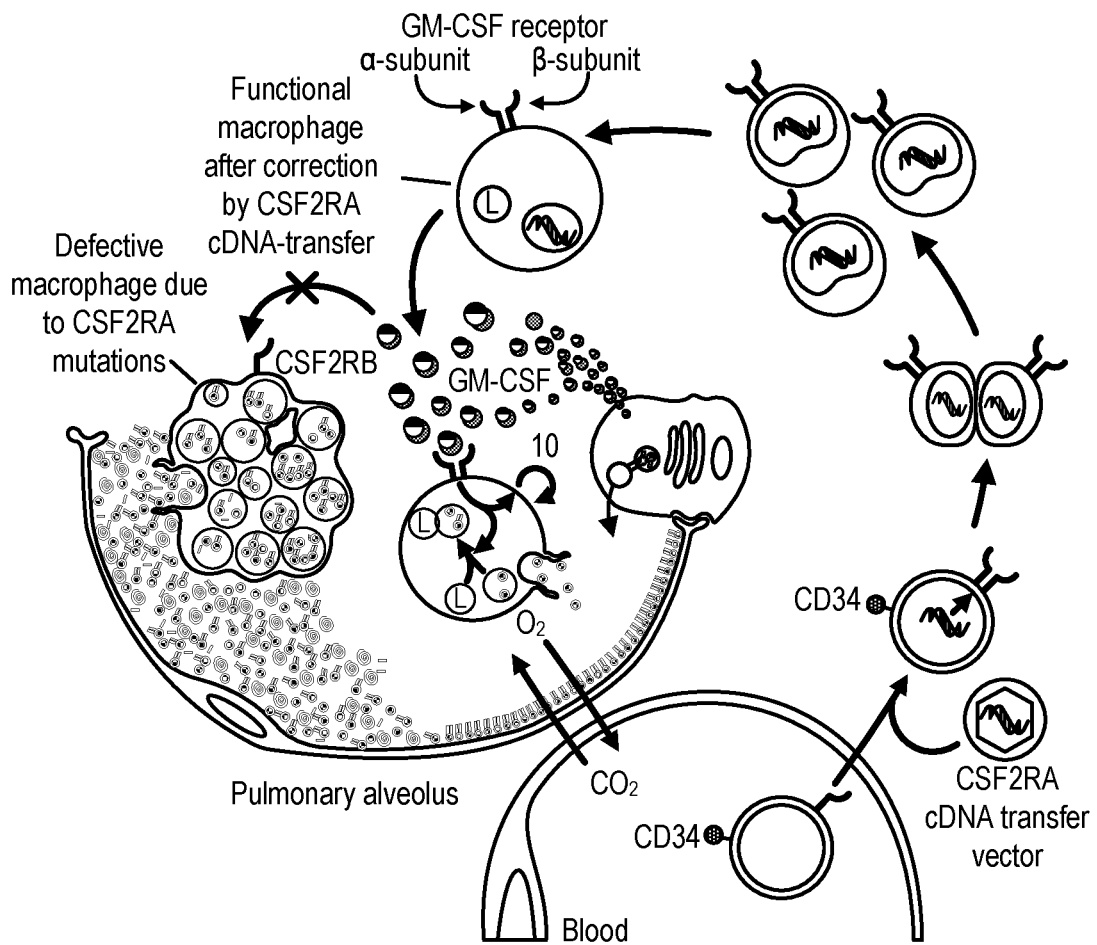
FIG. 1: Schematic illustration of the therapeutic approach.

FIG. 1 shows a schematic illustration of the therapeutic approach. In hPAP, GM-CSF receptor dysfunction blocks GM-CSF signaling to alveolar macrophages (AMs) thereby reducing clearance of surfactant, which accumulates in AMs and alveoli, displaces air and reduces oxygen (O2) uptake. In this approach, bone marrow-derived hematopoietic stem/progenitor cells (CD34+ cells in humans, LSK cells in mice) are isolated, transduced with a GM-CSF receptor (GM-R) cDNA expressing lentiviral vector to restore GM-R expression and responsiveness to GM-CSF, cryopreserved until needed then thawed (not shown), expanded, differentiated into macrophages, and administered by direct instillation into lung segments using a standard flexible fiberoptic bronchoscope. In patients with hPAP caused by CSF2RA (or CSF2RB) mutations, increased levels of pulmonary GM-CSF confer a selective survival advantage to the gene-corrected macrophage cells, which proliferate, engraft, replace endogenous dysfunctional AMs (without prior myeloablation), clear excess accumulated surfactant from alveoli, reestablish alveolar surfactant homeostasis, and restore lung function.

Lentiviral Vectors, Related Compositions, and Methods of Production

The disclosure provides self-inactivating lentiviral plasmid expression vectors and related compositions and methods for their production and use in transducing cells to express a human CSF2RA transgene.

In embodiments, the disclosure provides a self-inactivating lentiviral vector for transducing human bone marrow derived hematopoietic stem/progenitor cells (e.g., CD34+ cells) with a human CSF2RA cDNA, compositions comprising the vector, compositions comprising the transduced cells, and compositions comprising virions containing the vector. In this context, "self-inactivating" refers to a vector having a deletion in the U3 region encompassing the long terminal repeat. This feature effectively eliminates viral transcriptional regulatory elements.

Figure 2:
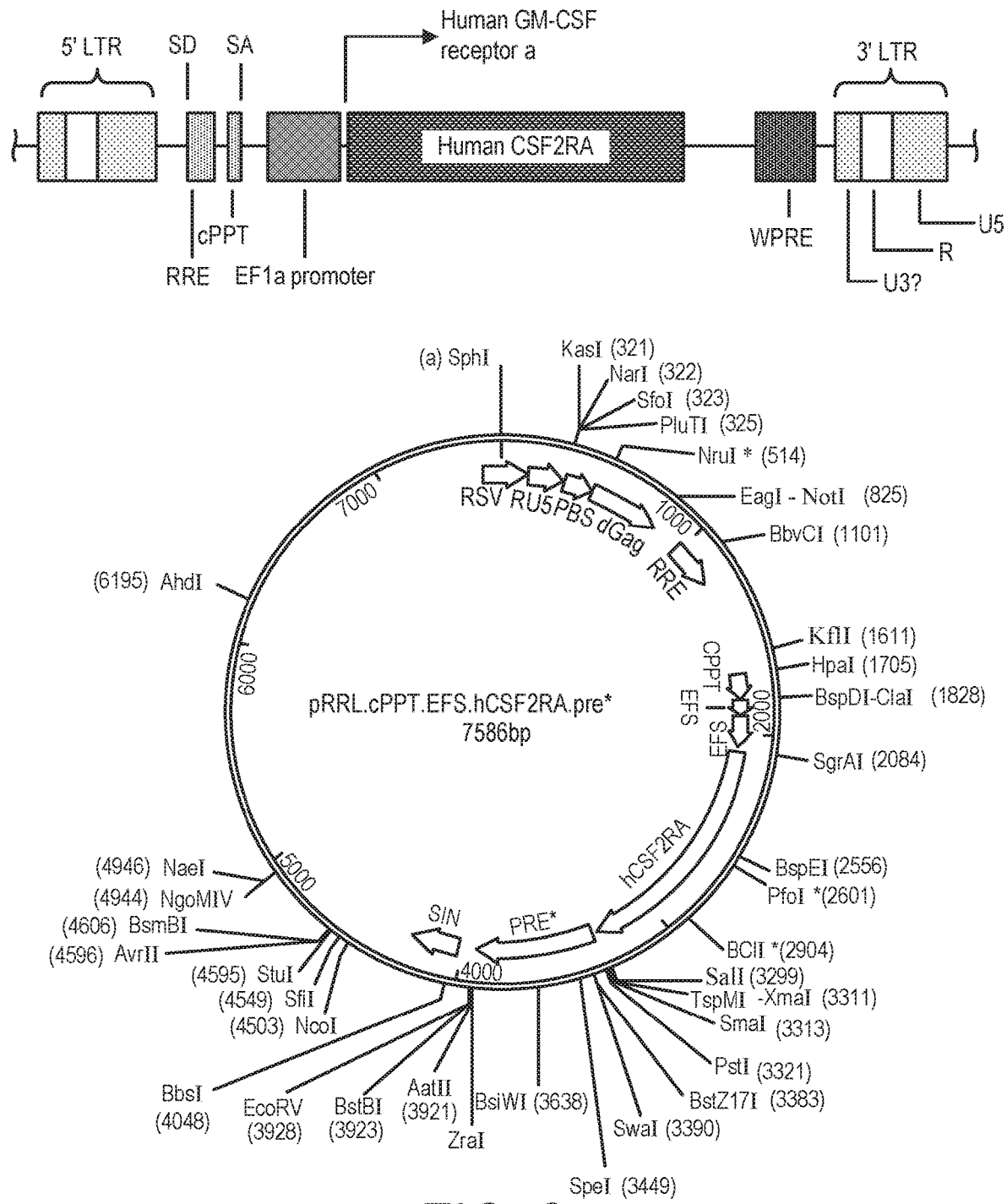
FIG. 2: Proviral schematic and vector plasmid map for hGM-Rα-LV.

In embodiments, the disclosure provides a self-inactivating lentiviral plasmid expression vector is suitable for transducing human bone marrow derived hematopoietic stem/progenitor cells (e.g., CD34+ cells) with a human CSF2RA cDNA. In embodiments, this vector is the vector designated hGM-Rα-LV or Lv.EFS.CSF2RA$^{coop}$. These are two designations referring to the same vector. This vector may also be referred to as "the clinical vector". A proviral schematic and vector map for the clinical lentiviral vector, hGM-Rα-LV or Lv.EFS.CSF2RA$^{coop}$, is shown in FIG. 2.

Figure 3:
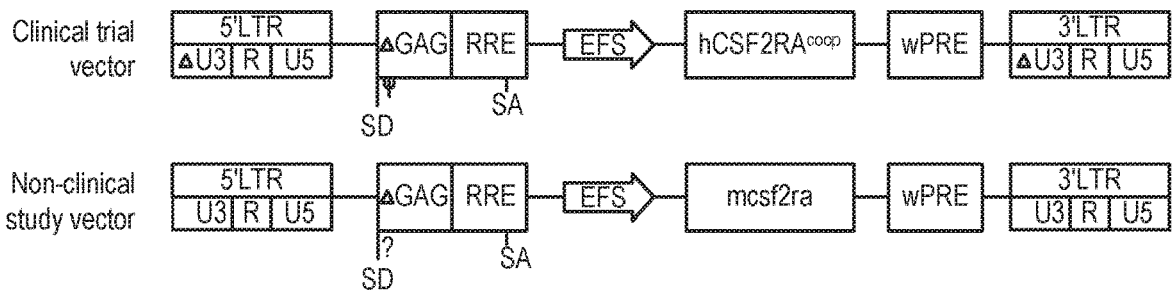
FIG. 3: Comparison of proposed vectors for use in the non-clinical and clinical studies.

In embodiments, the disclosure provides a self-inactivating lentiviral plasmid expression vector is suitable for transducing murine bone marrow derived hematopoietic stem/progenitor cells (e.g., LSK cells) with a murine Csf2ra cDNA. This vector may be referred to interchangeably as the "murine vector" or as the "non-clinical" vector. FIG. 3 shows a schematic of the clinical vector and the murine (non-clinical) vector aligned for comparison. Both vectors are constructed with the same lentiviral vector backbone expression plasmid and have the same overall structural organization, differing only by the sequences of their respective transgenes in order to target expression of functional GM-CSF receptor alpha (α) chains to the desired species. The U3 region of the 3' long terminal repeats (LTR) contains a 400 bp deletion of the promoter enhancer, to allow self-inactivating (SIN) design, to facilitate absence of viral transcriptional elements upon integration into the host cells. The 5' HIV U3 region is replaced with respiratory syncytial virus (RSV) promoter enhancer. Other safety features include use of a weak physiological promoter to drive the transgene expression and the inclusion of the woodchuck hepatitis virus posttranscriptional response element (wPRE) to enhance transcript termination.

In embodiments, the human CSF2RA cDNA of the clinical vector is generated from the sequence designated NM_006140, *Homo sapiens* colony stimulating factor 2 receptor, alpha subunit (CSF2RA), see Gene ID 1438 (updated Apr. 8, 2018) for detailed information. In embodiments, the human CSF2RA cDNA of the clinical vector is codon optimized. In embodiments, the codon optimized human CSF2RA cDNA of the clinical vector comprises or consists of the sequence identified by SEQ ID NO:1. In embodiments, the human CSF2RA cDNA of the clinical vector comprises or consists of a sequence that is 95-99% identical to the sequence designated SEQ ID NO:1, or 90-95% identical to the sequence designated SEQ ID NO:1, provided that any differences in sequence identity do not result in an amino acid change in the encoded CSF2R alpha chain such that the amino acid sequence is the same as that encoded by SEQ ID NO:1. Also provided are sets of forward and reverse primers for amplifying the lentiviral transduced cDNA from transduced cells in a polymerase chain reaction, for example in order to determine viral copy number (VCN) of the transduced cells. Exemplary primers targeted to vector sequences flanking the transgene are provided in the table below. SEQ ID Nos 2 and 3 are targeted to the wPRE sequence and SEQ ID Nos 2 and 3 are targeted to the PTBP2 sequence.

TABLE 1

SEQ ID Nos 1-5

| No. | Name | Sequence |
|---|---|---|
| 1 | CSF2RA cDNA | See FIG. 19 |
| 2 | wPRE Fwd | GAGGAGTTGTGGCCCGTTGT |
| 3 | wPRE Rev | TGACAGGTGGTGGCAATGCC |
| 4 | PTBP2 Fwd | TCTCCATTCCCTATGTTCATGC |
| 5 | PTBP2 Rev | GTTCCCGCAGAATGGTGAGGTG |

In embodiments, the disclosure also provides methods for making infectious virions containing a self-inactivating lentiviral plasmid expression vectors described here, as well as methods for making gene corrected cells by transduction. In embodiments, the lentiviral vector supernatant is produced by transient transfection of a suitable cell line, for example 293T cells, with the clinical lentiviral vector, i.e., a human CSF2RA lentivirus expression vector, and three viral plasmids, a rev plasmid, a gag/pol plasmid and a VSV-G envelope plasmid.

The clinical lentiviral vector for use in the methods of treating human hPAP patients described here is preferably manufactured under suitable conditions for human use, for example in an ISO class 7 cleanroom and ISO class 5 BSCs in compliance with regulations governing early phase GMP manufacture. In embodiments, the lentiviral vector supernatant may be produced by transient transfection using a certified 293T working cell bank. In embodiments, the reagents and materials used to produce the clinical lentiviral vector meet predefined specifications including investigation new drug (IND) ready grade plasmids.

In an exemplary embodiment for purposes of illustration, the virions containing the clinical lentiviral vector are produced by the following method. 293T cells are transiently transfected with the hCSF2RA lentivirus expression vector and three viral plasmids—a VSV-G envelope plasmid, a gag/pol plasmid, and a rev plasmid, followed by benzonase treatment to generate approximately 60 liters of unprocessed supernatant from 2 harvests collected at approximately 2 and 3 days post transfection. The supernatant material is clarified through a series of filters, exposed to ion-exchange chromatography, concentrated, and diafiltered using tangential flow filtration. Aliquots of the supernatant may be cryopreserved in serum free medium supplemented with 2% human serum albumin and stored at ≤−65° C. until use. Accordingly, in embodiments, the disclosure provides a composition comprising the infectious virions. In embodiments, the composition comprises about 5×10e7 virions per ml. In embodiments, the composition is characterized by an infectious titer of from about 1-5×10e8 IU/ml.

In embodiments, end of production (EOP) cells and vector supernatant from appropriate phases are tested for purity, potency, and identity. Such tests may include one or more of the following assays: assays for sterility, e.g., using aerobic and anaerobic culture for bacteria and fungus; endotoxin screening assays; analysis for the presence of replication competent virus e.g., by testing for amplification on a permissive cell line; *mycoplasma* screening assays, e.g., by staining indicator cells with a fluorochrome; screening for the presence of adventitious viruses (before purification of the vector); screening for residual benzonase; assaying transgene stability, e.g., by Southern analysis; assay for residual cellular DNA; assays for the presence of SV40 and/or adenovirus E1a, e.g., by exposing cells to the vector followed by culturing for 14 days, isolating total cellular DNA and quantitative PCR to detect and quantify adenovirus SV40 and E1a DNA; STAT5 phosphorylation.

The Cell Product, Related Products, and Methods of Production

The disclosure also provides a cell product in the form of non-naturally occurring in vitro differentiated patient autologous human macrophage cells derived from patient autologous CD34+ cells transduced with the clinical vector. The cell product may be designated "hGM-Rα+MΦ" to indicate that the cells are of a macrophage lineage ("MO") and that the cells contain a transgene encoding the human granulocyte/macrophage-colony stimulating factor receptor alpha subunit, CSF2RA ("hGM-Rα"). The "+" indicates that the cells encode a functional CSF2RA, which may distinguish the cell product from a patient's endogenous macrophage cells, for example, where the patient's endogenous macrophage cells carry one or more inactivating mutations in CSF2RA.

The cell product of the present disclosure is derived from lentiviral transduced CD34+ cells obtained from human bone marrow, for example, from the bone marrow of a patient to be treated according to the methods described here. In this context, "derived from" refers to the process by which the macrophage cells are in vitro differentiated from lentiviral transduced CD34+ cells as described infra. In embodiments, the disclosure provides patient autologous gene corrected macrophage cells for transplantation derived from lentiviral transduced CD34+ cells carrying a CSF2RA transgene, and compositions comprising same. In embodiments, the disclosure provides a composition comprising the patient autologous gene corrected macrophage cells, and a carrier, wherein the carrier comprises a cryopreservation excipient such as dimethyl sulfoxide (DMSO).

The disclosure also provides related compositions, including for example patient autologous CD34+ cells transduced with the clinical vector, which are produced as an intermediate in the production of the cell product. The CD34+ cells may also be referred to as bone marrow derived CD34+ progenitor cells or bone marrow-derived hematopoietic stem/progenitor cells. As described below, the CD34+ cells are enriched from a population of nucleated cells obtained from bone marrow aspirates of the patient. In embodiments, the disclosure provides a composition comprising lentiviral transduced CD34+ cells carrying a CSF2RA transgene, and a carrier, wherein the carrier comprises a cryopreservation excipient such as dimethyl sulfoxide (DMSO). The disclosure also provides methods for making such cells, the methods comprising obtaining patient autologous bone marrow derived cells, enriching for mononuclear cells, and further selecting CD34+ cells, for example using flow cytometry, to obtain a population of patient autologous bone marrow derived CD34+ cells.

In an exemplary embodiment for purposes of illustration the CD34+ cell composition may be produced according to a protocol comprising obtaining patient autologous bone marrow derived CD34+ cells from bone marrow aspirates. In embodiments, the aspirates may be collected from both posterior iliac crests into heparinized syringes and transferred to a sterile bone marrow harvest bag containing preservative-free heparin. In embodiments, the maximum amount collected is about 20 mL/kg as determined by a board-certified hematologist. This amount should typically provide a total yield of about 2×10e8 nucleated cells which will give about 2-4×10e6 CD34+ cells, per kg of body weight. In embodiments, the method may further comprise steps of filtering the aspirate to remove clots and bone spicules, for example through a series of inline filters of 500 microns through 170 microns into a suitable transfer bag. In embodiments, the method may further comprise steps of enriching for mononuclear cells. Mononuclear cell enrichment may be performed according to standard methods, for example, using the Neatcell™ protocol and a SEPAX 2 RM automated cell processor according to the manufacturer's protocols, or similar technique. The method may further comprise a step of isolating CD34+ hematopoietic progenitor cells from the enriched mononuclear cell fraction. This may also be performed according to standard methods, for example by labeling the mononuclear cells with a detectable label, for example the CliniMACS® CD34 reagent, followed by an appropriate selection method based on the label chosen, for example using a CliniMACS® Instrument, or similar technique, according to the manufacturer's protocols. At this stage the CD34+ cells may optionally be cryopreserved using standard methods for cryopreservation of human cells. These may include, for example, the addition of a cryopreservation reagent, such as dimethyl sulfoxide (DMSO), prior to freezing.

The disclosure also provides methods for making the cell product from the patient autologous CD34 cells. In embodiments, the methods comprise transducing autologous CD34+ hematopoietic progenitor cells isolated from the patient's bone marrow, for example as described above, with a CSF2RA expressing lentiviral vector, e.g., the clinical vector, hGM-Rα-LV, followed by expansion and differentiation into macrophage cells. In embodiments, the transduced cells may be cryopreserved following expansion but prior to differentiation into macrophage cells. Accordingly, in another embodiment the disclosure provides a composition comprising CD34+ cells transduced with the clinical vector a CSF2RA expressing lentiviral vector, e.g., the clinical vector, hGM-Rα-LV, optionally comprising a cryopreservation reagent such as dimethyl sulfoxide (DMSO).

In an exemplary embodiment of the expansion and differentiation protocol, freshly collected or thawed transduced CD34+ cells are prestimulated overnight on retronectin coated plates (available, e.g., from manufacturers such as Takara) in serum-free X-VIVO™ 10 media containing 2% human serum albumin supplemented with the following recombinant human cytokines: 300 ng/mL stem cell factor (SCF); 300 ng/mL thrombopoietin; 100 ng/mL Flt3-ligand; 10 ng/mL interleukin-6; 10 ng/mL interleukin-3; 10 ng/mL granulocyte macrophage colony stimulating factor (GM-CSF); and 20 ng/mL macrophage colony stimulating factor (M-CSF). The following day, cells are transduced with the hGM-Rα LV at a concentration of 1×10e7 to 2.5×10e7 cells, twice at 12±2 hours apart. Cells are washed the following day and portions of the hGM-Rα+MΦs plated in methylcellulose medium for colony-forming assays (CFU-C) and placed in progenitor expansion medium in liquid unilineage myeloid cultures.

The strategy for expansion and differentiation of CD34+ cells into mature macrophages described here achieves a 2-3 log increase in cell number during the initial expansion phase. Briefly, the macrophage differentiation protocol employs a three stage culture system where the concentrations of recombinant stem cell cytokines are gradually decreased during differentiation phase, while the concentrations of macrophage cytokines, recombinant MCSF and GM-CSF, are simultaneously increased to favor production of macrophages. Over 3 weeks, CD34 levels decrease (from 98% to <1%) in parallel with increases in CD11b (>80%), CD14 (>50%), and cell adherence, thus indicating macrophage differentiation.

Figure 4:
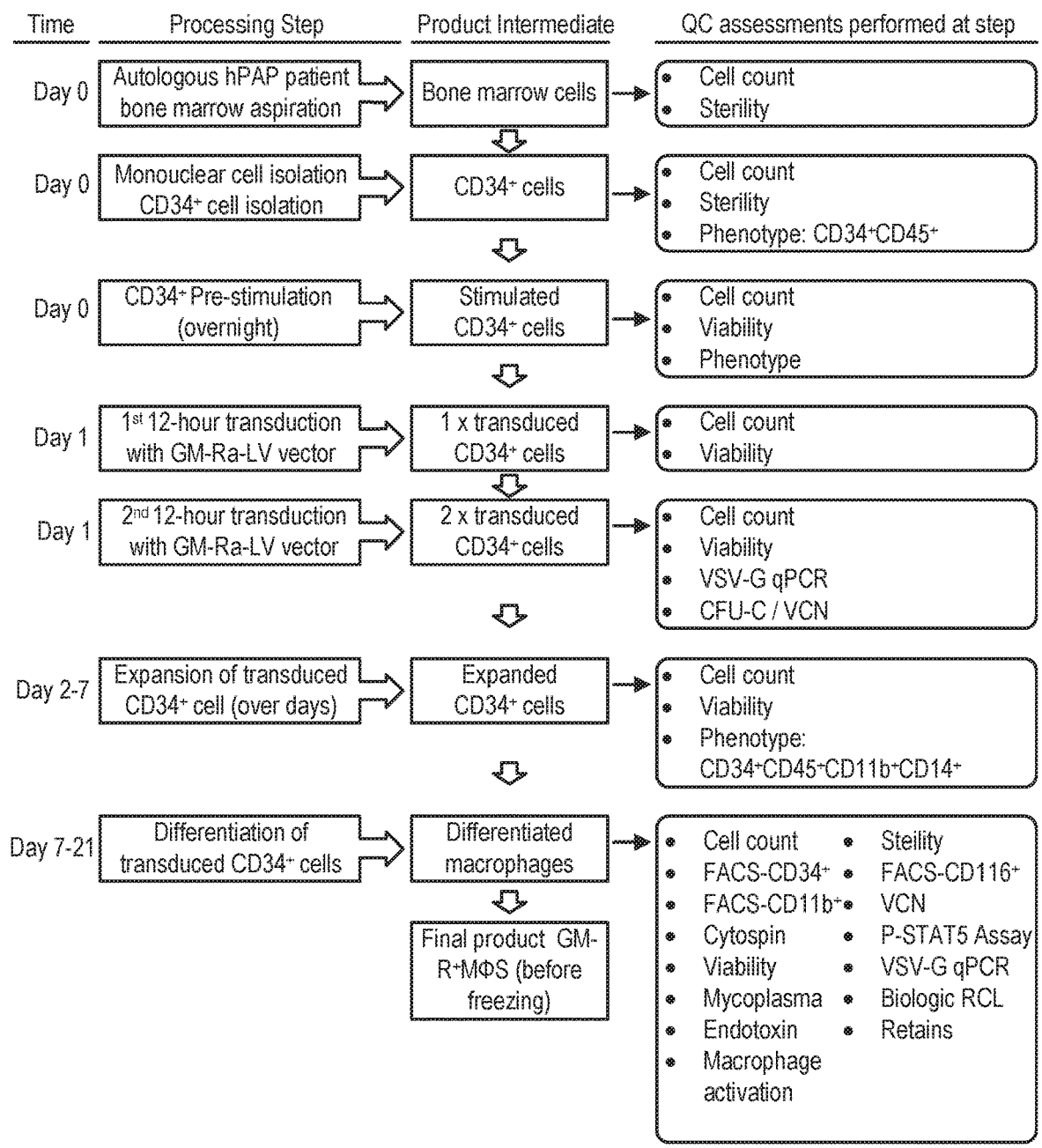
FIG. 4: Summary of cell processing up to cryopreservation. VCN: Vector Copy number, RCL: Replication competent lentivirus, CFU-C: Colony forming units culture, VSV-G qPCR: vesicular stomatitis virus glycoprotein quantitative polymerase chain reaction.

FIG. 4 shows a summary of exemplary cell processing steps up to cryopreservation (Day 0 to Day 21), including the product intermediate obtained at each step and the quality control (QC) testing that is preferably performed at each step. For example, samples may be assayed for cell number, viability, sterility, phenotype, cell morphology, and gene transfer at specific stages of the culture.

Using the macrophage generation protocol described here, a 150-200 fold expansion of adherent hGM-Rα+MDs is typically obtained on day 21. Additional scale-up for macrophage production may include use of a closed bioreactor system, for example the Xpansion Multiplate Bioreactor (MPB) is a single use bioreactor system (Pall Life Sciences). In embodiments, the adherent macrophages obtained are characterized and tested for quality assurance including, for example, testing for one or more, or all, of the following: number of viable cells, e.g., by cell counting; percentage of CD34+ and CD11b+ cells, e.g., by flow cytometry, viability, e.g., by vital dye exclusion assay, microbial contamination, e.g., by *mycoplasma* assay, gram stain, etc.; endotoxin contamination, e.g., by LAL assay, macrophage activation, e.g., by ELISA for detection of TNFα compared to a control of INFγ titration curve and/or by a phospho-STAT5 assay; transgene expression, e.g., by assaying for CD116+ cells by flow cytometry; assays to detect replication competent lentivirus (RCL).

In embodiments, transduced macrophages are further processed by cryopreservation. The cryopreservation and post thaw recovery of transduced macrophages is preferably optimized to retain maximal viability and functionality. In addition, preferably the stability of the cells is evaluated through verification of viability, functionality and quality over a pre-determined timeframe and simulation of cellular delivery. The cell product is preferably stable following cryopreservation in a controlled rate freezer and storage in the vapor phase of liquid nitrogen at <−140° C. for at least 45 days. In a preferred embodiment, the cell product is placed in a cryopreservation bag, for example a Charter Medical Cell-Freeze® bag, preferably with a sterile overwrap.

Figure 5:
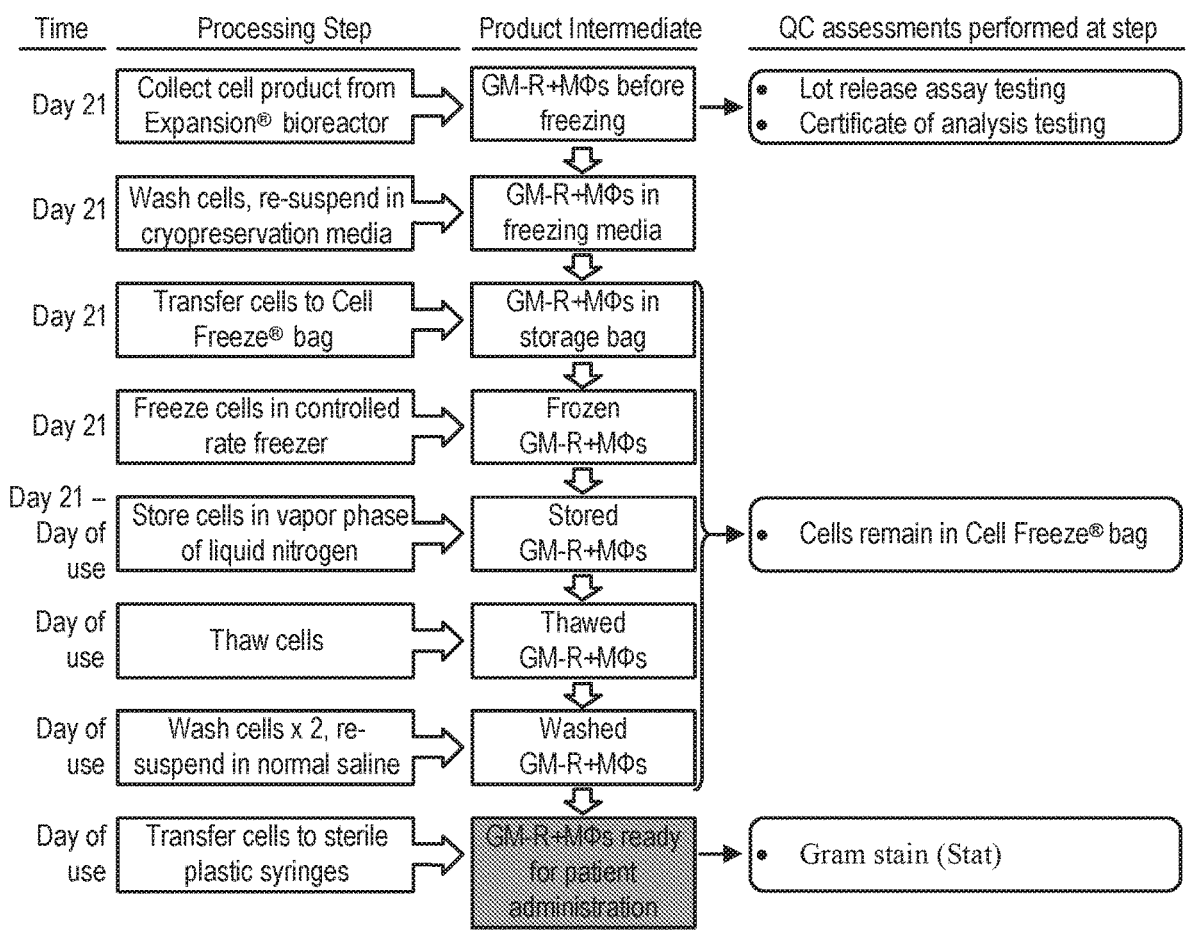
FIG. 5: Summary of cell processing steps related to cryopreservation, thawing, and preparation for administration.
Figure 6A:
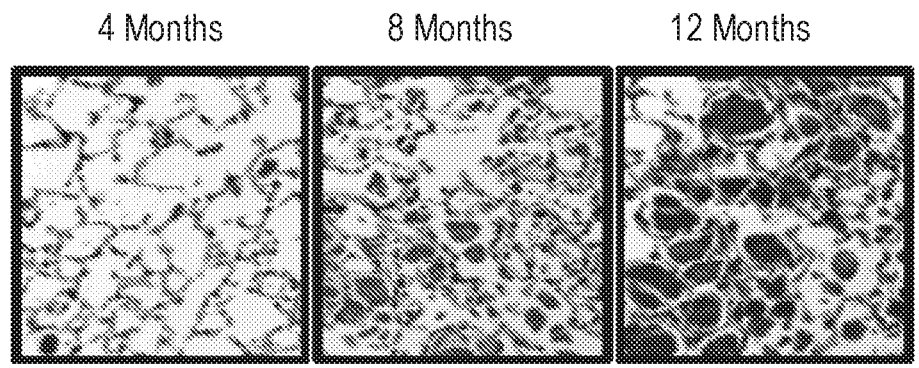
FIG. 6A-E: Experimental basis for measuring hPAP disease severity using bronchoalveolar lavage (BAL) turbidity. A, Lung histopathology. B, Lung histopathology score. C. BAL turbidity in mice. D. WLL fluid turbidity in humans. E. A turbidity-based disease severity index (T-DSI) for PAP.
Figure 6B:
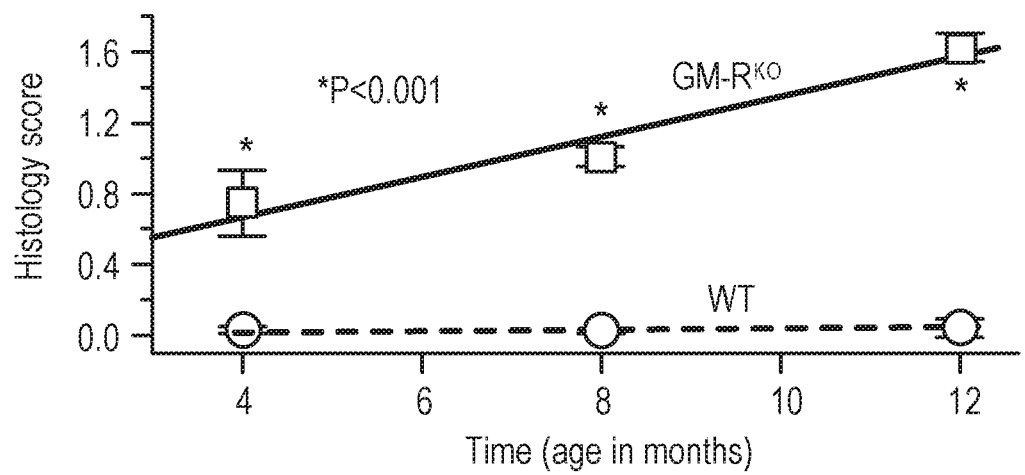
Figure 6C:
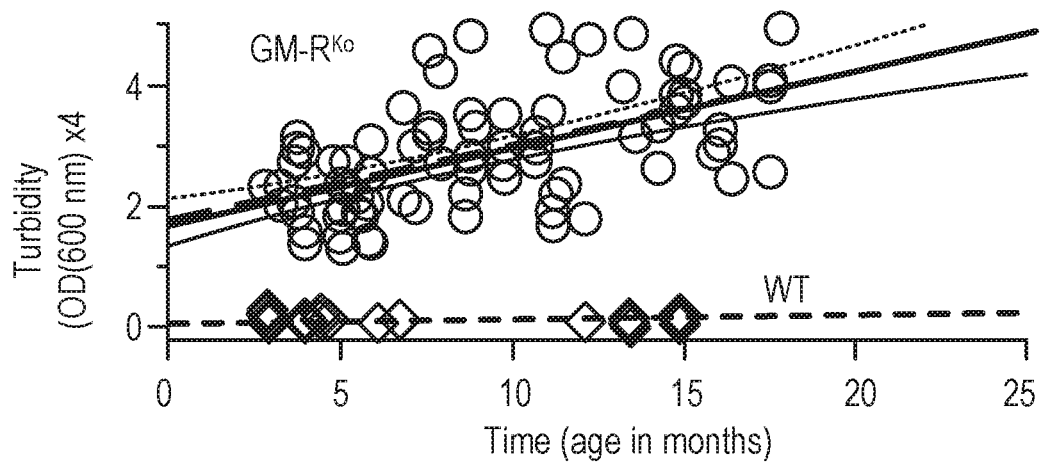
Figure 6D:
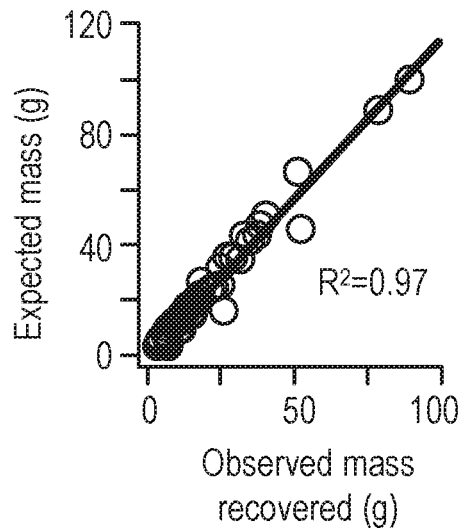
Figure 6E:
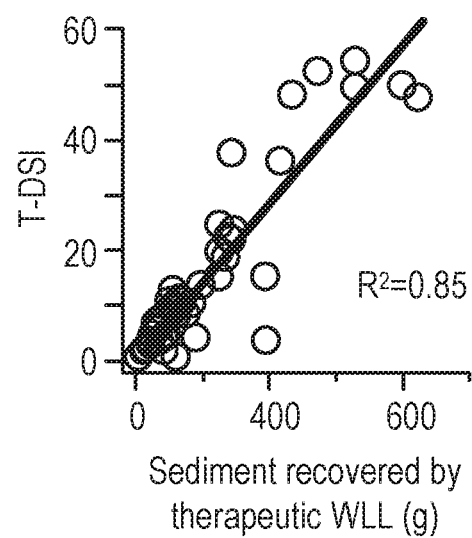

FIG. 5 shows a summary of exemplary cell processing steps related to cryopreservation, thawing, and preparation of the cell product for administration. hGM-Rα+MΦs are collected from the bioreactor on day 21, washed, supernatant removed and macrophage cell pellet re-suspended in a cryopreservation medium such as CryoStor™ medium at concentrations between 2-20×10e6 cells/mL then transferred into a cryopreservation bag such as a Charter Medical Cell-Freeze® using a syringe. Cryopreservation is initiated in a controlled rate freezer and after 24 hours the bag is transferred to a liquid nitrogen cryogenic freezer for long-term storage. On the day of transplantation, the bag is thawed, washed twice to remove DMSO and resuspended in an appropriate volume of saline for cell counting and loading into a syringe for administration to the product. Preferably, a small portion of the final product is tested for sterility by Gram stain before administration.

Preferably, all manipulation of cellular material obtained from patients is performed in an ISO class 7 cleanroom and ISO class 5 BSCs in compliance with regulations governing early phase GMP manufacture.

Administration and Dosing of the Cell Product

The disclosure also provides methods for administering the cell product to a human patient in need thereof, for example a patient in need of treatment for hPAP. In embodiments, the methods comprise administering the cell product to the lungs, preferably via direct instillation into individual lung segments, for example during routine bronchoscopy under conscious sedation.

In an exemplary embodiment for purposes of illustration, the patient receives the cell product via a 10-ml fluid bolus delivered during routine bronchoscopy into individual lung segments in three escalating doses administered at three different times over a four month period, e.g. at 0, 2, and 4 months. As discussed infra, the present inventors have shown that there is a linear dose-response relationship between dose (the number of cells administered) and therapeutic response (as measured by reduction in disease severity using the turbidity based disease severity index (T-DSI) described below). The cell doses for administration to humans according to the methods described here are based upon this work. In an exemplary embodiment, the doses are 1) 0.45×10e6 cells/kg in one lung segment for the first dose; 2) 2.31×10e6 cells/kg in one lobe (divided among 4 lung segments) for the second dose; and 3) 8.1×10e6 into the remaining untreated lung (divided among all untreated segments) for the last dose.

In order to arrive at the therapeutic doses described here for administration to human patients, dose-ranging studies were conducted in the murine Csf2rb$^{KO}$ model using the ratio between humans and mice for each of several parameters including: 1) body weight, 2) numbers of alveolar macrophages, 3) numbers of alveoli, 4) alveolar surface area, 5) relative respiratory rate, and 6) replacement of the number of alveolar macrophages normally present in the lungs. Each cell dose estimate was compared to the total number of alveolar macrophage in healthy, non-smoking adult humans. Assumptions used in calculating cell doses included the following: 1) body weight (adult)=70 kg (human) and 25 g (mouse); 2) number of alveoli per individual=480×10e6 (human), 4.2×10e6 (mouse); 3) alveolar surface area per individual=130±12 m$^2$ (human), 82.2 cm$^2$ (mouse); 4) number of alveolar macrophage per individual=5×10e9 (human), 1.3×10e6 (mouse); 5) human lungs (both) contain a total of 19 segments (assume all are of equal size); 6) murine alveolar deposited dose (MDD %)=50% of the cell dose administered to mice by intratracheal instillation; 7) human alveolar deposited dose (HDD %)=90% of the cell dose administered to humans by bronchoscopy; 8) two months after PMT will be an appropriate time to evaluate therapeutic efficacy of PMT therapy of hPAP.

From this work, relative body weight was chosen as the parameter to obtain the human dose. Thus, in preferred embodiments, the dose is based on relative body weight. In accordance with this embodiment, the number of cells comprising a full cell dose, i.e., to treat all lung segments in a human patient, is calculated as: Human dose=murine dose×(human weight÷mouse weight)×(MDD %÷HDD %), where murine dose was either the minimum effective dose, the standard dose, or the maximum dose evaluated in Csf2rb$^{KO}$ mice. The standard dose in mice (0.5×10e6 cells/mouse) is defined as the lowest cell dose with therapeutic efficacy equivalent to all higher doses in mice evaluated two months after PMT. The equivalent dose in humans is 11×10e6 cells/kg, which represents 16% of the AM population in a 70 kg adult human.

In embodiments, each subject receives a total number of cells (~770×10e6—representing the numbers of cells summed over all three administrations) equivalent to the standard dose in mice divided into three separate doses with an escalating number of cells in each dose. The number of cells (5.78×10e5) delivered to each segment of each lobe of each lung is held constant. Escalation is achieved by increasing the number of lung segments receiving instilled cells during each administration. In an exemplary embodiment for illustration, this may be performed as follows: First administration, delivered into one lung segment of the right middle lobe-lateral; Second administration, delivered into four basal lung segments of right lower lobe; Third administration, delivered into all remaining non-treated lung segments of the right and left lungs. The lung segment dose is calculated as: Lung segment dose=total human dose÷number of lung segments in the patient. For example, for a 70 kg person with 19 lung segments, the total cell dose is 798 million cells, and the lung segment dose is the 798 million cells divided 19 segments is equal to 42 million cells per segment.

In an exemplary specific embodiment, the cell product is suspended in normal saline and administered by instillation into individual lung segments through the suction port of a flexible fiberoptic bronchoscope. The first administration may comprise one lung segment dose delivered into one segment of one lobe (right middle lobe—lateral segment). The second administration may comprise a total of four lung segment doses delivered into one lobe, the basilar segments of the right lower lobe segment. The third administration may comprise the remainder of the total cell dose, i.e., the sum of lung segment doses minus the treated lung segment doses, delivered into each of the remaining non-treated lung segments. These doses are lower than the dose equivalent to the maximum dose evaluated in mice and provide minimum estimates of the safety margin for PMT at each dose level. In embodiments, each administration occurs at two monthly intervals.

In embodiments, the cumulative cell dose is from about 400-800×10e6 cells, or from about 500-600×10e6 cells, or from about 600-700×10e6 cells, or from about 700-800×10e6 cells, for a 70 kg human subject.

In a further exemplary specific embodiment of the administration procedure, the patient undergoes routine conscious sedation, topical anesthesia of the nasal, oral, and pharyngeal mucosa, placement of an intravenous line, and continuous monitoring of vital signs and SpO2. A standard flexible bronchoscope is inserted through one nostril (or mouth), passed through the vocal cords, and a bronchoscopic examination of the airways with collection of epithelial lining fluid (ELF) by bronchoalveolar lavage (BAL) is performed. In embodiments, a blood specimen is also collected at the time of BAL to permit calculation of concentration of biomarkers.

An exemplary detailed procedure for the first administration is described here for purposes of illustration. The patient is positioned so that the lung to be treated is in a dependent position, e.g., a right lateral position would be used for administration to the right middle lobe. The bronchoscope is passed down the trachea, into the right main-stem bronchus, and into the right middle lobe and the bronchoscope positioned with its tip 2 cm beyond the meatus of the lateral segment. The investigational product is drawn up into a sterile plastic syringe with additional air above the liquid. While directly observing to ensure the bronchoscope tip remains correctly positioned, the syringe plunger is pushed at moderate speed to deliver the fluid and cells over ~30-40 seconds followed by an air bolus to ensure complete delivery of the fluid into the lung segment subtended by the wedged bronchoscope tip. The patient then remains in the right lateral position for 5 minutes and the bronchoscope will remain positioned in the right main-stem bronchus without use of suction to observe that the fluid remains in the segment. The patient is then be positioned in a right lateral supine position for 10 minutes and monitored for 2 hours or as long as necessary in the recovery room as per routine procedure.

In embodiments, a patent in need of treatment according to the methods described here is one having hPAP caused by CSF2R deficiency. In embodiments, the CSF2R deficiency is a CSF2RA deficiency. In embodiments, the patient is a pediatric patient, defined as one less than 18 years of age. In embodiments, the patient is from 10 to 18 years old or from 12 to 18 years old.

Therapeutic Monitoring of Cell Therapy

The disclosure also provides methods for monitoring the efficacy of the cell therapy described herein. The methods comprise determining a patient's hPAP disease severity at a first time point before initiation of the cell therapy to establish a baseline, followed by measuring the disease severity at one or more time points following the initiation of cell therapy to determine whether the disease severity is increasing or decreasing. For example, in embodiments disease severity is determined at 2-3 month intervals during the first 12-16 months following administration of the first dose of the cell product. In embodiments, disease severity is determined at 2 months following initiation of cell therapy, and optionally at one or more of 4, 6, 8, and 12 months. An improvement in disease severity relative to baseline indicates that the cell therapy is having a positive effect. The lack of an improvement may indicate the need to alter the therapeutic regimen, for example by administering a further or higher dose of the cell product.

In embodiments, disease severity is determined by a method comprising measuring the turbidity of a fluid sample from the patient's lungs. In embodiments, turbidity is measured as the optical density of a fluid sample at 600 nm. In embodiments, the fluid sample is obtained by bronchoalveolar lavage (BAL) or whole lung lavage (WLL). In embodiments, multiple fluid samples are obtained from the lavage procedure and the method comprises determining a turbidity based disease severity index (T-DSI) calculated as the sum of the volume-weighted turbidities of all of the samples.

FIG. 6A-E shows the experimental basis for determining hPAP disease severity based on turbidity as described above. Panel A illustrates the histopathology of periodic-acid-Schiff (PAS) staining of lung tissue, a 'gold standard' in PAP assessment, showing a progressive accumulation of surfactant in GM-R$^{KO}$ mice. Lungs were inflation-fixed and PAS stained by standard methods. In panel B, a lung histology score based on visual scoring of PAS staining is shown. The score was higher in GM-R$^{KO}$ than WT mice at all times evaluated and was higher at each successively older age in GM-R$^{KO}$ mice but unchanged in WT mice (ANOVA/Holm-Sidak; 3 mice/group/time point; *=P<0.001). The histology score was determined using 5 inflation-fixed, 6 μm lung sections/mouse (3 mice/group at each age). One field (20×) from each section (identified by random-number coordinates) was photographed and superimposed with a 130 box grid. Only boxes completely overlying lung were counted and boxes containing bronchioles and large vessels were excluded. The tissue in each box was assessed for surfactant accumulation (i.e., PAS staining; 0=none, 1=mild, 2=moderate, 3=severe). For each section, the number of boxes at each grade was multiplied by the numeric value of the grade. This product—for all grades from each of the 5 sections—was added and divided by the number of boxes counted to yield the histology score for each mouse.

In panel C, BAL turbidity is shown to increase with time in GM-R$^{KO}$ mice (linear regression, f=0.031±0.005x+1.73; f=turbidity, x=months; P<0.0001) but not WT mice (similar analysis). Each symbol=one mouse. Regression lines and 95% CI are shown. BAL (5×1 ml aliquots) was obtained and turbidity was determined as the optical absorbance at 600 nm and multiplied by the dilution factor (four).

Panel D shows the analysis of WLL fluid turbidity in humans. An extinction coefficient for PAP surfactant sediment (8.049±0.245 (SEM)) was determined from 135 consecutive bags of human WLL (see below) and used to calculate the amount of surfactant (Expected mass) in the next 76 bags of WLL, which was compared to the actual amount recovered (Observed mass). WLL fluid was evaluated immediately after collection during therapeutic procedures in PAP patients. After measuring the volume of WLL fluid, bags were mixed to ensure homogenous suspension and aliquots taken to measure optical density at 600 nm and the weight of surfactant sediment recovered in the pellet after centrifugation and completely decanting the supernatant. An extinction coefficient for PAP surfactant sediment (8.049+/−0.245 SEM) was determined from a plot of turbidity versus concentration for 135 bags of WLL fluid ($R^2$=0.91).

Panel E shows a turbidity-based disease severity index (T-DSI) for hPAP. The T-DSI is a single value accounting for all the PAP sediment in all bags of WLL from one therapeutic procedure—see below). T-DSI was compared to the total surfactant sediment recovered (a measure of disease severity) for each therapeutic WLL procedure (27 autoimmune PAP, 49 hereditary PAP). The T-DSI was calculated by multiplying the turbidity of each bag by its volume and dividing by the total volume (i.e., in all bags), and then summing this result for all bags from the procedure: T-DSI is the sum of volume-weighted turbidities for all bags. The total surfactant sediment recovered from each patient by WLL therapy was determined by summing the pellet weights of each bag. Statistical analysis was done using Sigma Plot.

EXAMPLES

The following describes the generation of a state-of-the art 3$^{rd}$ generation self-inactivating (SIN) lentiviral vector construct expressing a codon-optimized human CSF2RA cDNA from an internal elongation factor 1a (short; EFS) promotor (Lv.EFS.CSF2RA$^{coop}$). This vector permits transduction of hematopoietic stem and progenitor cells prior to their differentiation into a monocyte/macrophage lineage. Also described are the first preclinical functionality and safety studies for this vector in both cell lines and primary human cells, as well as in the Csf2ra$^{KO}$ mouse model of human hPAP. This model shares the same clinical, physiological, histopathological, and biochemical abnormalities, disease biomarker, and natural history of children with hPAP caused by CSF2RA mutations. We have determined that hPAP caused by Csf2rb or Csf2ra gene ablation in mice are identical and have similar lung pathology (surfactant filled alveoli, preserved architecture, cytopathology (Oil-Red-O stained macrophages, cell debris), reduced mRNA (PU.1, PPAR γ, ABCG1), increased BAL turbidity, and BAL biomarkers (GM-CSF, MCSF, and MCP-1). The clinical course is also similar with progressive surfactant accumulation.

We have further determined that the histopathology of hPAP is indistinguishable in mice and humans caused by mutations in CSF2RA/Csf2ra and CSF2RB/Csf2rb. The disease is also progressive in both mouse models and humans, which can be readily quantified by measuring BAL turbidity. Turbidity can be measured by optical light scattering with a spectrophotometer at a wavelength of 600 nm. We have determined an optical extinction coefficient for surfactant of 8.049+/−0.245 determined from 135 consecutive lung lavage samples. Thus, this technique can be used to assess disease severity based on examination of the lung lavage fluid from BAL or WLL.

While a shortened lifespan has not been measured in children with hPAP due to the short time since its discovery in 2008, Csf2rb$^{KO}$ mice clearly have a shortened lifespan that is increased by PMT therapy. The same is expected of Csf2ra$^{KO}$ mice, although survival analysis has not been performed in this model. The BAL cytokine biomarkers are identical in murine and human hPAP. Overall, while human and murine GM-CSF are neither immunologically cross-reactive, or functionally interchangeable, the mechanisms by which they regulate AM clearance and other macrophage functions appears to be similar. Thus, based on extensive studies in these mice, we believe that the hPAP phenotype of Csf2ra$^{KO}$ and Csf2rb$^{KO}$ mice provide faithful, accurate models of human hPAP.

Described here are studies using the Lv.EFS.CSF2RA$^{coop}$ to transduced CD34+ cells which demonstrate that the CD34+ derived and in vitro differentiated macrophage cells survive, replicate, and engraft after transplantation into the lungs, primarily in the endo-alveolar compartment, replacing the endogenous defective alveolar macrophage cells due to a strong survival advantage of cells with functional receptors. The transplanted cells also adopt the phenotype of normal alveolar macrophage cells and effectively reverse the manifestations of disease, including normalizing hPAP related biomarkers.

These studies suggest that lentiviral gene transfer and pulmonary macrophage transplantation can be safe, well-tolerated, and effective as a therapy in a mouse model of hPAP, laying the foundation for human clinical therapy.

Material and Methods

Cell culture: All cells were cultured under standard conditions (37° C. and 5% $CO_2$). Murine Ba/F3 cells were cultured (RPMI-1640, 10% fetal calf serum 100 units/ml penicillin/streptomycin) with 2 ng/ml murine IL-3 on suspension culture plates. mAM cells were cultured (DMEM, 10% fetal calf serum 100 units/ml penicillin/streptomycin) on adherent culture plates.

CD34+ Cell Isolation, Culture and Differentiation

Human CD34+ cells were isolated from umbilical cord blood. After gradient centrifugation of peripheral blood mononuclear cells (PBMCs), CD34+ cells were enriched from PBMCs by magnetic separation using CD34+ MicroBead™ kit (Miltenyi, Bergisch-Gladbach, Germany). Cells were cultured in StemSpan™ (Stem Cell Technologies, Vancouver, Canada) containing 100 U/ml penicillin/streptomycin, 2 mM L-glutamine (Thermo Fisher Scientific), 100 ng/ml hSCF, 100 ng/ml hFlt31 and 50 ng/ml hTPO (all Peprotech) at 37° c. and 5% $CO_2$. For differentiation towards macrophages, CD34+ cells were transferred to RPMI1640 containing 10% FCS, 100 U/ml penicillin/streptomycin, 100 ng/ml hM-CSF, 100 ng/ml hGM-CSF, 100 ng/ml hFlt31, 20 ng/ml hIL-3 and 20 ng/ml hIL-6 (all Peprotech) for at least 10 days.

Lentiviral Vector Construction and Production

For constitutive CSF2RA transgene overexpression, the human cDNA sequence from PUBMED online (NM 006140) was used to generate a codon optimized cDNA. Codon-optimized CSF2RA cDNA was flanked by AgeI and SalI restriction sites and synthesized by GeneScript™. Using restriction digestion (AgeI, SalI), CSF2RA cDNA was inserted into a third generation self-inactivating lentiviral backbone (pRRL.cPPT.EFS.GFP), which was used as a control vector throughout the experiments. The final vector pRRL.cPPT.EFS.CSF2RA$^{coop}$ (Lv.EFS.CSF2RA$^{coop}$) was sequence-verified by DNA sequencing.

For production of viral particles a transient four plasmid transfection of HEK293T cells was used as previously described in Lachmann N, et al., Gene Ther. 2015; 22(11): 883-892. Briefly, HEK293T cells were cultured (HEPES buffered DMEM, 10% fetal calf serum 100 units/ml penicillin/streptomycin) with 25 µM chloroquine. Cells were transfected using calcium phosphate precipitation in the presence of 8 µg/ml gag/pol, 5 µg/ml pRSV-Rev, 5 µg/ml lentiviral vector plasmid and 1.5 µg/ml VSVg. Viral supernatants were harvested 36 and 48 h post transfection, filtered and concentrated by ultracentrifugation (16 h at 14,000 g, 4° C.). Viral titers were determined by several dilution on SC-1 fibroblasts and flow cytometry analysis.

Lentiviral Transduction

For lentiviral transduction of cell lines, 100,000 mAM or Ba/F3 cells were transferred to respective culture medium containing 4 µg/ml protamine sulfate. Viral transduction was performed for 24 h. Thereafter, cells were washed and transferred back to standard culture medium. Transduction efficiency was analyzed 72 h after transduction using flow cytometry. CD34+ cells were transduced using RetroNectin® (Takara Bio Inc., Japan) with a MOI of 20 according to the manufacturer's instructions.

Generation of Murine Alveolar Macrophage (mAM) Cell Lines mAM cells are an alveolar macrophage cell line derived from GM-CSF-deficient mice as described in Shibata Y, et al., Immunity. 2001; 15(4):557-567. mAM-hGM-R cell lines expressing wildtype human GM-CSF receptor alpha and beta chains were generated by transducing mAM cells with retroviral vectors MIEG3 (inserted with CSF2RA cDNA) and MSCV2.1 (inserted with CSF2RB cDNA) (Suzuki T, et al., *J Exp Med.* 2008; 205(12):2703-2710). To establish mAM-hPAP cell lines, mAM cells were transduced with retroviral vectors MIEG3 inserted with hPAP-mutant CSF2RA cDNA (G196R) and MSCV2.1 inserted with wild-type CSF2RB cDNA. Each cell line was selected by GFP expression (MIEG3 vector) and neomycin drug resistance (MSCV2.1 vector).

Single Cell Sorting

Before sorting, Ba/F3 cells were stained with CD116 PE antibody for 45 min at 4° C. and separated on a XDP flow cytometer (Beckman Coulter, Krefeld, Germany). Single cells from high, medium and low expressing fractions were sorted and cultured as previously described.

Cytospins

Approximately 50,000 cells were resuspended in 200 μl PBS and centrifuged onto glass slides using a medite Cytofuge® (medite, Burgdorf, Germany) at 600×g for 7 min. Glass slides were subsequently stained using Pappenheim staining.

hGM-CSF-Dependent Survival Assay

Ba/F3 cells were transferred to X-VIVO 15™ for starvation. After 24 h of culture without cytokines 100,000 cells per condition were transferred either to X-VIVO™ 15 only as a negative control or X-VIVO™ 15 supplemented with either 2 ng/ml murine IL-3 as a positive control or 5, 10, 20, 50 or 100 ng/ml hGM-CSF and incubated for 72 h. Percentage of surviving cells was analyzed using FSC/SSC gating in flow cytometry analysis.

STAT5 Phosphorylation Analysis

Cells were starved in X-VIVO™ 15 for 24 h as above then stimulated for 15 min in X-VIVO 15 either without cytokines, supplemented with 2 ng/ml mIL-3 or 10 ng/ml hGM-CSF. Cells were harvested and lysed using RIPA buffer with proteinase inhibitor cocktail. Cell lysates were analyzed by Western analysis using antibodies against STAT5 and pSTAT5 (Suzuki T, et al., *J Exp Med.* 2008; 205(12):2703-2710).

Quantitation of Vector Copy Numbers

Genomic DNA was isolated using GeneElute™ Mammalian Genomic DNA Miniprep Kit (Sigma-Aldrich). Quantitative real-time PCR was performed on a StepOnePlus™ light cycler (Applied Biosystems) using Fast SybrGreen™ reagent (Qiagen) and primers detecting either wPRE (Fwd: GAGGAGTTGTGGCCCGTTGT (SEQ ID NO:2), Rev: TGACAGGTGGTGGCAATGCC (SEQ ID NO:3); or the polypyrimidine tract binding protein 2 (PTBP2) (Fwd: TCTCCATTCCCTATGTTCATGC (SEQ ID NO:4), Rev: GTTCCCGCAGAATGGTGAGGTG (SEQ ID NO:5) sequence as the internal control, respectively. Normalization was performed using a plasmid standard harboring the relevant PTBP2 sequences. Copy number calculations were performed by the Pfaffl method (Pfaffl MW, "A new mathematical model for relative quantification in real-time RTPCR." *Nucleic Acids Res* 2001 May 1; 29(9): e45.

GM-CSF Clearance 100,000 mAM cells were seeded to a 24-well adherence plate in standard culture medium. After 24 h medium was replaced by X-VIVO™ 15 containing 1 ng/ml hGM-CSF. Medium samples were taken at 0, 1, 3, 6, 12 and 24 h of stimulation and hGM-CSF concentration was determined using a Human GM-CSF ELISA Ready-SET-Go!™ kit.

Southern Analysis

Southern analysis was carried out according to standard protocols. Briefly, 10 μg of genomic DNA was digested using the restriction enzyme AflII. 10 pg and 100 pg of plasmid vector DNA Lv.EFS.CSF2RA$^{coop}$ served as positive controls. Digested DNA was separated on a TAE agarose gel and transferred to a Biodyne™ B nylon membrane. Blotted DNA was analyzed with a $P^{32}$-labeled EcoRI fragment (~600 bp) of the woodchuck hepatitis element (wpre) using the DecaLabel™ DNA labeling kit. After alkaline stripping, the membrane was rehybridized with a radioactive labeled BamHI fragment (~900 bp) of the codon optimized CSFR2RA cDNA. HindIII digested $P^{32}$-labeled bacteriophage lambda DNA served as a size standard.

Colony-Forming Assay

In order to evaluate clonogenic potential of CD34+ cells, 1500 cells/ml were seeded in methylcellulose (R&D systems, Minneapolis, MN, USA) HSC003 containing Epo, GM-CSF, IL-3 and SCF in 8.8 cm² cell culture dishes with 2 mm grid (Thermo Scientific Nunc) and cultured for 7 days in the incubator at standard culture conditions in a separately closed humid chamber. The overall number of colonies was counted after 7-10 days.

Statistical Analysis

Statistical analysis was performed using Prism 6 software (GraphPad, La Jolla, CA, USA). Unless otherwise noted, analysis of variance (ANOVA) with respective post hoc testing (see figure legend) was used. All data were reproducible in independent experiments.

Results: Lentiviral-Vector Design and Functionality in Murine Ba/F3 Cells

Figure 7A:
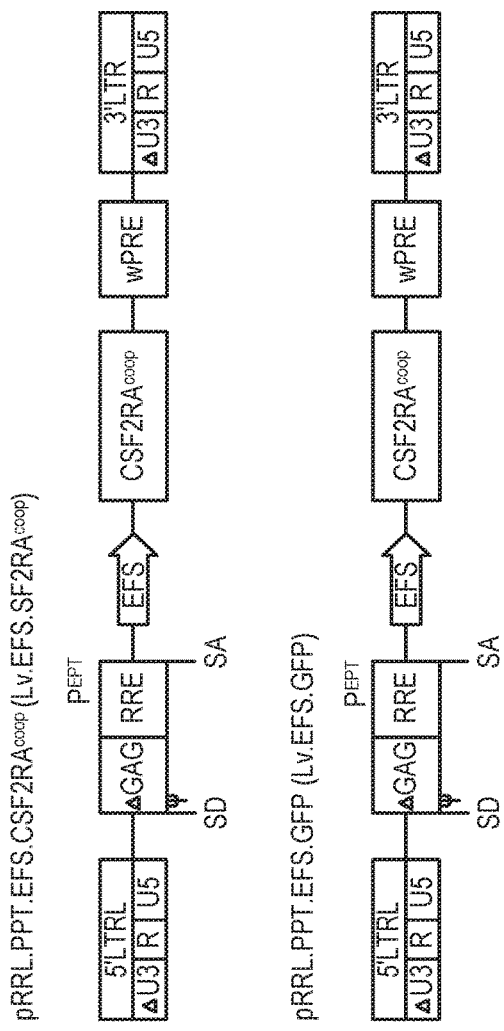
FIG. 7A-F: Vector design and functionality in the Ba/F3 cell line. (a) Schematic representation of the 3rd generation SIN lentiviral constructs Lv.EFS.CSF2RA$^{coop}$ expressing the human codon optimized cDNA of CSF2RA (upper picture) and Lv.EFS.GFP control vector (lower picture). Additional detail is provided infra. (b) Human CD116 expression in untransduced (left) and non-sorted transduced (right) Ba/F3 cells. (c) hGM-CSF dependent survival of Lv.EFS.GFP and Lv.EFS.CSF2RA$^{coop}$ transduced and non-sorted Ba/F3 cells. Murine IL-3 (mIL-3) serves as a positive control, no cytokines servers as a negative control (n=3; Two-way ANOVA using Sidak's Post-Hoc testing). (d) Representative plots analyzing mCD131 and hCD116 expression in untransduced and Lv.EFS.CSF2RA$^{coop}$ transduced Ba/F3 cells with defined VCNs of 1, 2 and 4. (e) Mean fluorescence intensity (MFI) of hCD116 expression in untransduced and Lv.EFS.CSF2RA$^{coop}$ transduced Ba/F3 cells with defined VCNs of 1, 2 and 4 (left) and bar graph depicting the CD116 MFI (right; n=3; One-way ANOVA using Dunnett's Post-Hoc testing). (f) hGM-CSF dependent survival of Lv.EFS.CSF2RA$^{coop}$ transduced Ba/F3 cells with defined VCNs of 1, 2 and 4 (n=3; One-way ANOVA using Dunnett's Post-Hoc testing). ns=not significant, *P<0.05, P<0.01, *P<0.001, ****P<0.0001.

To lay the foundation for a human gene therapy approach using HSPC-derived macrophages, we have utilized a SIN-LV backbone, equipped with an EFS promoter to constitutively express a codon-optimized cDNA of CSF2RA (Lv.EFS.CSF2RA$^{coop}$, FIG. 7A). As a control vector, we used the same vector architecture to express a green fluorescent protein instead of CSF2RA (Lv.EFS.GFP, FIG. 7A). To direct the tropism of the lentiviral vector towards human and murine hematopoietic cells both vectors were pseudotyped with the vesicular stomatitis virus glycoprotein (short VSVg).

Figure 7C:
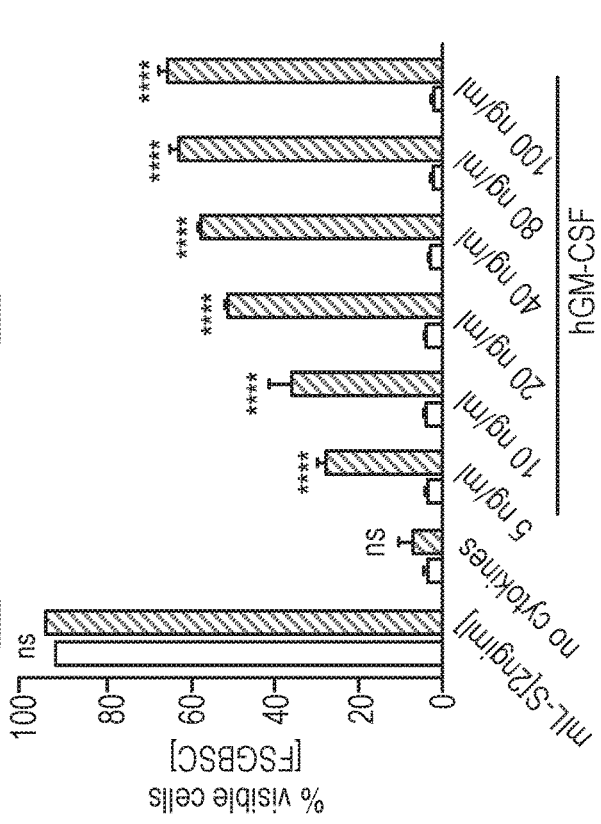
Figure 7B:
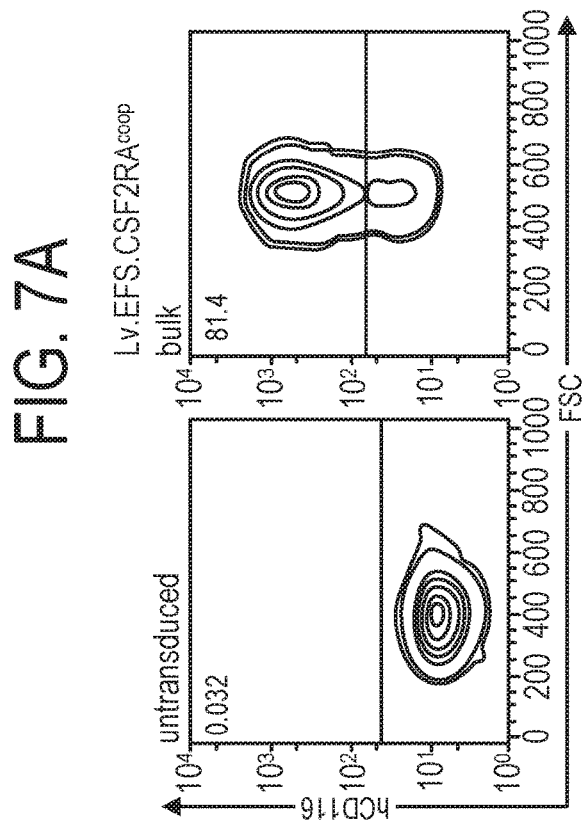

To evaluate the functionality of transgenic CSF2RA expression, we made use of the murine mIL3/mGM-CSF-dependent pro B cell line Ba/F3. Physiologically, CSF2RA initiates GM-CSF-dependent signaling by extracellular binding to GM-CSF. Upon pairing with CSF2RB, high affinity binding of GM-CSF is induced which in turn is necessary for intracellular GM-CSF-dependent signal transduction. The same process has been described for the interaction of murine Csf2rb and human CSF2RA in the presence of hGM-CSF, highlighting their suitability to directly study proliferation and cell survival after lentiviral transduction. To test the functionality of our pre-clinical vector, we transduced Ba/F3 cells with an MOI of 1 and analyzed CSF2RA expression (CD116) by flow-cytometry. In contrast to non-transduced control cells, Lv.EFS.CSF2RA$^{coop}$ transduced cells showed a clear population of more than 80% CD116 positive cells compared to non-transduced control cells (FIG. 7B). Next, we assessed the functionality of CSF2RA in Lv.EFS.CSF2RA$^{coop}$ or Lv.EFS.GFP transduced cells in the presence or absence of hGM-CSF. Both GFP and CSF2RA transduced cells were dependent upon the presence of murine IL-3 for viability (FIG. 7C). Increasing amounts of hGM-CSF rescued cell viability in the absence of IL-3 for CSF2RA transduced cells, but not for GFP transduced cells. Importantly due to concerns of vector-related genotoxicity, the constitutive or overexpression of CSF2RA did not affect cell proliferation or apoptosis in transduced cells.

Figure 7D:
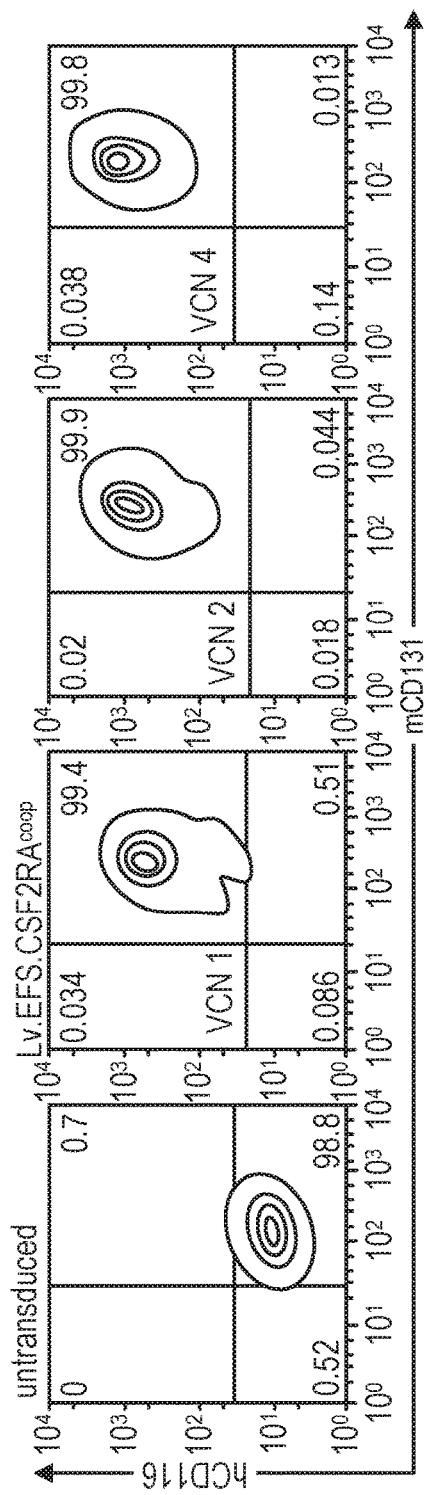
Figure 7E:
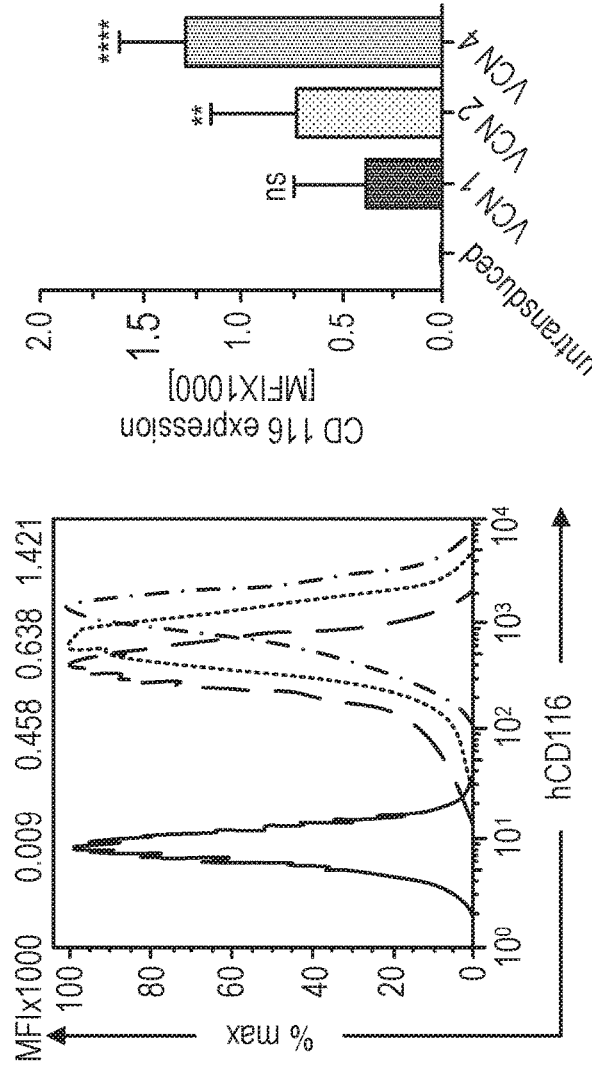
Figure 7F:
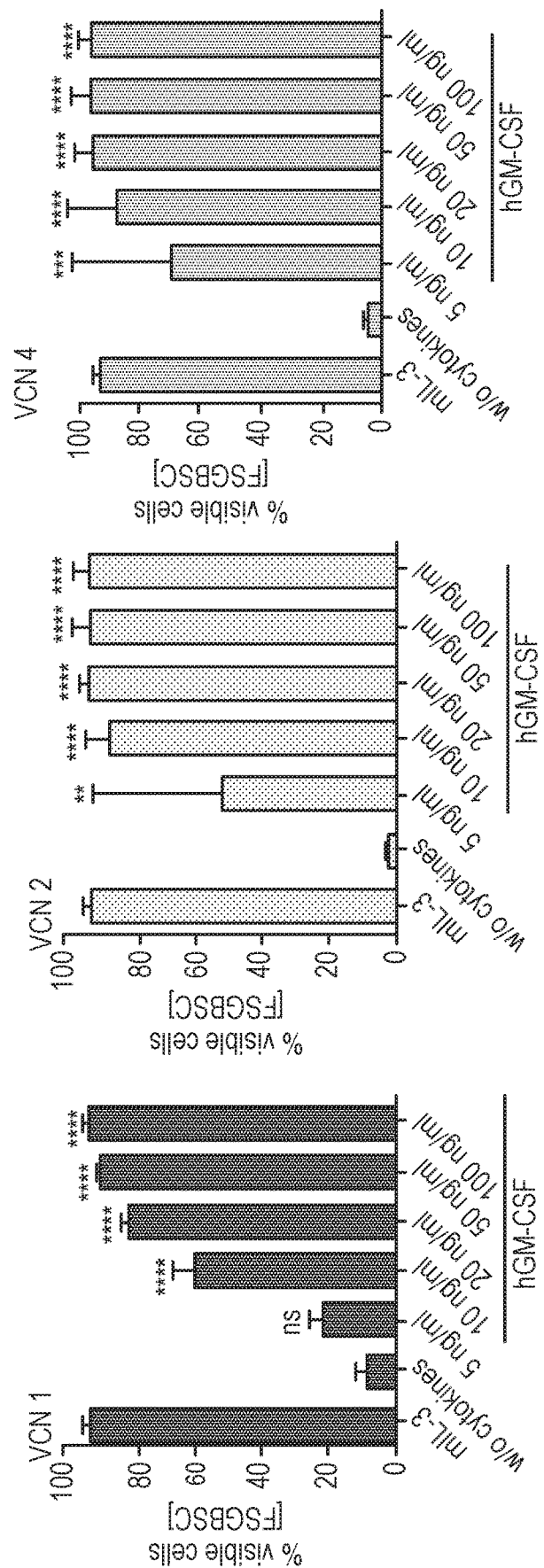

After evaluating CSF2RA functionality in non-sorted bulk cell densities, we performed single cell sorting of Lv.EFS.CSF2RA$^{coop}$ cells to establish individual cell clones harboring 1, 2 or 4 vector copies (vector copy number (VCN) 1, 2 or 4). Analyzing vector functionality in cells with only a single vector copy is of high clinical relevance as the increase in vector copy numbers may also increase the risk of mutagenic events. Irrespective of the VCN, all established clones showed a gene marking of more than 99% and a stable CSF2RA expression (FIG. 7D). However, an increase in transgene expression could be detected by increased mean MFI values for CD116 of 374 for VCN1, 720 for VCN2, and 1252 for a VCN of 4 (FIG. 7E). Of note, expression of murine Csf2rb was not affected upon overexpression of human CSF2RA (FIG. 7D). In order to discriminate VCN-dependent functionality in cells transduced with Lv.EFS.CSF2RA$^{coop}$, we cultured the individual clones in the presence or absence of hGM-CSF. As expected, maintenance culture in the presence of mIL-3 had no effect on cell survival, irrespective of the VCN. A concentration of 5 ng/ml hGM-CSF was sufficient to rescue more than 50% of the transduced cells harboring a VCN of more than 2, which was similar to the observation in bulk cells. However, a more pronounced GM-CSF dose dependency of cell growth was observed for cells harboring a VCN of 1. Although 60% of the cells could be rescued by 10 ng/ml of hGM-CSF, only 20% of viable cells could be detected in 5 ng/ml hGM-CSF cultures (FIG. 7F). We compared the VCN dependence of CSF2RA driven either by EFS using the codon-optimized vector compared to two other SIN-LV vectors, each expressing the wild-type CSF2RA gene driven either by the EFS or the human phosphoglycerate kinase (PGK) promoter. These studies confirmed VCN-dependent expression levels of CSF2RA on the cell surface for all three vectors but demonstrated that cells transduced with the codon optimized CSF2RA vector exhibited the highest transgene expression (data not shown). The increased expression levels from the CSF2RA$^{coop}$ cDNA could also be seen in the GM-CSF depended cell survival of Ba/F3 cells. Here, Lv.EFS.CSF2RA$^{coop}$ transduced cells showed a pronounced response to GM-CSF when compared to the other vector constructs (data not shown). These data indicate the advantage of using the codon optimized cDNA.

Figure 8A:
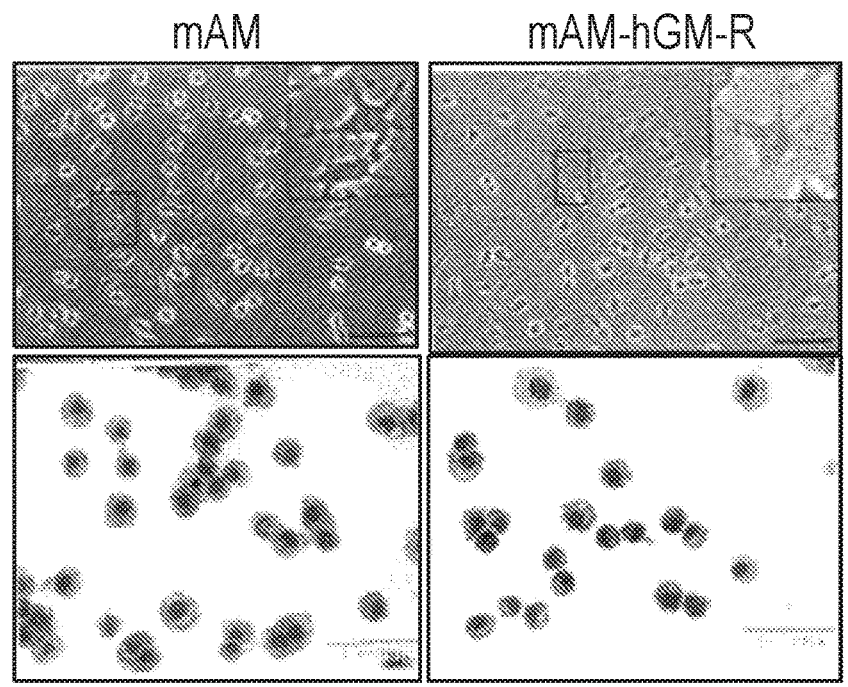
FIG. 8A-E: Characteristics of the new murine alveolar macrophage cell line (mAM). (a) Morphology of the mAM parental line (left) and mAM-hGM-R line expressing the human GM-CSFR (right); (b) Representative histogram depicting hCD116 expression of mAM (light) and mAM-hGM-R (dark) cells. (c) Western analysis of overall STAT5 expression and phosphorylated STAT5 (pSTAT5) in response to stimulation with human or murine GM-CSF in mAM, mAM-hGM-R, RAW264.7, and human PBMC cells. No addition of cytokines (−) served as a negative control, human PBMCs and murine RAW264.7 cells served as a positive controls for human and murine GM-CSF, respectively. (d) Western analysis of STAT5 expression and pSTAT5 showing dose dependent phosphorylation of STAT5 in response to hGM-CSF (0-1000 ng/ml) in mAM-hGM-R cells. (e) Western analysis of time dependent phosphorylation of STAT5 after stimulation with hGM-CSF (0, 5, 15, 30 and 60 min stimulation) in mAM-hGM-R cells.
Figure 8B:
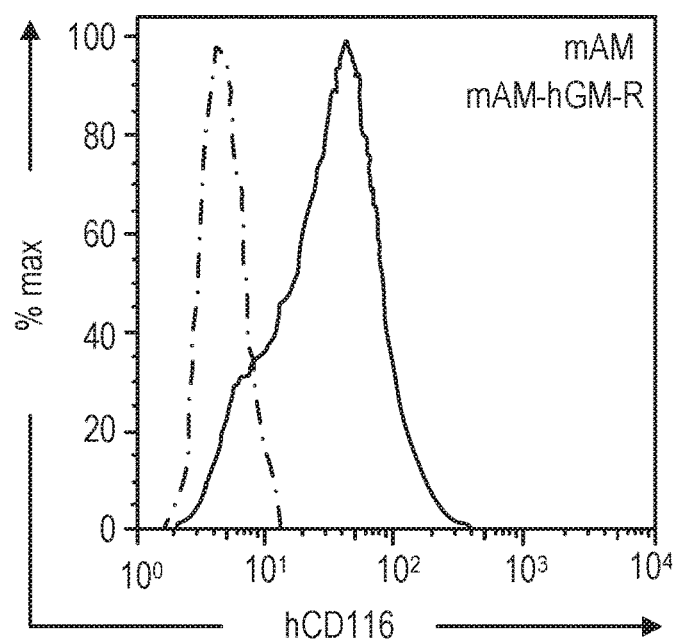
Figure 8C:
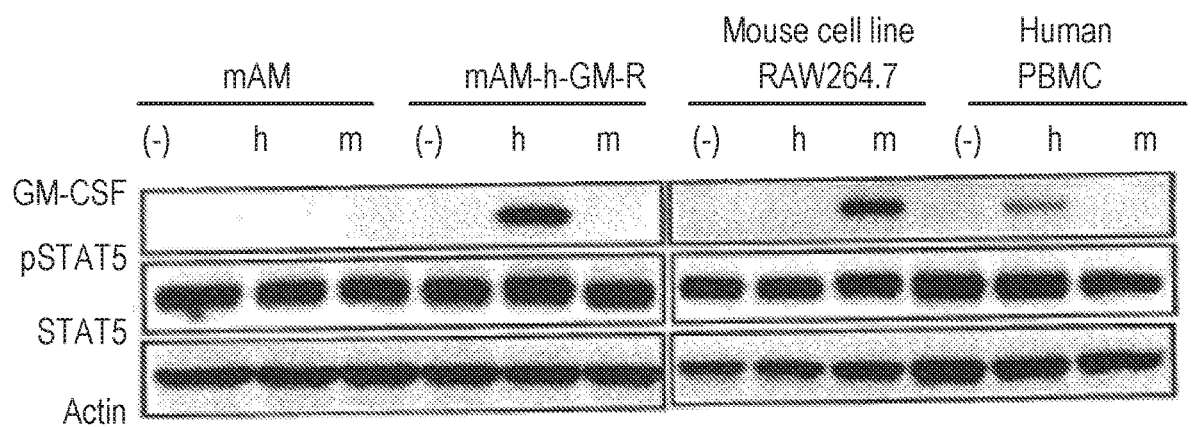

Results: A Murine Alveolar Macrophage Cell Line to Evaluate hGM-CSF Functionalities To gain insights into CSF2RA overexpression from our Lv.EFS.CSF2RA$^{coop}$ construct, we generated a cell line derived from murine alveolar macrophages of GM-CSF$^{-/-}$ mice and which do not express Csf2ra/b (mAM) and is therefore deficient in mGM-CSF signaling. The parental mAM cell line was previously transduced with retroviral vectors expressing the human GM-CSF receptor α and β chain, creating a cell line which selectively reacts to hGM-CSF (mAM-hGM-R). Both mAM and mAM-hGM-R cell lines exhibited similar AM-like morphology in culture (FIG. 8A) as well as comparable growth characteristics (data not shown). After retroviral mediated transduction the mAM-hGM-R line robustly expressed human CD116 on the cell surface (FIG. 8B). As mAM-hGM-R express human CSF2RA, we assessed GM-CSF specificity using murine and human GM-CSF. Non-transduced mAM cells did not respond to murine or human GM-CSF, mAM-hGM-R cells were able to phosphorylate STAT5 only in the presence of hGM-CSF, as were human PBMC, and murine RAW264.7 cells were able to phosphorylate STAT5 only in the presence of murine GM-CSF (FIG. 8C).

Figure 8D:
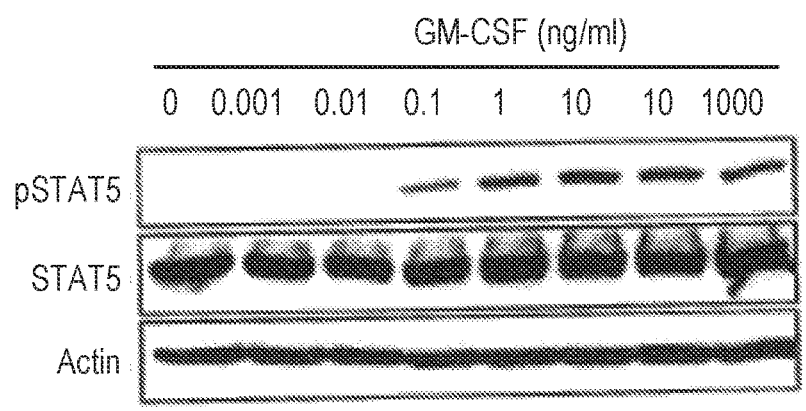
Figure 8E:
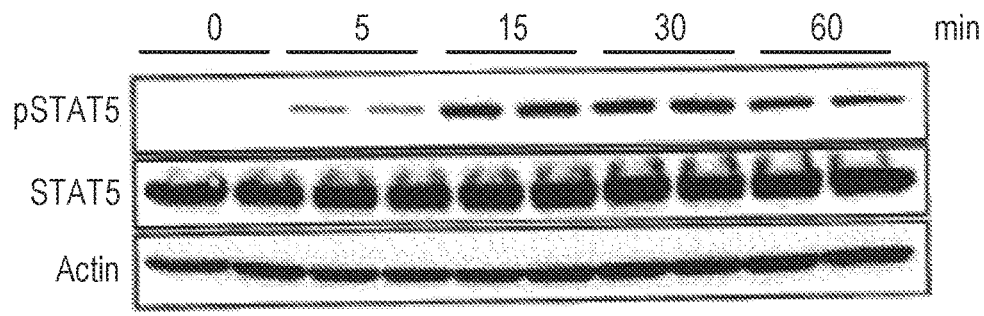

We next evaluated hGM-CSF sensitivity in mAM-hGM-R cells by cultivation in the presence of different concentrations of hGM-CSF for 15 min. As depicted for different concentrations of hGM-CSF, mAM-hGM-R cells were able to phosphorylate STAT5 in the presence of 0.01 ng/ml onwards, whereas no pSTAT5 could be detected at lower concentrations (FIG. 8D). Similar observations were made analyzing time-dependent STAT5 phosphorylation. Here, stimulation with 10 ng/ml hGM-CSF led to detectable levels of pSTAT5 within 5 minutes following administration (FIG. 8E). Taken together, these data highlight the suitability of mAM cells for studying GM-CSF down-stream signaling and as an in vitro system for evaluating the Lv.EFS.CSF2RA$^{coop}$ lentiviral vector.

Figure 9A:
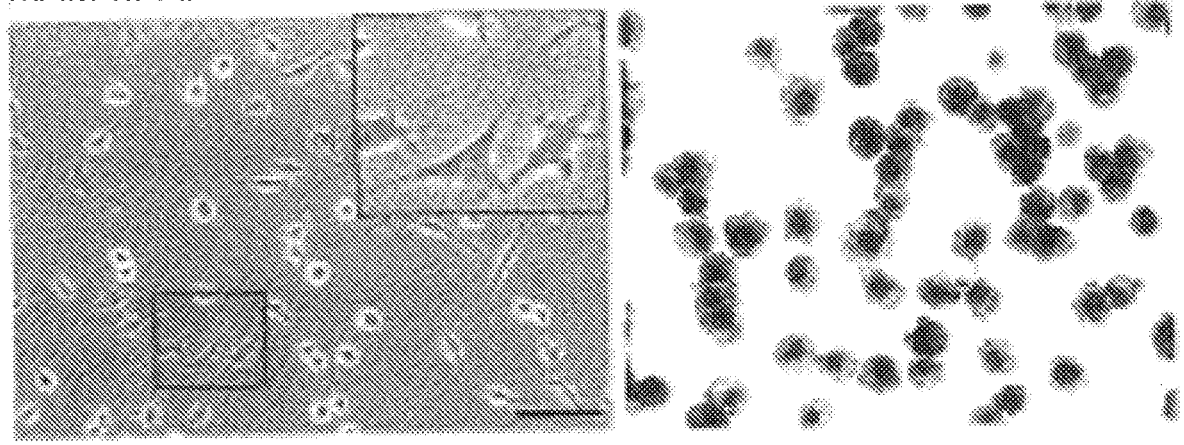
FIG. 9A-G: (a) Morphology of the mAM-hPAP cell line expressing the mutated human CSF2RA gene; Scale bar: 100 μm. (b) Representative histogram depicting hCD116 expression of parental mAM cell line, mAM-hGM-R cells, and mAM-hPAP cells. (c) hCD116 expression in mAMhPAP cells either untransduced or transduced with Lv.EFS.CSF2RA$^{coop}$ using MOIs of 0.1, 0.5, 1 and 10. (d) Bar graph of hCD116 expression summarizing three independent transductions (n=3; One-way ANOVA using Dunnett's Post-Hoc testing). (e) Correlation between hCD116 MFI and VCN indicating a linear relationship between VCN and CD116 expression. (f) Southern analysis using a transgene specific probe to detect the CSF2RA transgene. 10 and 100 pg of the lentiviral packaging plasmid served as a positive control. (g) hGM-CSF uptake from cell culture medium. mAM and mAM-hPAP cells were not able to clear hGM-CSF from the cell culture supernatant, whereas mAM-hGM-R and mAM-hPAP$^{Lv\ EFS\ CSF2RAcoop}$ cells efficiently cleared hGM-CSF over a period of 72 h. ns=not significant, *P<0.05, ****P<0.0001.
Figure 9B:
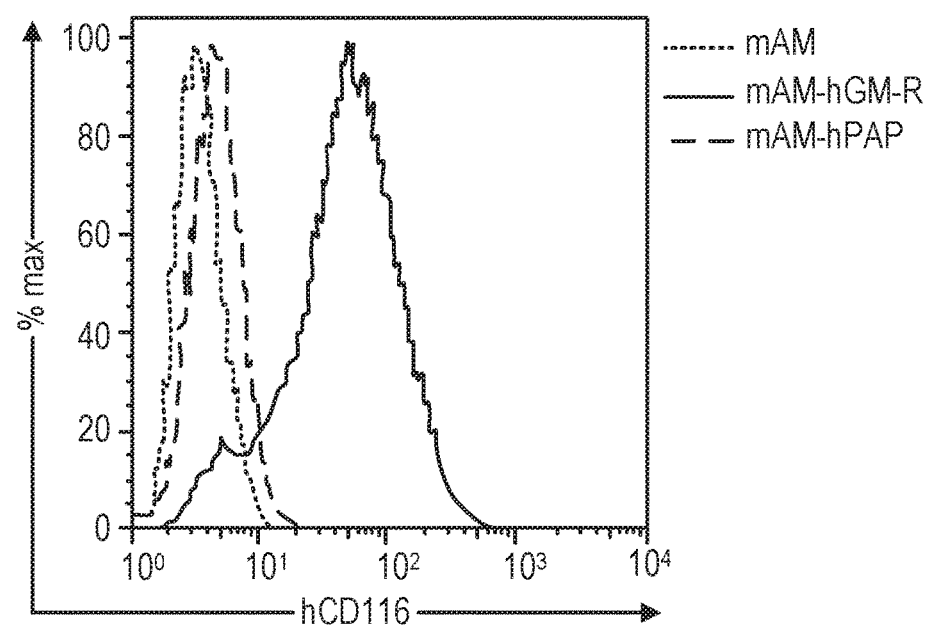

Results: Vector Functionality in Genetically Modified Murine Alveolar Macrophage Cell Line We next used the same parental cell line and introduced the wild type human CSF2RB cDNA and an aberrant human CSF2RA cDNA (referred to as mAM-hPAP). The aberrant CSF2RA cDNA carries a G to A point mutation in exon 7 (G196R) within the CSF2RA gene. Similar to the parental mAM line, mAM-hPAP shows typical macrophage-like morphology in bright field and cytospin images (FIG. 9A), but mAM-hPAP cells do not express cell surface CSF2RA, as evaluated by flow cytometry (FIG. 9B).

Figure 9C:
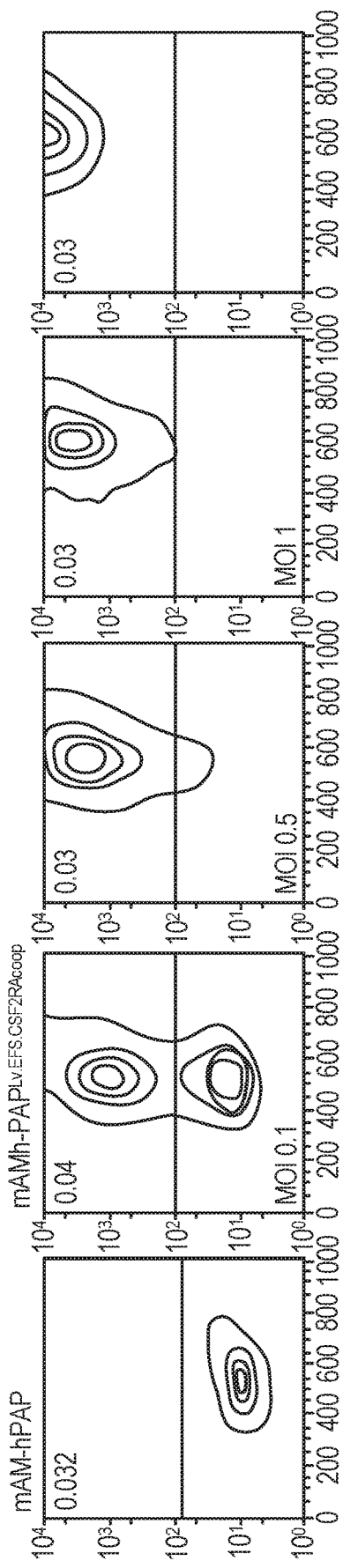
Figure 9D:
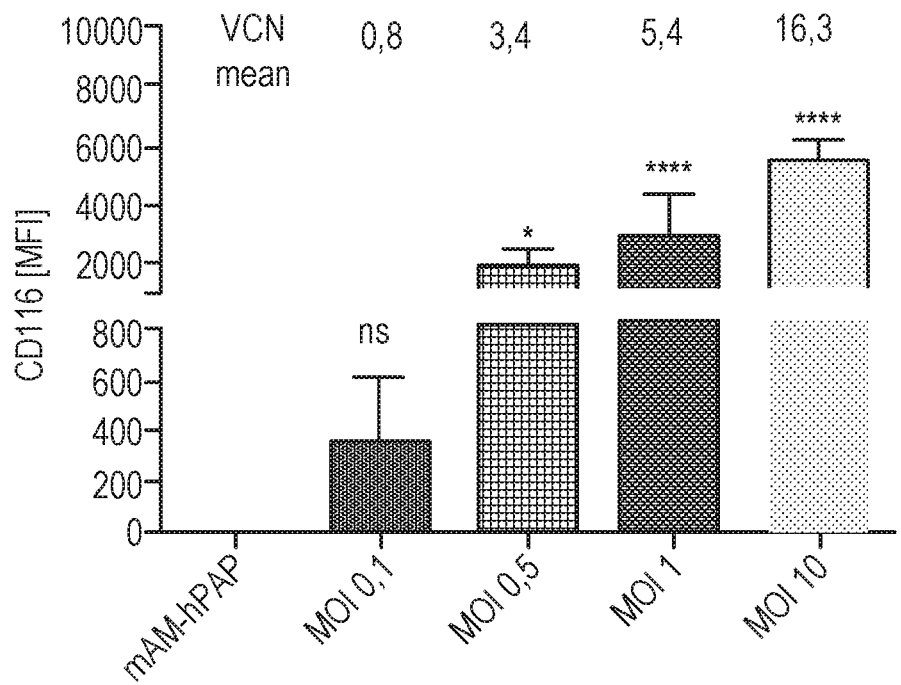
Figure 9E:
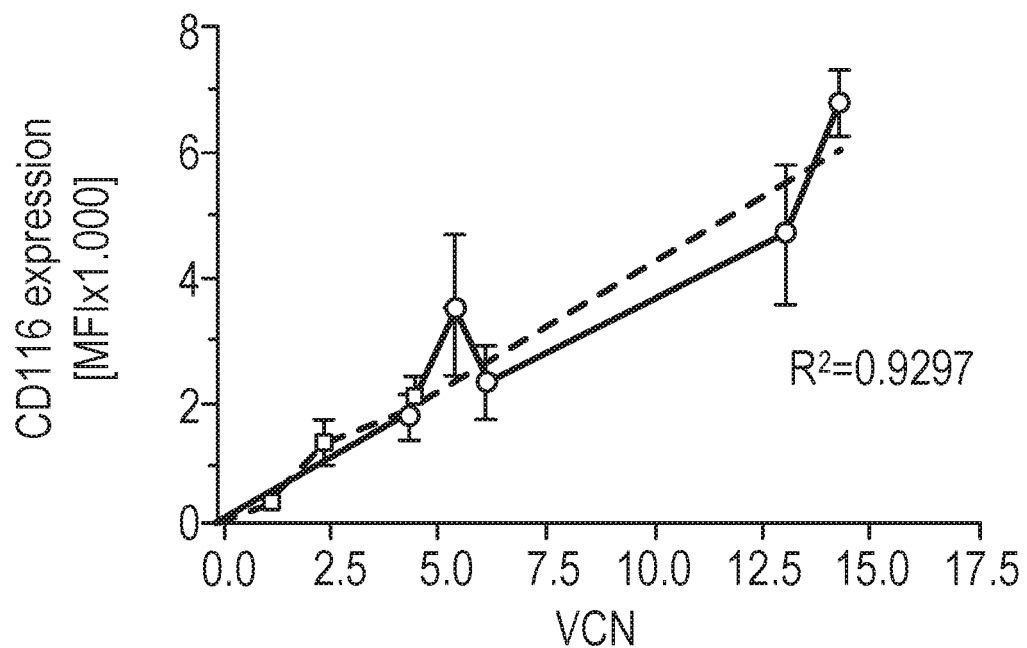
Figure 9F:
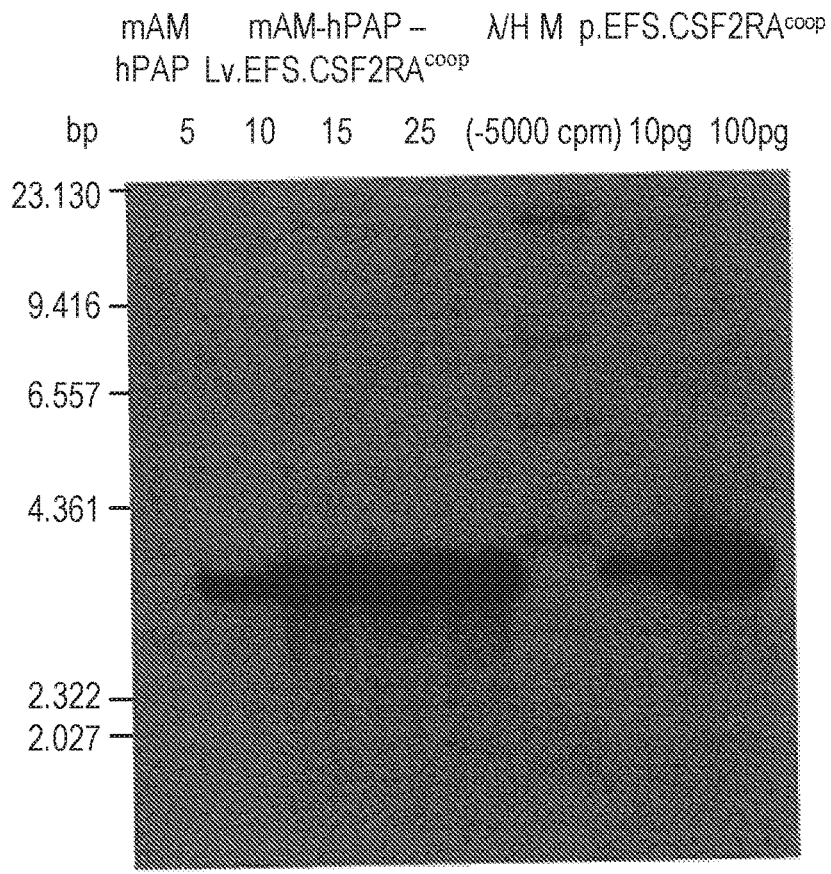
Figure 9G:
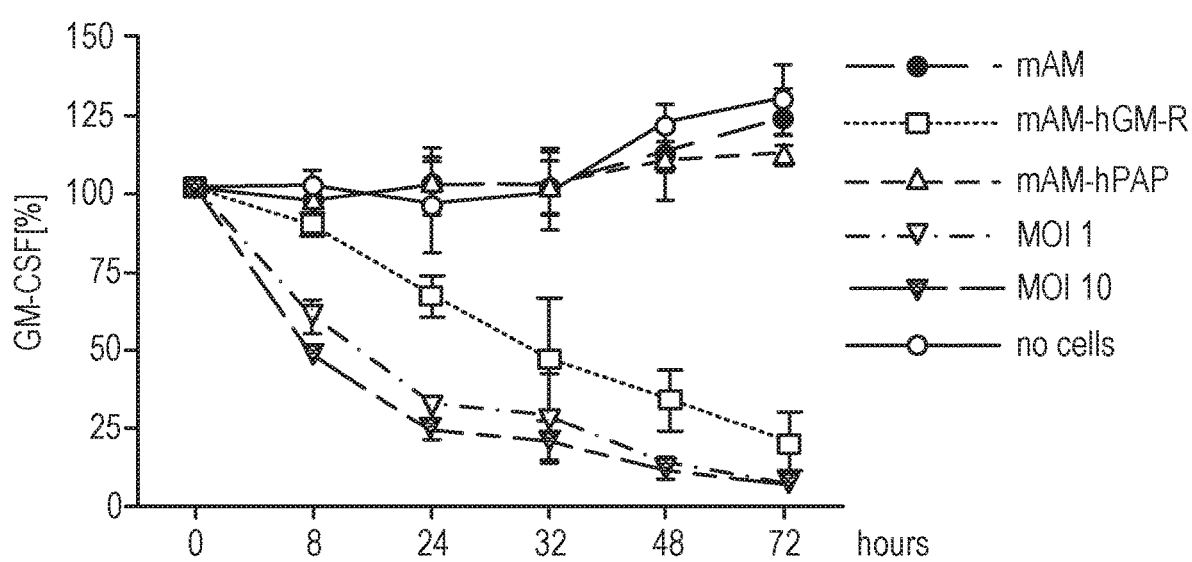

Next, we established individual mAM-hPAP clones using different MOIs of Lv.EFS.CSF2RA$^{coop}$. Similar to Ba/F3 cells, expression of CSF2RA in transduced mAM-hPAP cells increased with increasing MOI and VCN, reaching a MFI of 5073 in mAM-hPAP transduced with a MOI of 10 (FIG. 9B,C). mAM-hPAP cells transduced with an MOI of 0.1 had a VCN of 0.8, cells transduced with a MOI of 0.5, 1, or 10, harbored a VCN of 3.4, 5.4, or 16.3, respectively (FIG. 9C,D). Similarly, when analyzing VCN and expression of CSF2RA a direct correlation in a linear scale was observed (FIG. 9E). In order to confirm proviral stability after integration and to demonstrate absence of deletion or recombination events during integration in mAM-hPAP cells, we performed Southern analysis using AflII restriction and radioactively labeled probes specific for the CSF2RA transgene. No transgene was detectable in untransduced mAM-hPAP cells while the transgene was present in increasing amounts with MOI's of 5, 10, 15, and 25 in CSF2RA transduced cells, demonstrating that the amount of transgene was VCN dependent (FIG. 9F). We next evaluated the functionality of the CSF2RA transgene by measuring the ability of transduced cells to clear hGM-CSF from the supernatant, compared to the parental cells and untransduced mAM-hPAP cells. As shown in FIG. 9G, the parental mAM cells, untransduced mAM-hPAP cells, and the "no cell" control were unable to clear hGM-CSF from the medium 72 hours following hGM-CSF administration. In contrast, both mAM-hPAP cell lines transduced with CSF2RA (MOI 1 or 10) were able to clear hGM-CSF with an efficiency similar to that as mAM-hGM-R cells (positive control). In summary, the transduced mAM cells showed sustained CSF2RA transgene expression and GM-CSF clearance over time further highlighting the suitability of the Lv.EFS.CSF2RA$^{coop}$ lentiviral vector to rescue CSF2RA deficiency.

Results: Vector Safety in Primary Human CD34$^+$ Hematopoietic Cells

Figure 10A:
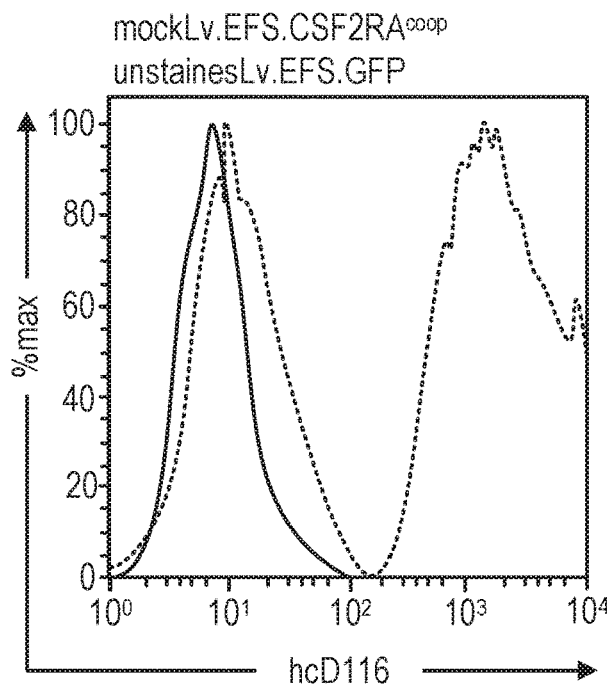
Figure 10B:
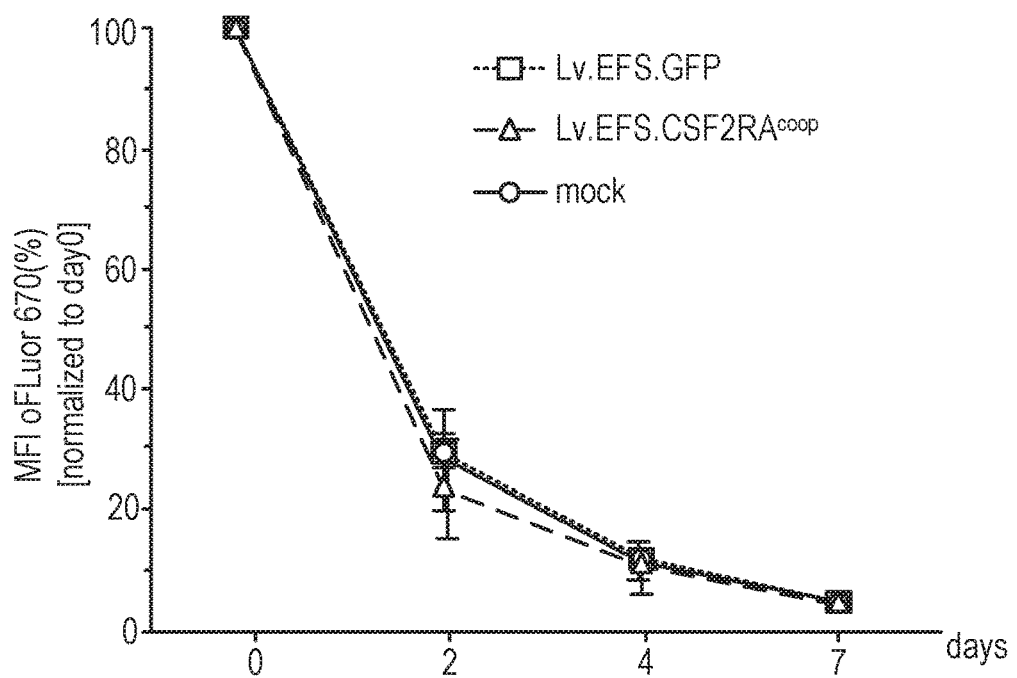

We next used primary human CD34$^+$ cells to evaluate the safety and efficacy of ectopic CSF2RA expression in human cells. First, we transduced primary CD34$^+$ cells with either Lv.EFS.GFP or Lv.EFS.CSF2RA$^{coop}$ constructs and compared CSF2RA expression to mock-transduced controls. Transduction of cells with Lv.EFS.CSF2RA$^{coop}$ showed a clear population of CSF2RA positive cells compared to control or mock treated cells, confirming the ability of the vector to transduce human target cells (FIG. 10A). Next, we evaluated the effects of CSF2RA overexpression on cell proliferation in CD34$^+$ cells and differentiated macrophages. CSF2RA transduced CD34$^+$ cells labelled with the cytoplasmic cell proliferation dye eFluor670 showed equal dilution of the dye compared with GFP and mock transduced cells, confirming that CSF2RA overexpression had no detrimental effects on the proliferation of CD34$^+$ cells (FIG. 10B). In addition, culturing CSF2RA transduced cells in the presence of hSCF, hGM-CSF, hIL-3, and hEPO for 7-10 days in methylcellulose showed no significant differences in total colony formation compared to GFP and mock transduced controls (FIG. 10C). Both GFP and CSF2RA transduced CD34$^+$ cells were also able to give rise to colonies of CFU-GM/GEMM or BFU-E origin, highlighting their multilineage differentiation potential (FIG. 10D).

Figure 10E:
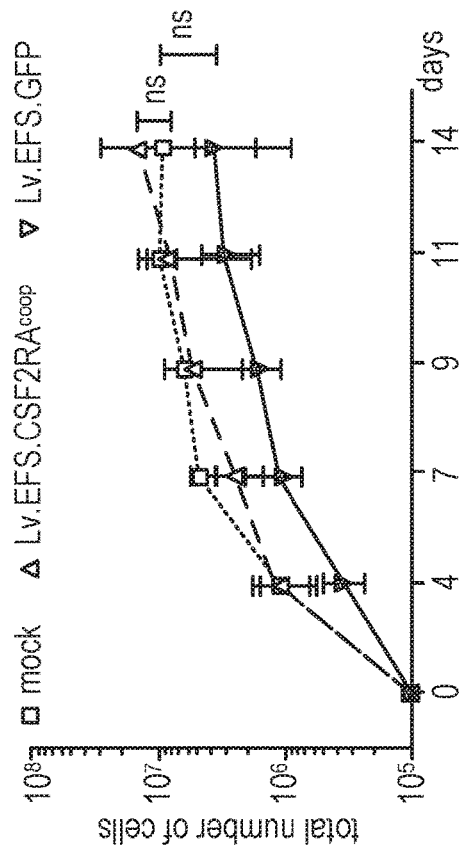
Figure 10F:

Next, we evaluated the effects of the CSF2RA transgene on the differentiation of transduced CD34$^+$ cells towards macrophages by culturing in the presence of IL-3, IL-6, FLT3L, M-CSF and GM-CSF. Differentiation for up to 14 days showed no significant difference in cell growth for cells transduced with the CSF2RA transgene compared to GFP and mock transduced cells (FIG. 10E). Following differentiation, CSF2RA transduced cells had typical macrophage-like morphology in bright field and stained positive for surface markers typically expressed on macrophages (FIG. 10F). CSF2RA transduced cells also showed a surface marker expression pattern of CD45$^+$CD11b$^+$CD14$^+$CD163$^+$ comparable to that of GFP and mock transduced cells (FIG. 10G). Finally, we evaluated hGM-CSF-dependent functionality of transduced macrophages as evidenced by phosphorylation of STAT5. As shown in FIG. 10H,I CSF2RA transduced cells phosphorylated STAT5 in the presence of hGM-CSF to about the same degree as GFP and mock transduced cells.

Discussion and Additional Studies

In the present study, we have established a 3$^{rd}$ generation SIN lentiviral vector to express a codon optimized cDNA of CSF2RA (Lv.EFS.CSF2RA$^{coop}$) and have evaluated this vector in two different cell lines as well as primary human cells. The vector architecture described here incorporates numerous safety promoting enhancements such as the addition of a self-inactivating mutation into the gamma-retroviral backbone which greatly reduces the risk of insertional mutagenesis. Montini et al., *J Clin Invest* 2009 119:964-975. In addition, the promoter enhancer element has been optimized to avoid transgene expression from the long-terminal repeat (LTR) region by inserting the human EFS promoter to constitutively express the CSF2RA transgene. We demonstrate here that constitutive overexpression of CSF2RA by the EFS promoter showed no adverse effects on healthy human CD34$^+$ cells with regard to their survival, proliferation and differentiation potential towards macrophages. Moreover, CSF2RA-transgenic macrophages showed similar functionality to their mock treated or control transduced counterparts. Transduction further resulted in profound expression levels of CSF2RA on the cell surface and vector copy number (VCN) dependent cell growth upon addition of human GM-CSF. We further characterized the vector in a murine alveolar macrophage cell line modified to express a deficient cDNA of the human CSF2R alpha chain, CSF2RA (mAM-hPAP). Transduction of mAM-hPAP cells with CSF2RA demonstrated lentiviral vector mediated expression of CSF2RA and a rescue of GM-CSF clearance over time.

The experimental results presented here provide evidence for the safety and tolerability of lentiviral transduced CSF2RA overexpression in healthy CD34$^+$ cells and macrophages derived from such cells by in vitro differentiation. These data support the suitability of the lentiviral vector construct described here for the functional correction of human autologous cells from hPAP patients suffering from a CSF2R deficiency. The additional data provided below confirms and extends these results.

As discussed above, we found that most CSF2R mutations in human hPAP patients are in the alpha chain. Accordingly, we created a new murine model in which the murine Csf2ra gene is knocked out, the Csf2ra$^w$ mouse model, to lay the foundation for cell therapy in humans using a CSF2RA transgene. This further work is described in the supplemental sections below.

Section 1 describes data validating the Csf2ra$^{KO}$ mouse model as a clinically relevant model of human hPAP and show that Csf2ra transgene-corrected macrophages exhibit restored GM-CSF signaling and clearance in vitro. We further demonstrate that PMT of these cells to Csf2ra$^{KO}$ recipients is effective to ameliorate disease severity, as determined by a decrease in turbidity of bronchoalveolar lavage (BAL) samples.

Section 2 describes the experimental results establishing a direct relationship between the number of macrophages transplanted (cell dose) and the efficacy of PMT therapy as measured by BAL turbidity, providing the basis for determining the minimum effective dose for humans.

Section 3 describes further experiments to validate the functionality of the clinical vector using a genetically modified human embryonic kidney (HEK293) cell line carrying the same human transgenes as described above for the genetically modified mAM cell line, mAM-hPAP. Both ware modified to express a wild-type human CSF2R beta chain and a mutant CSF2R alpha chain (G196R in exon 7). See FIG. 3 and related discussion above pertaining to validation of the clinical vector in mAM-hPAP cells.

Section 4 describes experimental results validating both the functionality of the vector and the process for generating cell corrected patient autologous macrophages described herein by demonstrating the restoration of GM-CSF signaling in primary human cells isolated from a human hPAP patient.

Section 5 describes experimental results demonstrating the safety of the clinical vector in human primary cells isolated from an hPAP patient, in particular the lack of an increase in propensity to form colonies in a CFU assay and no significant impact on the differentiation of human bone marrow derived CD34+ progenitors towards the myeloid lineage following functional GM-Rα expression via lentiviral transduction with the clinical vector.

Section 6 describes experimental results demonstrating that the hGM-Rα-LV provirus is stable in murine and human cell lines.

In sum, the work presented here lays the foundation for the clinical translation of personalized cell therapy for hPAP into the clinic for the treatment of human hPAP patients.

1. Validation of Csf2ra$^{KO}$ Mice as a Clinically Relevant Model of Human hPAP and Efficacy of PMT of Congenic WT Macrophages and Csf2ra Transduced Macrophages as Therapy of hPAP in Csf2ra$^{KO}$ Mice as Determined by BAL Turbidity The validation of Csf2ra$^{KO}$ mice as a clinically relevant model of human hPAP is shown in FIG. 11A-J. (a) Genomic DNA PCR of each genotype mouse (WT)+/+, heterozygous+/−, homozygous−/−). (b) Photomicrographs of bronchoalveolar lavage (BAL) fluid from 10-week old mice of WT and Csf2ra$^{KO}$ mice. (c,d) BAL turbidity is increased in 10-week old Csf2ra$^{KO}$ mice and showed age-dependent progression compared to age-matched WT mice. (e) Immunofluorescent staining for CD116 of alveolar macrophages from WT and Csf2ra$^{KO}$ mice. (f) Oil-red-O staining of cytospin slides of BAL cells from WT and Csf2ra$^{KO}$ Csf2ra$^{KO}$ mice. mice. Csf2ra$^{KO}$ mouse show Oil-Red-O-positive and foamy macrophages with accumulated surfactant. (g) Lung histology of WT and Csf2ra$^{KO}$ mice. Note that eosinophilic material and pulmonary surfactant was accumulated in alveolar space and peribronchovascular lymphocytic infiltration was observed in Csf2ra$^{KO}$ mice. BAL levels of total cholesterol (h), GM-CSF (i), and M-CSF (j) were also increased significantly in 10-week old Csf2ra$^{KO}$ mice but not age-matched WT mice.

Engraftment and therapeutic efficacy of PMT of congenic wildtype macrophages in Csf2raKO mice is shown in FIG. 12A-H. Csf2ra$^{KO}$ mice received congenic C57Bl/6 WT bone marrow-derived macrophages (BMDMs) as a single, intrapulmonary instillation (2×10e6 cells/mouse) and were evaluated two months later for tolerance, safety, and therapeutic efficacy. Transplanted BMDMs engrafted as shown by the detection of CD116+ alveolar macrophages in Csf2ra$^{KO}$ recipients (FIG. 12a-b). Further, alveolar macrophage in PMT-treated Csf2ra$^{KO}$ mice were small, not foamy in appearance, and far fewer stained positive with Oil-Red-O than those in untreated Csf2ra$^{KO}$ mice, which were enlarged, foamy, and mostly Oil-Red-O positive (FIG. 12c).

In untreated Csf2ra$^{KO}$ mice, PAP lung disease severity worsened progressively over time similar to that seen in hPAP children, as demonstrated by a progressive increase in BAL turbidity (FIG. 12h). In marked contrast, two months after a single PMT treatment, BAL turbidity was markedly reduced in PMT-treated compared to untreated Csf2ra$^{KO}$ mice (FIG. 12d, e) and the efficacy lasted at least six months (FIG. 12h). A single PMT treatment also reduced PAP biomarkers in BAL including levels of cholesterol (FIG. 12f) and GM-CSF, M-CSF and MCP-1 (FIG. 12g). PMT therapy did not result in treatment-emergent untoward behavioral effects or adverse events in any mice.

Figure 13A:
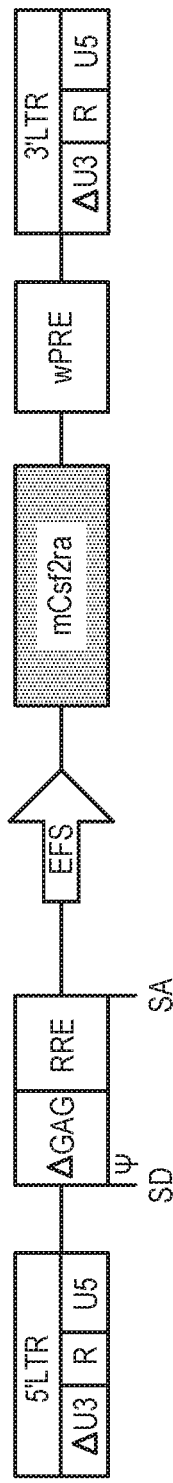
FIG. 13A-D: Efficacy of gene-corrected Csf2ra$^{KO}$ macrophages in vitro and in vivo. (a). Schematic of the SIN-LV vector showing elongation factor 1-alpha short (EFS) promoter driving mouse Csf2ra cDNA (mGM-Rα-LV). (b) Evaluation of GM-CSF receptor signaling by phosphorylated STAT5 measurement in mGM-R$^+$M cells with or without GM-CSF stimulation. (c) In vitro clearance of GM-CSF clearance by mGM-R$^+$M s assesses receptor function. (d) BAL turbidity improves in Csf2ra$^{KO}$ mice that received PMT of mGM-R$^+$Ms2 months post PMT. ***P<0.001.
Figure 13B:
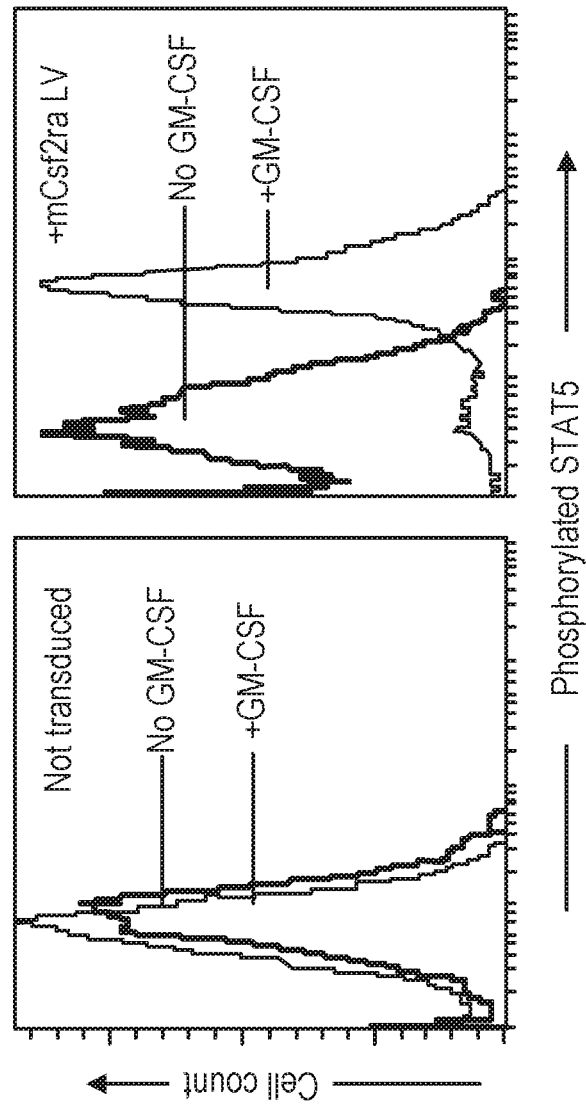
Figure 13D:
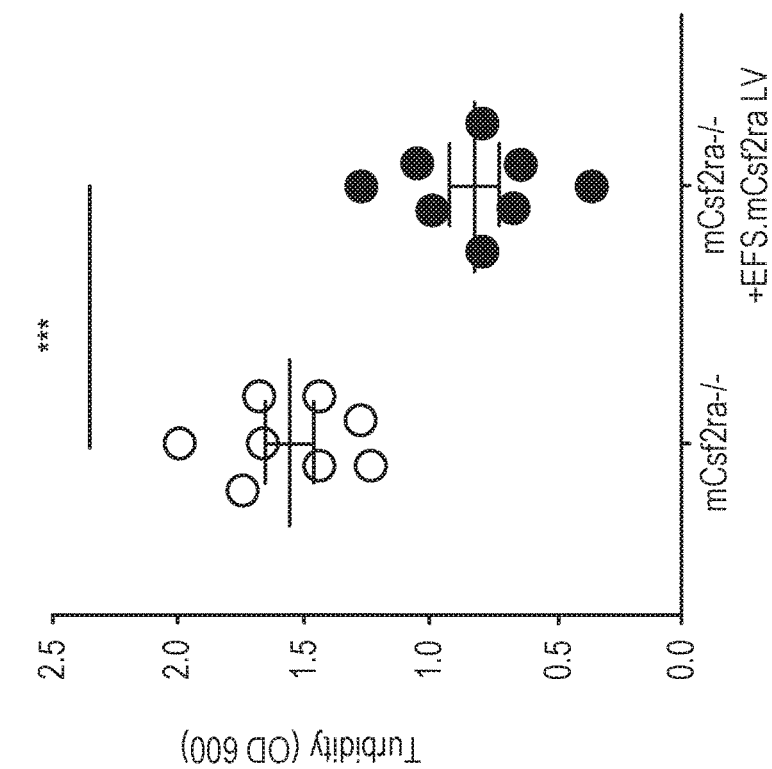
Figure 13C:
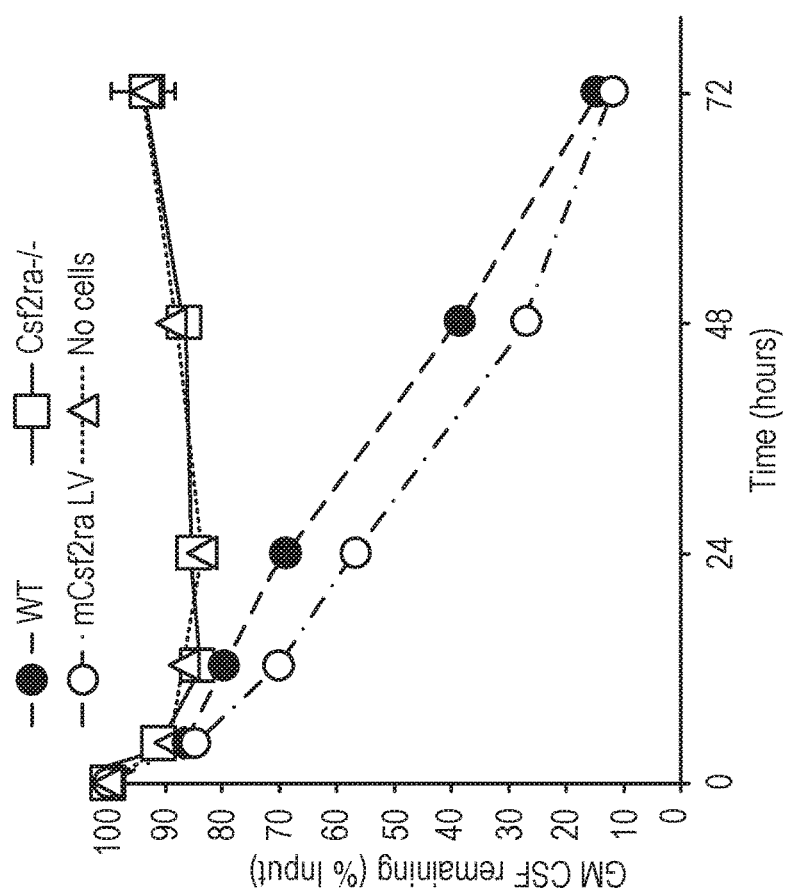

The efficacy of gene-corrected Csf2ra$^{KO}$ macrophages in vitro and in vivo is shown in FIG. 13A-D. We cloned a murine Csf2ra cDNA carrying lentiviral vector (mGM-Rα-LV) utilizing the same backbone as that of the intended clinical vector (hGM-Rα-LV) (FIG. 13a). Using this vector, we generated Csf2ra$^{KO}$ gene-corrected macrophages by transducing Csf2ra$^{KO}$ LSK cells (mGM-Rα+MΦs). These macrophages were F4/80$^+$CD11b$^{Hi}$CD11c$^+$ (data not shown). mGMRα+MΦs exhibited restored pSTAT5 signaling (FIG. 13b) and GM clearance functions (FIG. 13c) in vitro.

Next we evaluated PMT efficacy of the mGM-Rα+MDs in Csf2ra$^{KO}$ recipients. mGM-Rα+MΦs cleared abnormal surfactant accumulation (FIG. 13d), as shown by a significant (P<0.001) decrease in BAL turbidity in Csf2ra$^{KO}$ recipients compared to no PMT Csf2ra$^{KO}$ control mice.

2. Effects of Cell Dose on Therapeutic Efficacy

Figure 14A:
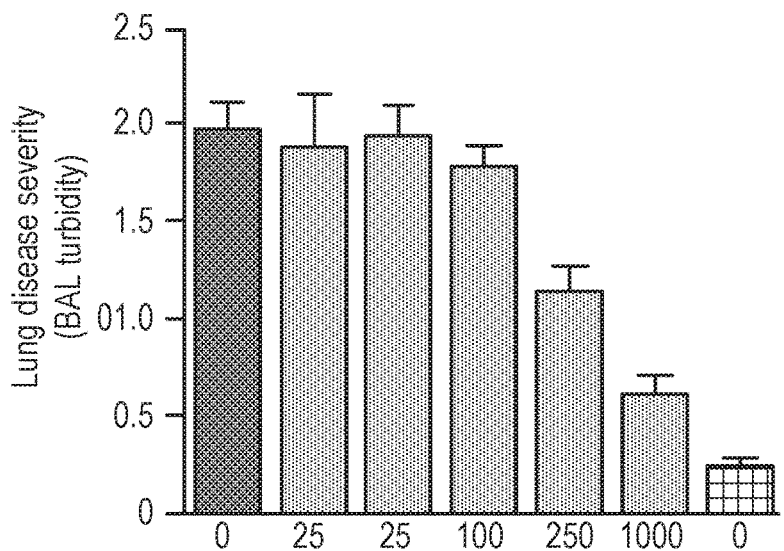
FIG. 14A-B: Evaluation of dose-response relationship with wild-type macrophages and Csf2rb gene-corrected macrophages. Turbidity was measured 2 months following PMT and disease severity was determined as described herein for (a) wild-type macrophages (doses=25, 25, 100, 250, and 1000, each ×1000 cells/mouse) and (b) mGM-Rβ+ MΦ cells (25, 25, 100, 250, 1000). In both (a) and (b) the left most bar marked 0 is a positive control (no PMT, Csf2rb−/− mice). In (a) the right most bar marked 0 is a negative control (no PMT, Csf2rb+/+mice). In (b) the right most bar shows wild-type donor source at a cell dose of 250e3 cells, as a comparator to the same dose of transduced cells in the same experiment. Statistical analysis was performed using Bonferroni's multiple comparison test. *P<0.001, **P<0.0001.
Figure 14B:
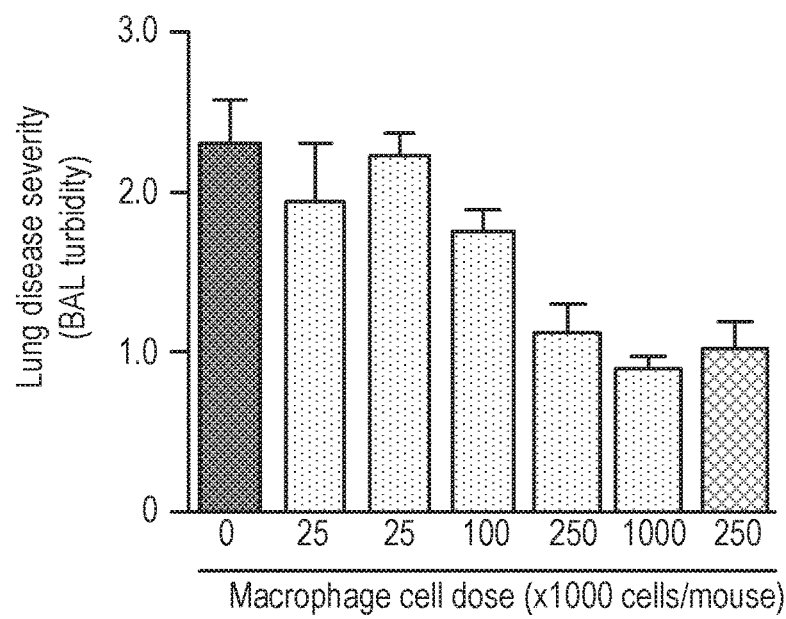

FIG. 14A-B shows the evaluation of the dose-response relationship with wild-type macrophages and Csf2rb gene-corrected macrophages. In order to establish a PMT dose-response relationship and to identify the safe and effective dose for humans, wild-type (WT) CD45.1+ murine bone marrow Lin-Sca1+cKit+ (LSK) hematopoietic stem/progenitors were obtained and differentiated in vitro according to the methods described above into mature macrophages. CD11cHiF4/80Hi macrophages were isolated by cell sorting, and various doses (2500, 25000, 100000, 250000, 1000000 cells/mouse; n=6-7/doses) were administered by PMT to CD45.2+Csf2rb$^{KO}$ mice. Therapeutic efficacy was evaluated after 8 weeks (2 months) by measuring the optical density (OD λ=600 nm) of BAL turbidity and determining disease severity as described above. FIG. 14a shows a steady decrease in disease severity (BAL turbidity) in PMT treated mice compared to age-matched, untreated controls. Moreover, the decrease in severity was correlated with increasing cell dose over the entire range tested, reaching statistical significance at the two highest doses, 2.5×10e5 and 1×10e6 (FIG. 14a).

Next, we evaluated the dose-response relationship using Csf2rb transduced cells, referred to as mGM-Rβ+MΦs. Briefly, LSK cells were isolated from Csf2rb$^{KO}$ donors, transduced with mGM-Rβ-LV using established procedures, expanded and differentiated into macrophages in vitro (mGM-Rβ+MΦs). Mice were treated with the same range of doses as described above for wild-type macrophages). The gene-corrected cells were administered by PMT into Csf2rb$^{KO}$ recipients and BAL turbidity was determined. FIG. 14b shows a similar cell dose-response is obtained with PMT of gene corrected cells.

These results establish a direct relationship between the number of macrophages transplanted (cell dose) and efficacy of PMT therapy of hPAP and was used to determine the minimum effective dose range in humans.

3. Human GM-Rα-LV (hGM-Rα-LV) Restores GM-CSF Receptor Function In Vitro

Figures 15C, 15D:
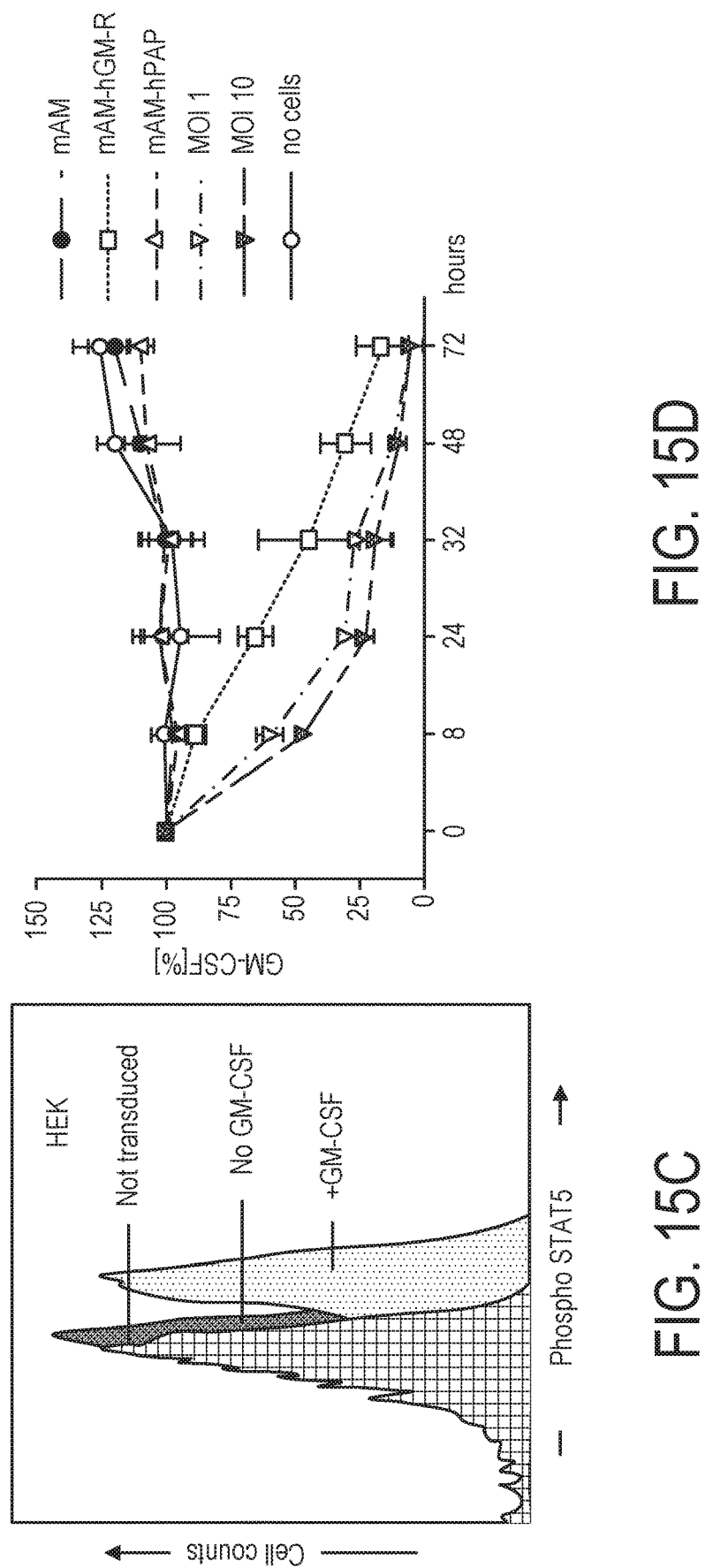

These experiments complement those described in FIG. 9 above and panels 15a and 15d of FIG. 15 reproduce the data shown above in FIG. 9e and FIG. 9g, respectively, for reference. As described above, in order to evaluate the functionality of the clinical vector, the mAM-hPAP cell line was created and used to evaluate the ability of the transgene to restore CD116 expression and GM-CSF clearance. In addition, we created a human embryonic kidney (HEK293) cell line carrying the same transgenes, that is a wild-type human CSF2R beta chain and a mutant CSF2R alpha chain (G196R in exon 7). In both cell lines, the untransduced cells do not express CD116, are unable to phosphorylate STAT5, and are unable to clear GM-CSF from culture medium. Lentiviral mediated expression of normal CSF2RA rescues these functionalities in both the murine mAM-hPAP and human HEK293 cells. Increasing multiplicities of infection (MOIs) of 5, 10, 15, and 25 correlated with increased CD116 expression in both cell lines, as shown in FIG. 15b. Restoration of GM-CSF receptor function in HEK293 cells as measured by pSTAT5 signaling in response to GM-CSF addition is shown in FIG. 15c. The percentage of CD116 expressing cells was >80% for HEK and >95% for mAM cell lines.

Figure 16A:
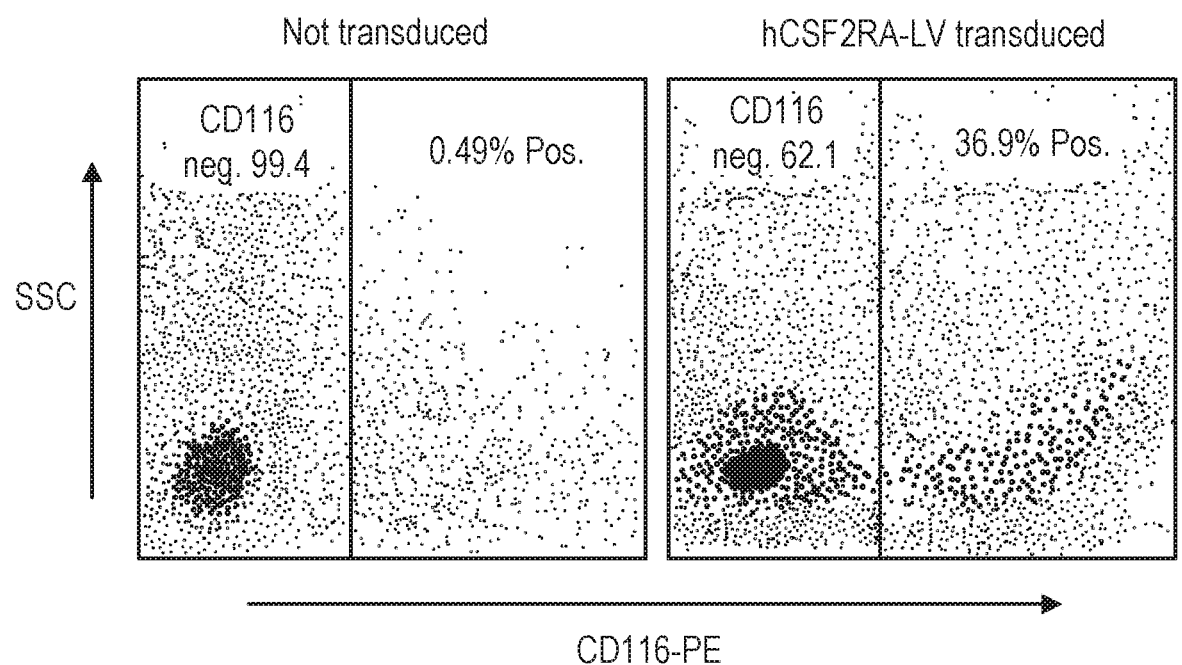
FIG. 16A-E: Nontransduced hPAP (left) and hGM-Rα+ Mbs (right) are shown. Restoration of GM-Rα function in primary human hPAP patient derived cells after GM-Rα LV transduction (a) Initial transduction efficiency in colony forming units on day 14 (b) Total colony numbers in the presence of G-CSF and GM-CSF (c) Cytospins of colonies after differentiation with either G-CSF (left) or GM-CSF alone (d) Top panel shows gating strategy for CD116+ cells. Bottom panel shows pSTAT5 fluorescence before (empty histogram) and after (filled histogram) GM-CSF stimulation.
Figure 16B:
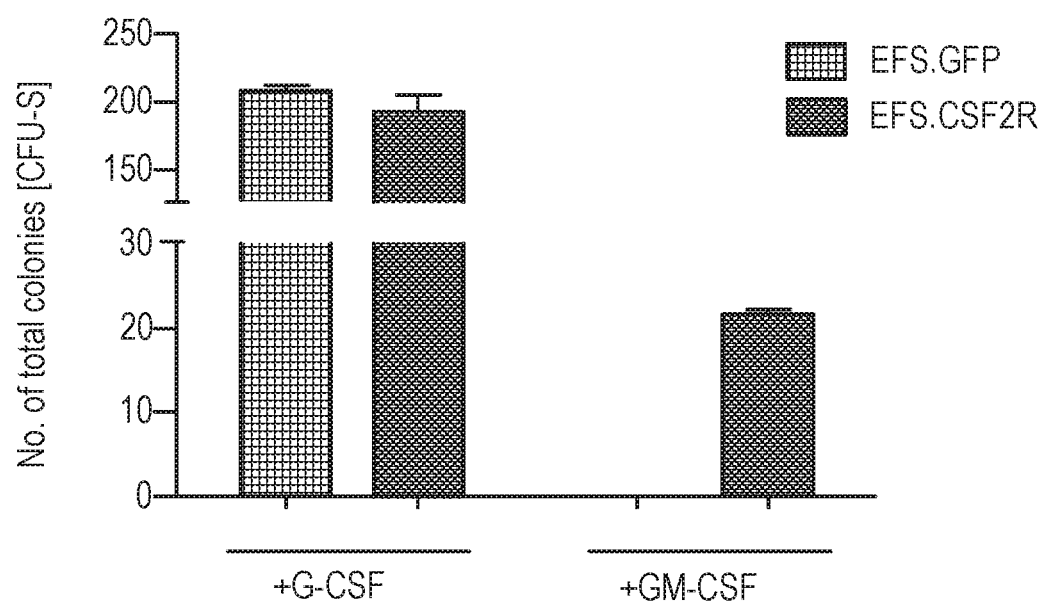
Figure 16C:
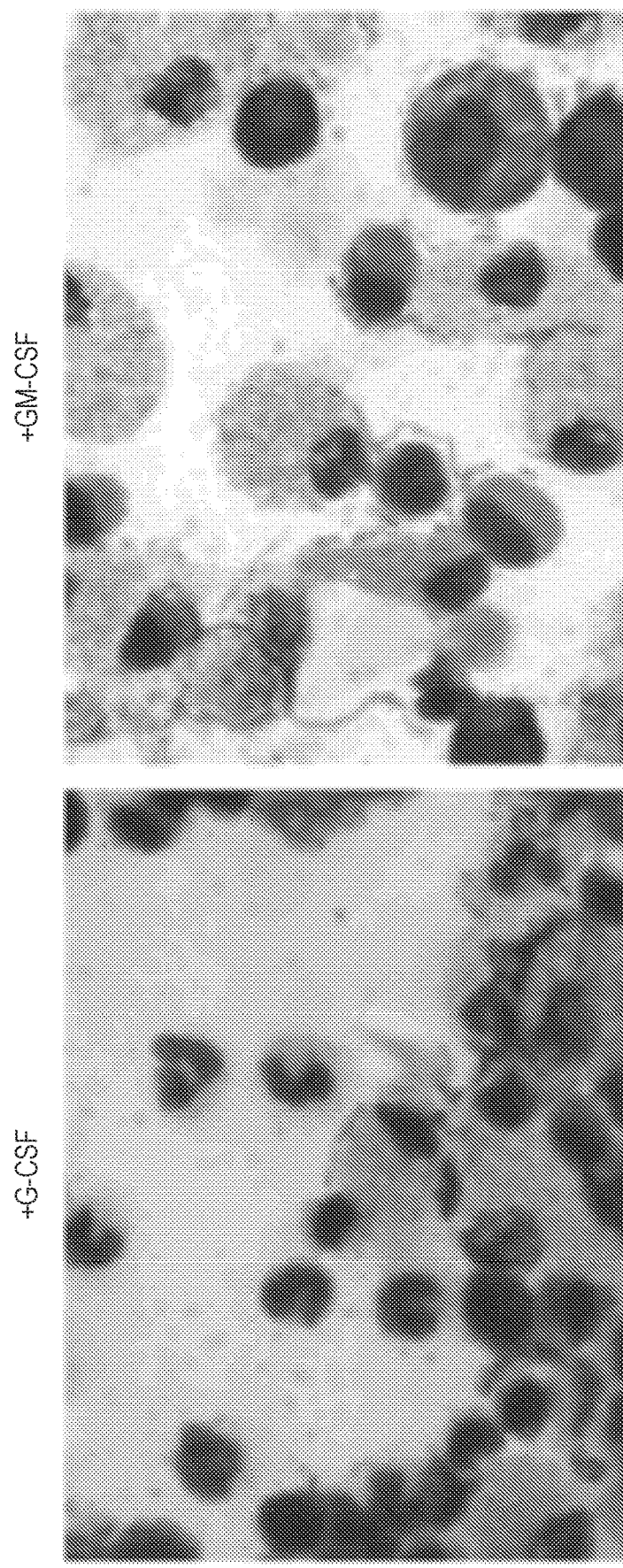
Figure 16D:
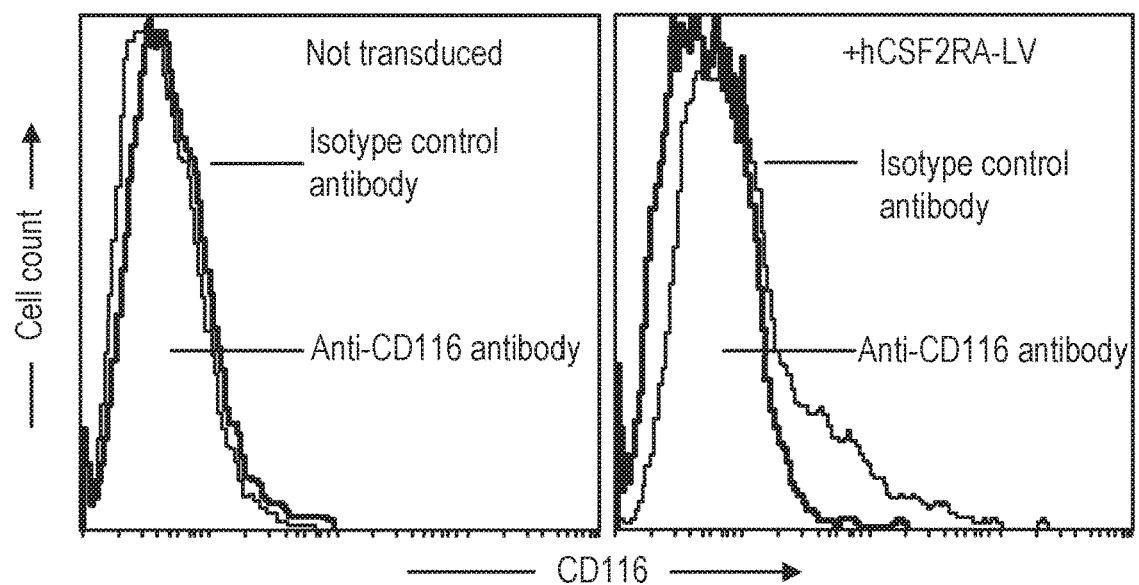
Figure 16E:
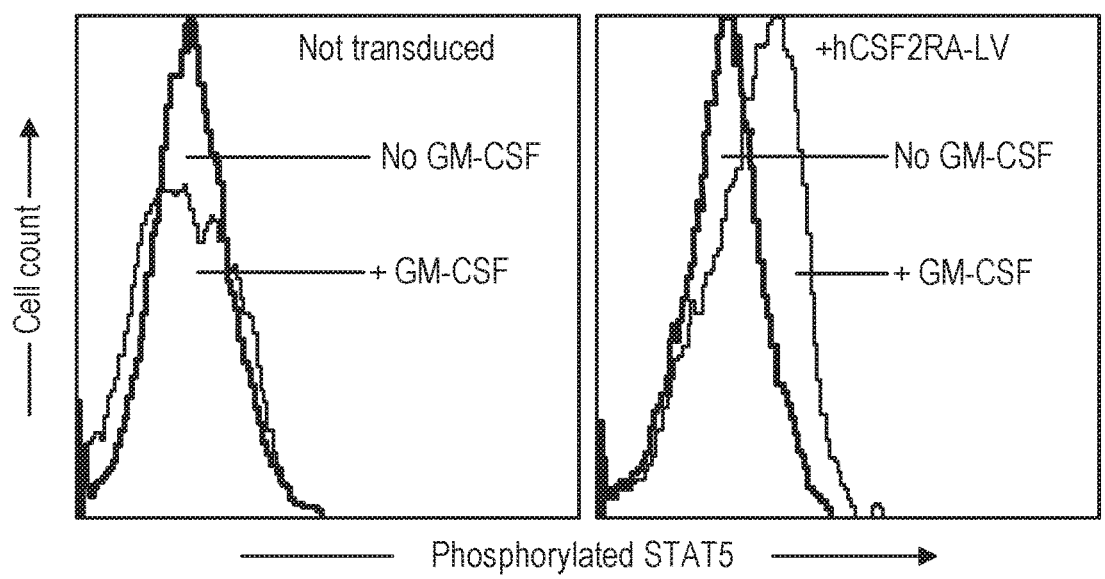

4. Human GM-Rα-LV (hGM-Rα-LV) Restores GM-CSF Receptor Function in Primary Human Cells from an hPAP Patient CD34+ cells isolated from the bone marrow of an hPAP patient were transduced with hGM-Rα-LV using optimized serum-free hematopoietic stem cell transduction conditions. The hCSF2RA (CD116) transgene expression (FIG. 16a) in the day 14 colony forming units (bulk) was 37% (Average vector copy number-0.52). There was no difference in the number of CFU-G colonies in the presence of G-CSF between the hGM-Rα+MΦs and hGM-Rα−MΦs cells, whereas upon GM-CSF addition, an increase in the number of CFU-M colonies were found compared to hGM-Rα−MΦs (FIG. 16b). Representative cytospin pictures are shown (FIG. 16c). These transduced cells were expanded and differentiated into macrophages in vitro under optimized culture conditions. At day 21, adherent macrophages were collected and tested for GM-CSF receptor expression assay (FIG. 16d) and function using a well-established pSTAT5 assay. Only hGMRα+MΦs show restoration of GM-CSF receptor function in a human GM-CSF stimulated pSTAT5 assay. The hGM-Rα−MΦs did not show pSTAT5 signaling upon GM-CSF stimulation (FIG. 16e). These results demonstrate the efficacy of the clinical vector to restor GM-CSF functionality in human primary cells transduced and in vitro differentiated into macrophages using the protocols described here.

Figure 17A:
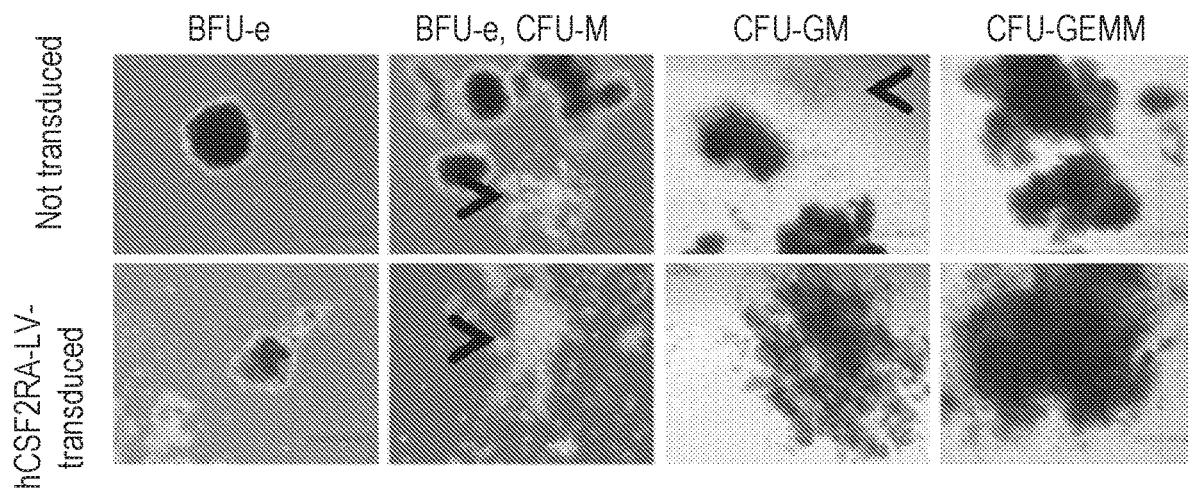
FIG. 17A-B: Improved myeloid differentiation in clonogenic progenitors in GM-Rα LV transduced hPAP HSCs. (a) Colony forming ability of hPAP patient's CD34+ cells following GM-Rα LV transduction and plating. (b) Absolute progenitor colony (BFU-e, CFU-GM, CFU-M and CFU-GEMM) counts of nontransduced hPAP (left bar of each pair) and hGM-Rα+MΦs (right bar of each pair) is shown. Arrows indicate CFU-M colonies. Reproduced from Suzuki et al FIG. 18. GM-Rα-LV provirus is stable in murine and human cell lines.
Figure 17B:
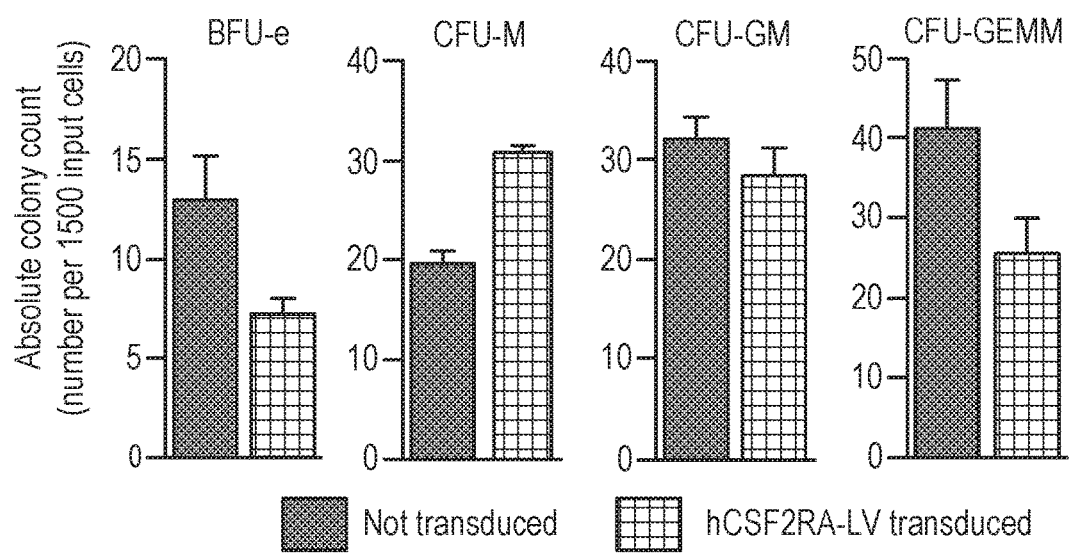

5. Preclinical Studies Using hPAP Patient CD34+ HSPCs to Assess hCSF2RA Gene Transfer Efficiency and Progenitor Colony Forming Ability CD34+ cells were isolated from the bone marrow of an hPAP patient and transduced with hGM-Rα-LV using optimized serum-free hematopoietic stem cell transduction conditions. The cells were transduced twice at a viral concentrations of $2.5 \times 10e7$ transduction units (TU)/mL, with approximately 24 hours of viral exposure. A portion of CD34+ cells was maintained under the same conditions without lentiviral vector transduction for further functional analysis. Lentiviral vector transduced and nontransduced cells were washed and 1,500 cells were plated for colony forming unit (CFU) assays in methocult medium (H4434, Stem Cell Technologies). The remaining cells were placed in the expansion cocktail for expansion and differentiation into macrophages. After culturing in methocult medium for 14 days, BFU-e, CFU-GM, CFU-M, and CFU-GEMM colonies were scored. The total number of CFU-C were similar between the transduced macrophage cells (hGM-Rα+MΦ) and untransduced cells (hGM-Rα−MΦ) (FIG. 17a). There was a trend towards decreased BFU-e and CFU-GEMM colony numbers, a trend towards increased CFU-M numbers, and no difference in the CFU-GM colony numbers in the transduced compared to untransduced cells (FIG. 17b) indicating no significant impact on the differentiation of progenitors towards the myeloid lineage following functional GM-Rα expression via LV transduction.

6. hGM-Rα-LV Provirus is Stable in Murine and Human Cell Lines

Figure 18:
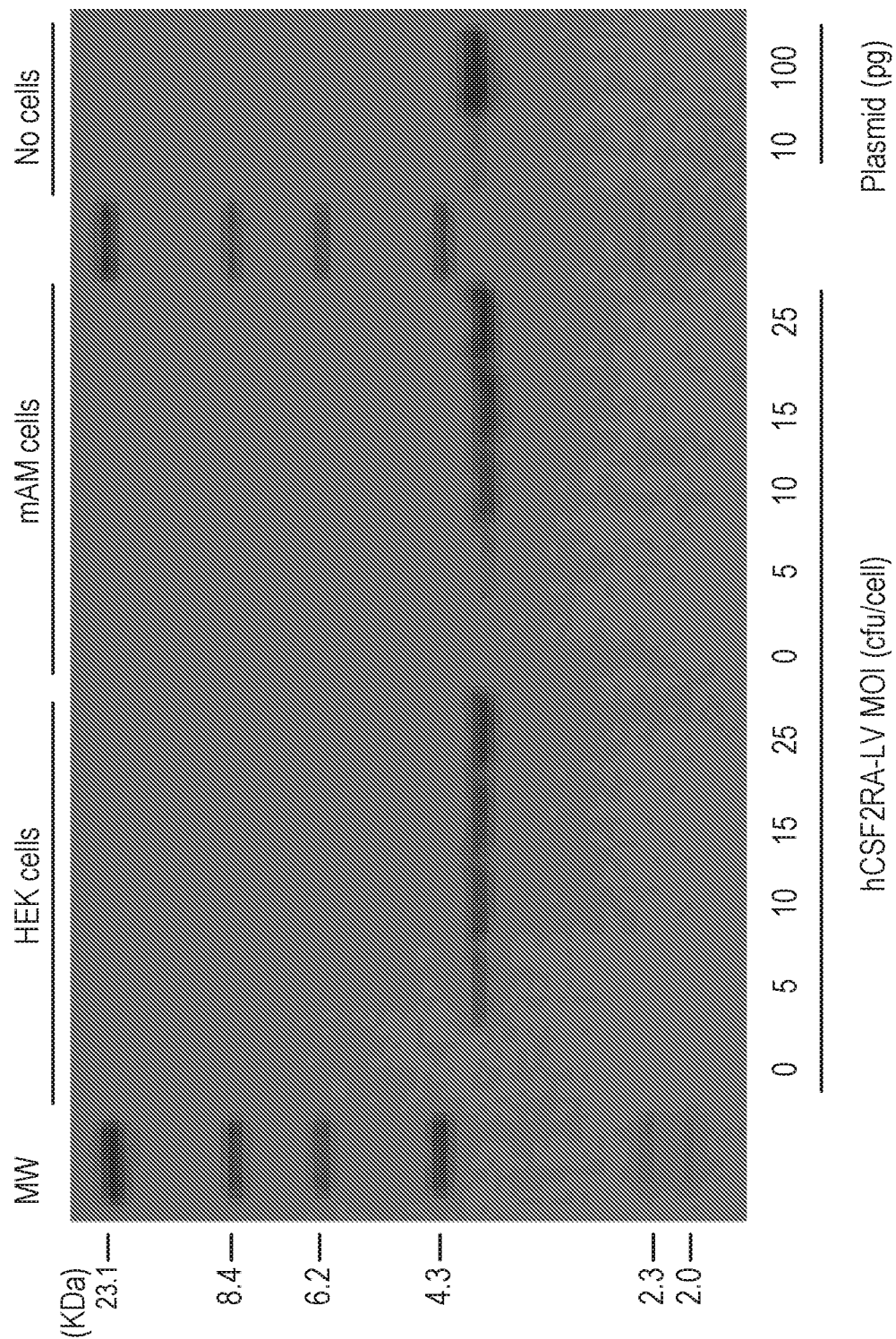

FIG. 18 shows that the hGM-Rα-LV provirus is stable in murine and human cell lines. Southern blot analysis on genomic DNA isolated from the HEK and mAM cell lines transduced with the hGMRα-LV transduced pools is shown. Genomic DNA was digested with the restriction enzyme MIL This enzyme cuts in the "R" region of the LTR resulting in an intact 3.9 kb proviral size, as shown. Southern blot analysis of vector transduced pools 21 days after transduction shows one single band of the expected size (3.9 kb) demonstrating absence of large deletions or any rearrangements and thereby confirming proviral stability.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A self-inactivating lentiviral vector comprising a human CSF2RA cDNA, the human CSF2RA cDNA comprising the sequence identified by nucleotides 2084 to 3299 of SEQ ID NO:1.

2. The vector of claim 1, wherein the expression of the human CSF2RA cDNA is under the control of a human elongation factor 1-alpha short promoter (EFS).

3. The vector of claim 1, further comprising a woodchuck hepatitis post-transcriptional regulatory element (wPRE).

4. The vector of claim 3, wherein the wPRE sequence is detectable by polymerase chain reaction amplification using a set of forward and reverse primers identified by SEQ ID NOs: 2 and 3.

5. The vector of claim 1, wherein the vector envelope pseudo-type is VSV-G.

6. A composition comprising the vector of claim 1, and a carrier.

7. The composition of claim 6, wherein the carrier is selected from an aqueous solution buffered to physiological pH, saline or other physiologically buffered salt solution, and a cell culture medium.

8. The composition of claim 6, wherein the composition comprises a VSV-G envelope plasmid, a gag/pol plasmid, and a rev plasmid.

9. A composition comprising virions containing the vector of claim 1, and a carrier.

10. The composition of claim 9, wherein the composition contains 5×10e7 virions per ml or is characterized by an infectious titer of 1-5×10e8 IU/ml.

11. A composition comprising human bone marrow derived CD34+ cells transduced with the vector of claim 1, and a carrier.

12. A cell freeze bag or cryovial comprising the composition of claim 11.

13. The composition of claim 11, wherein the composition comprises a cryopreservation excipient.

14. A composition comprising non-naturally occurring in vitro differentiated human macrophage cells derived from CD34+ cells transduced with the vector of claim 1, wherein the macrophage cells express human CSF2RA, and a carrier.

15. The composition of claim 14, wherein the composition comprises less than 2% CD34+ cells and greater than 70% CD11b+ cells.

16. The composition of claim 14, wherein the composition is sterile.

17. The composition of claim 14, wherein the composition contains from 2-20×10e6 cells/mL.

18. The composition of claim 14, wherein the macrophage cells are autologous to a human subject having hereditary pulmonary alveolar proteinosis (hPAP).

19. The composition of claim 14, wherein the composition comprises a cryopreservation excipient.

20. A method for treating hPAP in a human subject in need thereof, the method comprising administering to a lung segment of the subject a therapeutic amount of a composition comprising non-naturally occurring in vitro differentiated human macrophage cells derived from CD34+ cells transduced with a self-inactivating lentiviral vector comprising a human CSF2RA cDNA, the human CSF2RA cDNA comprising the sequence identified by nucleotides 2084 to 3299 of SEQ ID NO:1, wherein the macrophage cells express the human CSF2RA.

21. The method of claim 20, wherein the composition is administered by direct instillation to the individual lung segments.

22. The method of claim 20, wherein the administration is through a flexible fiberoptic bronchoscope.

23. The method of claim 20, wherein the therapeutic amount is a dose of from 5 to 6×10e5 cells per lung segment per kilogram weight of the subject.

24. The method of claim 20, wherein the therapeutic amount is a cumulative cell dose of from 400 to 800×10e6 cells—for a 70 kg human subject.

25. The method of claim 20, wherein the macrophage cells are autologous to the human subject.

26. A method for producing modified human macrophage cells for use in the treatment of hPAP in a human patient, the method comprising
    isolating CD34+ hematopoietic progenitor cells from a mononuclear cell enriched fraction of the patient's bone marrow,
    culturing the cells for 8-12 or 12-14 hours in medium comprising stem cell factor (SCF), thrombopoietin, Flt3-ligand, interleukin-6, interleukin-3, granulocyte macrophage colony stimulating factor (GM-CSF), and macrophage colony stimulating factor (M-CSF),
    transducing the CD34+ cells with the lentiviral vector of claim 1,
    culturing the transduced cells for 5-6 days in medium optimized to promote cell growth to provide an expanded population of transduced CD34+ cells,
    culturing the expanded CD34+ cells in a three-stage culture system for an additional 14-15 days to obtain modified human macrophage cells, wherein during this period of time the concentrations of recombinant stem cell cytokines are gradually decreased while the concentrations of myeloid differentiation cytokines, recombinant MCSF and GM-CSF, are simultaneously increased to favor production of macrophages, and
    cryopreserving the modified human macrophage cells.

27. A composition comprising modified human macrophage cells produced according to the method of claim 26.

28. A composition comprising virions containing a self-inactivating lentiviral vector comprising a human CSF2RA cDNA, the human CSF2RA cDNA comprising the sequence identified by nucleotides 2084 to 3299 of SEQ ID NO:1.

* * * * *

SEQUENCE LISTING

<160> NUMBER OF SEQ ID NOS: 5

<210> SEQ ID NO 1
<211> LENGTH: 7586
<212> TYPE: DNA

<213> ORGANISM: Artificial Sequence
<220> FEATURE:
<223> OTHER INFORMATION: cDNA of Human CSF2RA gene

<400> SEQUENCE: 1

```
ccgattggtg gaagtaaggt ggtacgatcg tgccttatta ggaaggcaac agacgggtct      60
gacatggatt ggacgaacca ctgaattgcc gcattgcaga gatattgtat ttaagtgcct     120
agctcgatac aataaacggg tctctctggt tagaccagat ctgagcctgg gagctctctg     180
gctaactagg gaacccactg cttaagcctc aataaagctt gccttgagtg cttcaagtag     240
tgtgtgcccg tctgttgtgt gactctggta actagagatc cctcagaccc ttttagtcag     300
tgtggaaaat ctctagcagt ggcgcccgaa cagggacctg aaagcgaaag gaaaccaga     360
gctctctcga cgcaggactc ggcttgctga agcgcgcacg gcaagaggcg aggggcggcg     420
actggtgagt acgccaaaaa ttttgactag cggaggctag aaggagagag atgggtgcga     480
gagcgtcagt attaagcggg ggagaattag atcgcgatgg gaaaaaattc ggttaaggcc     540
agggggaaag aaaaaatata aattaaaaca tatagtatgg gcaagcaggg agctagaacg     600
attcgcagtt aatcctggcc tgttagaaac atcagaaggc tgtagacaaa tactgggaca     660
gctacaacca tcccttcaga caggatcaga agaacttaga tcattatata atacagtagc     720
aaccctctat tgtgtgcatc aaaggataga gataaaagac accaaggaag ctttagacaa     780
gatagaggaa gagcaaaaca aaagtaagac caccgcacag caagcggccg ctgatcttca     840
gacctggagg aggagatatg agggacaatt ggagaagtga attatataaa tataaagtag     900
taaaaattga accattagga gtagcaccca ccaaggcaaa gagaagagtg gtgcagagag     960
aaaaaagagc agtgggaata ggagctttgt tccttgggtt cttgggagca gcaggaagca    1020
ctatgggcgc agcctcaatg acgctgacgg tacaggccag acaattattg tctggtatag    1080
tgcagcagca gaacaatttg ctgagggcta ttgaggcgca acagcatctg ttgcaactca    1140
cagtctgggg catcaagcag ctccaggcaa gaatcctggc tgtggaaaga tacctaaagg    1200
atcaacagct cctggggatt tggggttgct ctggaaaact catttgcacc actgctgtgc    1260
cttggaatgc tagttggagt aataaatctc tggaacagat ttggaatcac acgacctgga    1320
tggagtggga cagagaaatt aacaattaca caagcttaat acactcctta attgaagaat    1380
cgcaaaacca gcaagaaaag aatgaacaag aattattgga attagataaa tgggcaagtt    1440
tgtggaattg gtttaacata caaaattggc tgtggtatat aaaattattc ataatgatag    1500
taggaggctt ggtaggttta agaatagttt ttgctgtact ttctatagtg aatagagtta    1560
ggcagggata ttcaccatta tcgtttcaga cccacctccc aaccccgagg ggacccgaca    1620
ggcccgaagg aatagaagaa gaaggtggag agagagacag agacagatcc attcgattag    1680
tgaacggatc tcgacggtat cggttaactt ttaaaagaaa aggggggatt ggggggtaca    1740
gtgcagggga agaatagta gacataatag caacagacat acaaactaaa gaattacaaa    1800
aacaaattac aaaaattcaa aattttatcg attggctccg gtgcccgtca gtgggcagag    1860
cgcacatcgc ccacagtccc cgagaagttg gggggagggg tcggcaattg aaccggtgcc    1920
tagagaaggt ggcgcggggt aaactgggaa agtgatgtcg tgtactggct ccgcctttt    1980
cccgagggtg ggggagaacc gtatataagt gcagtagtcg ccgtgaacgt tcttttttcgc    2040
aacgggtttg ccgccagaac acaggtcgtc tgacgcggga tccaccggtg ccaccatgct    2100
gctgctcgtc acaagcctgc tgctgtgcga gctgccccac cctgcctttc tgctgatccc    2160
cgagaagtcc gacctgcgga cagtggcccc tgccagctct ctgaacgtgc gcttcgacag    2220
```

```
ccggaccatg aacctgagct gggactgcca ggaaaacaca accttcagca agtgcttcct    2280
gaccgacaag aaaaaccggg tggtggaacc ccggctgagc aacaacgagt gctcctgcac    2340
ctttagagag atctgcctgc acgagggcgt gaccttcgag gtgcacgtga acaccagcca    2400
gcggggcttc cagcagaagc tgctgtaccc aacagcggc agagagggaa cagccgccca     2460
gaacttcagc tgcttcatct acaacgccga cctgatgaac tgcacctggg ccagaggacc    2520
taccgccccc agagatgtgc agtacttcct gtacatccgg aacagcaagc ggcggagaga    2580
aatccggtgc ccatactata tccaggacag cggcacacac gtgggctgcc acctggataa    2640
tctgagcggc ctgaccagcc ggaactactt cctcgtgaac ggcaccagca gagagatcgg    2700
catccagttc ttcgactccc tgctggacac caagaagatc gagcggttca accccccag    2760 caacgtgacc gtgcggtgca ataccaccca ctgcctcgtg cggtggaagc agcccagaac    2820
ctaccagaag ctgagctacc tggacttcca gtaccagctg gacgtgcacc ggaagaacac    2880
ccagcccggc accgagaacc tgctgatcaa cgtgtccggc gacctggaaa acagatacaa    2940
cttccccagc agcgagccca gagccaagca cagcgtgaag atcagagccg ccgacgtgcg    3000
gatcctgaac tggtcctctt ggagcgaggc catcgagttc ggcagcgacg atggcaatct    3060
gggcagcgtg tacatctacg tgctgctgat tgtgggcacc ctcgtgtgcg gaatcgtgct    3120
gggcttcctg ttcaagcggt tcctgcggat ccagagactg ttcccccag tgccccaaat    3180 caaggacaag ctgaacgaca ccacgaggt ggaagatgag atcatctggg aggaattcac    3240
ccccgaggaa ggcaagggct accgggaaga ggtgctgacc gtgaaagaga tcacctgagt    3300
cgacggatcc cccgggctgc aggaattcga gcatcttacc gccatttata cccatatttg    3360
ttctgttttt cttgatttgg gtatacattt aaatgttaat aaaacaaaat ggtgggcaa     3420 tcatttacat ttttagggat atgtaattac tagttcaggt gtattgccac aagacaaaca    3480
tgttaagaaa ctttcccgtt atttacgctc tgttcctgtt aatcaacctc tggattacaa    3540
aatttgtgaa agattgactg atattcttaa ctatgttgct ccttttacgc tgtgtggata    3600
tgctgcttta atgcctctgt atcatgctat tgcttcccgt acggctttcg ttttctcctc    3660
cttgtataaa tcctggttgc tgtctcttta tgaggagttg tggcccgttg tccgtcaacg    3720
tggcgtggtg tgctctgtgt ttgctgacgc aaccccact ggctgggca ttgccaccac     3780 ctgtcaactc ctttctggga cttcgcttt cccctcccg atcgccacgg cagaactcat     3840
cgccgcctgc cttgcccgct gctggacagg ggctaggttg ctgggcactg ataattccgt    3900
ggtgttgtcg gggaagctga cgtcctttcg aattcgatat caagctgtac ctttaagacc    3960
aatgacttac aaggcagctg tagatcttag ccactttta aagaaaagg ggggactgga     4020 agggctaatt cactcccaac gaagacaaga tctgcttttt gcttgtactg ggtctctctg    4080
gttagaccag atctgagcct gggagctctc tggctaacta gggaacccac tgcttaagcc    4140
tcaataaagc ttgccttgag tgcttcaagt agtgtgtgcc cgtctgttgt gtgactctgg    4200
taactagaga tccctcagac cctttagtc agtgtggaaa atctctagca gtagtagttc    4260
atgtcatctt attattcagt atttataact tgcaaagaaa tgaatatcag agagtgagag    4320
gaacttgttt attgcagctt ataatggtta caaataaagc aatagcatca caaatttcac    4380
aaataaagca tttttttcac tgcattctag ttgtggtttg tccaaactca tcaatgtatc    4440
ttatcatgtc tggctctagc tatcccgccc ctaactccgc ccagttccgc ccattctccg    4500
ccccatggct gactaatttt ttttatttat gcagaggccg aggccgcctc ggcctctgag    4560
```

```
ctattccaga agtagtgagg aggcttttt ggaggcctag gcttttgcgt cgagacgtac    4620
ccaattcgcc ctatagtgag tcgtattacg cgcgctcact ggccgtcgtt ttacaacgtc    4680
gtgactggga aaaccctggc gttacccaac ttaatcgcct tgcagcacat ccccctttcg    4740
ccagctggcg taatagcgaa gaggcccgca ccgatcgccc ttcccaacag ttgcgcagcc    4800
tgaatggcga atggcgcgac gcgccctgta gcggcgcatt aagcgcggcg ggtgtggtgg    4860
ttacgcgcag cgtgaccgct acacttgcca gcgccctagc gcccgctcct ttcgctttct    4920
tcccttcctt tctcgccacg ttcgccggct ttccccgtca gctctaaat cggggggctcc    4980
ctttagggtt ccgatttagt gctttacggc acctcgaccc caaaaaactt gattagggtg    5040
atggttcacg tagtgggcca tcgccctgat agacggtttt tcgccctttg acgttggagt    5100
ccacgttctt aatagtgga ctcttgttcc aaactggaac aacactcaac cctatctcgg    5160
tctattcttt tgatttataa gggattttgc cgatttcggc ctattggtta aaaaatgagc    5220
tgatttaaca aaaatttaac gcgaatttta acaaaatatt aacgtttaca atttcccagg    5280
tggcactttt cggggaaatg tgcgcggaac ccctatttgt ttatttttct aaatacattc    5340
aaatatgtat ccgctcatga gacaataacc ctgataaatg cttcaataat attgaaaaag    5400
gaagagtatg agtattcaac atttccgtgt cgcccttatt ccctttttg cggcattttg    5460
ccttcctgtt tttgctcacc cagaaacgct ggtgaaagta aaagatgctg aagatcagtt    5520
gggtgcacga gtgggttaca tcgaactgga tctcaacagc ggtaagatcc ttgagagttt    5580
tcgccccgaa gaacgttttc caatgatgag cacttttaaa gttctgctat gtggcgcggt    5640
attatcccgt attgacgccg ggcaagagca actcggtcgc cgcatacact attctcagaa    5700
tgacttggtt gagtactcac cagtcacaga aaagcatctt acggatggca tgacagtaag    5760
agaattatgc agtgctgcca taaccatgag tgataacact gcggccaact tacttctgac    5820
aacgatcgga ggaccgaagg agctaaccgc ttttttgcac aacatggggg atcatgtaac    5880
tcgccttgat cgttgggaac cggagctgaa tgaagccata ccaaacgacg agcgtgacac    5940
cacgatgcct gtagcaatgg caacaacgtt gcgcaaacta ttaactggcg aactacttac    6000
tctagcttcc cggcaacaat taatagactg gatggaggcg gataaagttg caggaccact    6060
tctgcgctcg gcccttccgg ctggctggtt tattgctgat aaatctggag ccggtgagcg    6120
tgggtctcgc ggtatcattg cagcactggg gccagatggt aagccctccc gtatcgtagt    6180
tatctacacg acggggagtc aggcaactat ggatgaacga aatagacaga tcgctgagat    6240
aggtgcctca ctgattaagc attggtaact gtcagaccaa gtttactcat atatacttta    6300
gattgattta aaacttcatt tttaatttaa aaggatctag gtgaagatcc ttttttgataa    6360
tctcatgacc aaaatccctt aacgtgagtt ttcgttccac tgagcgtcag accccgtaga    6420
aaagatcaaa ggatcttctt gagatccttt ttttctgcgc gtaatctgct gcttgcaaac    6480
aaaaaaacca ccgctaccag cggtggtttg tttgccggat caagagctac caactctttt    6540
tccgaaggta actggcttca gcagagcgca gataccaaat actgtccttc tagtgtagcc    6600
gtagttaggc caccacttca agaactctgt agcaccgcct acatacctcg ctctgctaat    6660
cctgttacca gtggctgctg ccagtggcga taagtcgtgt cttaccgggt tggactcaag    6720
acgatagtta ccggataagg cgcagcggtc gggctgaacg gggggttcgt gcacacagcc    6780
cagcttggag cgaacgacct acaccgaact gagataccta cagcgtgagc tatgagaaag    6840
cgccacgctt cccgaaggga gaaaggcgga caggtatccg gtaagcggca gggtcggaac    6900
aggagagcgc acgagggagc ttccaggggg aaacgcctgg tatctttata gtcctgtcgg    6960
```

```
gtttcgccac ctctgacttg agcgtcgatt tttgtgatgc tcgtcagggg ggcggagcct    7020
atggaaaaac gccagcaacg cggccttttt acggttcctg gccttttgct ggccttttgc    7080
tcacatgttc tttcctgcgt tatcccctga ttctgtggat aaccgtatta ccgcctttga    7140
gtgagctgat accgctcgcc gcagccgaac gaccgagcgc agcgagtcag tgagcgagga    7200
agcggaagag cgcccaatac gcaaaccgcc tctccccgcg cgttggccga ttcattaatg    7260
cagctggcac gacaggtttc ccgactggaa agcgggcagt gagcgcaacg caattaatgt    7320
gagttagctc actcattagg caccccaggc tttacacttt atgcttccgg ctcgtatgtt    7380
gtgtggaatt gtgagcggat aacaatttca cacaggaaac agctatgacc atgattacgc    7440
caagcgcgca attaaccctc actaaaggga acaaaagctg gagctgcaag cttaatgtag    7500
tcttatgcaa tactcttgta gtcttgcaac atggtaacga tgagttagca acatgcctta    7560
caaggagaga aaaagcaccg tgcatg                                         7586
```

<210> SEQ ID NO 2
<211> LENGTH: 20
<212> TYPE: DNA
<213> ORGANISM: Artificial Sequence
<220> FEATURE:
<223> OTHER INFORMATION: wPRE Forward primer

<400> SEQUENCE: 2
gaggagttgt ggcccgttgt                                                  20

<210> SEQ ID NO 3
<211> LENGTH: 20
<212> TYPE: DNA
<213> ORGANISM: Artificial Sequence
<220> FEATURE:
<223> OTHER INFORMATION: wPRE Reverse primer

<400> SEQUENCE: 3
tgacaggtgg tggcaatgcc                                                  20

<210> SEQ ID NO 4
<211> LENGTH: 22
<212> TYPE: DNA
<213> ORGANISM: Artificial Sequence
<220> FEATURE:
<223> OTHER INFORMATION: PTBP2 Forward primer

<400> SEQUENCE: 4
tctccattcc ctatgttcat gc                                               22

<210> SEQ ID NO 5
<211> LENGTH: 22
<212> TYPE: DNA
<213> ORGANISM: Artificial Sequence
<220> FEATURE:
<223> OTHER INFORMATION: PTBP2 Reverse primer

<400> SEQUENCE: 5
gttcccgcag aatggtgagg tg                                               22